US007700306B2

(12) United States Patent
Thompson et al.

(10) Patent No.: US 7,700,306 B2
(45) Date of Patent: Apr. 20, 2010

(54) METHOD FOR CHARCTERISING ANALYTES

(75) Inventors: Andrew H. Thompson, Cambridge (GB); Christian Hamon, Frankurt Am Main (DE); Karsten Kuhn, Dortmund (DE); Markus Meyer, Gottingen (DE); Schafer Juergen, Lauterbach (DE); Thomas Neumann, Frankfurt Am Main (DE)

(73) Assignee: Electrophoretics Limited, Cobham (GB)

( * ) Notice: Subject to any disclaimer, the term of this patent is extended or adjusted under 35 U.S.C. 154(b) by 1250 days.

(21) Appl. No.: 10/510,246

(22) PCT Filed: Apr. 4, 2003

(86) PCT No.: PCT/GB03/01485

§ 371 (c)(1),
(2), (4) Date: Jun. 27, 2005

(87) PCT Pub. No.: WO03/087839

PCT Pub. Date: Oct. 23, 2003

(65) Prior Publication Data

US 2006/0040334 A1     Feb. 23, 2006

(30) Foreign Application Priority Data

Apr. 4, 2002    (EP) .................................. 02252440

(51) Int. Cl.
*G01N 33/00* (2006.01)
(52) U.S. Cl. .......................... 435/7.21; 435/7.1; 435/41; 436/501; 436/518; 436/543; 530/300; 530/350; 514/1; 560/1
(58) Field of Classification Search ........................ None
See application file for complete search history.

(56) References Cited

U.S. PATENT DOCUMENTS

| 5,708,137 A | 1/1998 | Toth et al. |
| 5,986,076 A | 11/1999 | Rothschild et al. |

FOREIGN PATENT DOCUMENTS

| JP | 2003-584731 | | 1/2009 |
| WO | 98/32876 A1 | | 7/1998 |
| WO | WO-98/31830 A1 | | 7/1998 |
| WO | WO 98/32876 | * | 7/1998 |
| WO | WO-99/60007 A2 | | 11/1999 |
| WO | WO-00/20870 A1 | | 4/2000 |
| WO | WO-01/68664 A2 | | 9/2001 |
| WO | WO-02/12893 A2 | | 2/2002 |
| WO | WO-02/29003 A2 | | 4/2002 |

OTHER PUBLICATIONS

Li et al. (Rapid Communications in Mass Spectrometry, vol. 8, 1994, pp. 743-749).*
Wu at al. (Analytical Chemistry, 1994, vol. 66, pp. 1637-1645).*
Pappin et al. (Current Biology, 1993, vol. 3, No. 6, pp. 327-332).*
Patchett (Abstracts of Papers, 222nd ACS National Meeting, Chicago, IL, Unites States, Aug. 26-30, 2001).*
Patent Abstracts of Japan, vol. 017, No. 506, Sep. 13, 1993 & JP 05 137599 A (Takara Shuzo Co Ltd.), Jun. 1, 1993.
M. Munchbach et al.; "Quantitation and Facilitated de Novo Sequencing of Proteins by Isotopic N-Terminal Labeling of Peptides with a Fragmentation-Directing Moiety"; Analytical Chemistry, vol. 72, 2000, Mar. 8, 2000, pp. 4047-4057.
Scot R. Weinberger, et al.; "Recent trends in protein biochip technology"; Pharmacogenomics, Ashley Publications, GB, vol. 1, No. 3, Nov. 2000, pp. 395-416, XP009009627.
D.J.C. Pappin et al., "Rapid Identification of Proteins by Pepetide-Mass Fingerprinting", Current Biology, vol. 3, pp. 327-332, 1993.
Matthias Mann et al., "Use of Mass Spectrometric Molecular Weight Information to Identify Proteins in Sequence Databases", Biological Mass Spectrometry, vol. 22, pp. 338-345, 1993.
John R. Yates et al., "Peptide Mass Maps: A Highly Informative Approach to Protein Identification", Analytical Biochemistry, vol. 214, pp. 397-408, 1993.
Eberhard Krause et al., "The Dominance of Arginine-Containing Peptides in Maldi-Derived Tryptic Mass Fingerprints of Proteins", Anal. Chem., vol. 71, pp. 4160-4165, 1999.
Valentina Bonetto et al., "C-Terminal Sequence Determination of Modified Peptides by Maldi MS", Journal of Protein Chemistry, vol. 16, No. 5, pp. 371-374, 1997.
Francesco L. Brancia et al., "Improved Matrix-Assisted Laser Desorption/Ionization Mass Spectrometric Analysis of Tryptic Hydrolysates of Proteins Following Guanidination of Lysine-Containing Peptides", Rapid Communications in Mass Spectrometry, vol. 14, pp. 2070-2073, 2000.
Francesco L. Brancia et al., "A Combination of Chemical Derivatisation and Improved Bioinformatic Tools Optimises Protein Identification for Proteomics", Electrophoresis, vol. 22, pp. 552-559, 2001.
Masahiko Okamoto et al., "High-Sensitivity Detection and Postsource Decay of 2-Aminopyridine-Derivatized Oligosaccharieds With Matrix-Assisted Laser Desorption/Ionization Mass Spectrometry", Anal. Chem., vol. 69, pp. 2919-2926, 1997.

(Continued)

*Primary Examiner*—Lisa V Cook
(74) *Attorney, Agent, or Firm*—Crowell & Moring LLP

(57) ABSTRACT

Provided is a method for characterizing an analyte by matrix assisted laser desorption ionization (MALDI) mass spectrometry, which method comprises:
(a) labelling the analyte with a light-absorbing label that absorbs light at a pre-determined frequency, to form a labelled analyte;
(b) embedding the labelled analyte in a matrix formed from at least one compound that absorbs light, to form an embedded labelled analyte;
(c) desorbing the embedded labelled analyte by exposing it to light having the pre-determined frequency, to form a desorbed analyte; and
(d) detecting the desorbed analyte by mass spectrometry to characterize the analyte.

23 Claims, 22 Drawing Sheets

OTHER PUBLICATIONS

Nanying Bian et al., "Detection Via Laser Desorption and Mass Spectrometry of Multiplex Electrophore-Labeled Albumin", Rapid Communications in Mass Spectrometry, vol. 11, pp. 1781-1784, 1997.

Samy Abdel-Baky et al., "Gas Chromatography/Electron Capture Negative-Ion Mass Spectrometry at the Zeptomole Level", Anal. Chem., vol. 63, pp. 2986-2989, 1991.

Kenneth D. W. Roth et al., "Charge Derivatization of Peptides for Analysis by Mass Spectrometry", Mass Specrometry Review, vol. 17, pp. 255-274, 1998.

Matthias Glueckmann et al., "The Initial Ion Velocity and Its Dependence on Matrix, Analyte and Preparation Method in Ultraviolet Matrix-Assisted Laser Desorption/Ionization", Journal of Mass Spectrometry, vol. 34, pp. 467-477, 1999.

Kuang Jen Wu et al., "Matrix-Assisted Laser Desorption Time-of-Flight Mass Spectrometry of Oligonucleotides Using 3-Hydroxypicolinic Acid as an Ultraviolet-Sensitive Matrix", Rapid Communications in Mass Spectrometry, vol. 7, pp. 142-146, 1993.

K. Strupat et al., "2,5-Dihydroxybenzoic Acid: A New Matrix for Laser Desorption-Ionization Mass Spectrometry", International Journal of Mass Spectrometry and Ion Processes, vol. 111, pp. 89-102, 1991.

R. C. Beavis et al., "Alpha-Cyano-4-Hydroxycinnamic Acid as a Matrix for Matrix-Assisted Laser Desorption Mass Spectrometry", Organic Mass Spectrometry, vol. 27, pp. 156-158, 1992.

Ronald C. Beavis et al., "Cinnamic Acid Derivatives as Matrices for Ultraviolet Laser Desorption Mass Spectrometry of Proteins", Rapid Communications in Mass Spectrometry, vol. 3, No. 12, pp. 432-435, 1989.

Michael C. Fitzgerald et al., "Basic Matrices for the Matrix-Assisted Laser Desorption/Ionization Mass Spectrometry of Proteins and Oligonucleotides", Anal. Chem., vol. 65, pp. 3204-3211, 1993.

Victor L. Talrose et al., "Insight Into Absorption of Radiation/Energy Transfer in Infrared Matrix-Assisted Laser Desorption/Ionization: the Role of Matrices, Water and Metal Substrates", Rapid Communications in Mass Spectrometry, vol. 13, pp. 2191-2198, 1999.

Sven Ring et al., "A Comparative Study of a Liquid and a Solid Matrix in Matrix-Assisted Laser Desorption/Ionization Time-of-Flight Mass Spectrometry and Collision Cross Section Measurements", Rapid Comminications in Mass Spectrometry, vol. 14, pp. 515-519, 2000.

Eric T. P. Sze et al., "Formulation of Matrix Solutions for Use in Matrix-Assisted Laser Desorption/Ionization of Biomolecules", J. Am. Soc. Mass Spectrometry, vol. 9, No. 2, pp. 166-174, 1998.

Michael Karas et al., "Matrix-Assisted Laser Desorption Ionization Mass Spectrometry", Mass Spectrometry Reviews, vol. 10, pp. 335-357, 1991.

T. William Hutchens et al., "New Desorption Strtegies for the Mass Spectrometric Analysis of Macromolecules", Rapid Communications in Mass Spectrometry, vol. 7, pp. 576-580, 1993.

Linxiao Xu et al., "Electrophore Mass Tag Dideoxy DNA Sequencing", Anal. Chem., vol. 69, pp. 3595-3602, 1997.

Steven P. Gygi et al., "Quantitative Analysis of Complex Protein Mixtures Using Isotope-Coded Affinity Tages", Nature Biotechnology, vol. 17, pp. 994-999, Oct. 1999.

Robert L. Geahlen et al., "A General Method for Preparation of Peptides Biotinylated at the Carboxy Terminus", Analytical Biochemistry, vol. 202, pp. 68-70, 1992.

David G. Sawutz et al, "Synthesis and Molecular Characterization of a Biotinylated Analog of [LYS]Bradykinin", Peptides, vol. 12, pp. 1019-1024, 1991.

Sesha Natarajan et al., "Site-Specific Biotinylation; A Novel Approach and is Application to Endothelin-1 Analogs and PTH-Analog", Int. J. Peptide Protein Res., vol. 40, pp. 567-574, 1992.

Mark L. Stolowitz et al., :"Phenylboronic Acid-Salicylhydroxamic Acid Bioconjugates. 1. A Novel Boronic Acid Complex for Protein Immobilization", Bioconjugate Chem., vol. 12, pp. 229-239, 2001.

Jean P. Wiley et al., "Phenylboronic Acid-Salicylhydroxamic Acid Bioconjugates. 2. Polyvalent Immobilization of Protein Ligands for Affinity Chromatography", Bioconjugate Chem., vol. 12, pp. 240-250, 2001.

T. Keough et al., "Atmospheric Pressure Matrix-Assisted Laser Desorption/Ionization Ion Trap Mass Spectrometry of Sulfonic Acid Derivatized Tryptic Peptides", Rapid Comminications in Mass Spectrometry, vol. 15, pp. 2227-2239, 2001.

Scot R. Weinberger et al., "Recent Trends in Protein Biochip Technology", Pharmacogenomics, vol. 1, No. 4, pp. 395-416, 2000.

Gregg B. Fields et al., "Solid Phase Peptide Synthesis Utilizing 9-Fluorenylmethoxycarbonyl Amino Acids", Int. J. Peptide Protein Res., vol. 35, pp. 161-214, 1990.

Karl R. Clauser et al., "Role of Accurate Mass Measurement (±10 PPM) in Protein Identification Strategies Employing MS or MS/MS and Database Searching", Anal. Chem, vol. 71, pp. 2871-2882, 1999.

Youling Wu et al., "An Efficient Method for the Preparation of $\omega,\omega'$-Bis-Urethane Protected Arginine Derivatives", Synthetic Communications, vol. 23, No. 21, pp. 3055-3060, 1993.

Shufang Niu et al., "Direct Comparison of Infrared and Ultraviolet Wavelength Matrix-Assisted Laser Desorption/Ionization Mass Spectrometry of Proteins", American Society for Mass Spectrometry, vol. 9, pp. 1-7, 1998.

* cited by examiner

Fig.1.
Synthesis of 2-Cyan-3-(4-tert-butoxycarbonyloxyphenyl) acrylic acid-N-(hydroxysuccinimidester) [NHS-HCCA]:
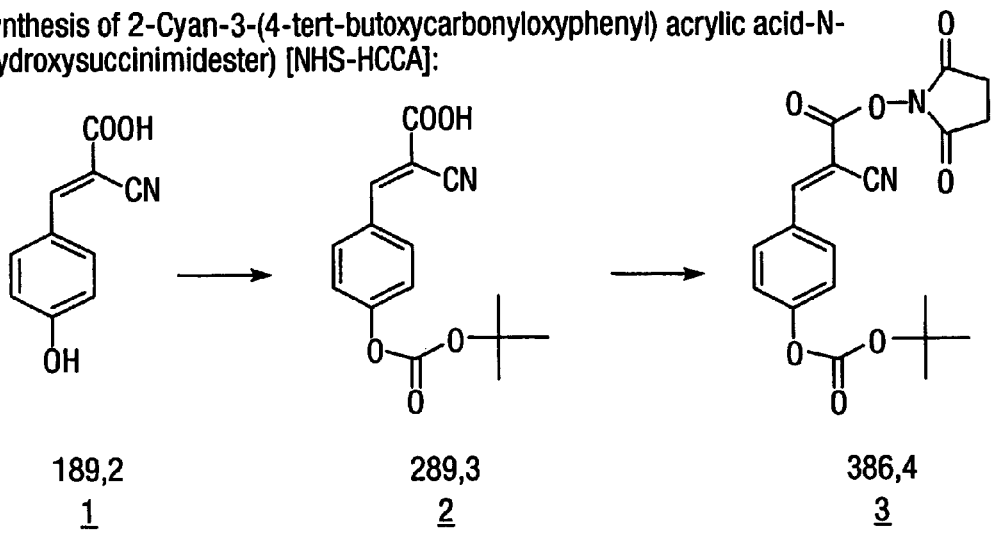
189,2
1
289,3
2
386,4
3
Synthesis of 2-Cyan-3-(4-tert-hydroxyphenyl) acrylic acid-6-[(2,5-dioxo-1-pyrrolidinyl) oxy)-(6-oxo) hexyl] amide [NHS-L-HCCA]:
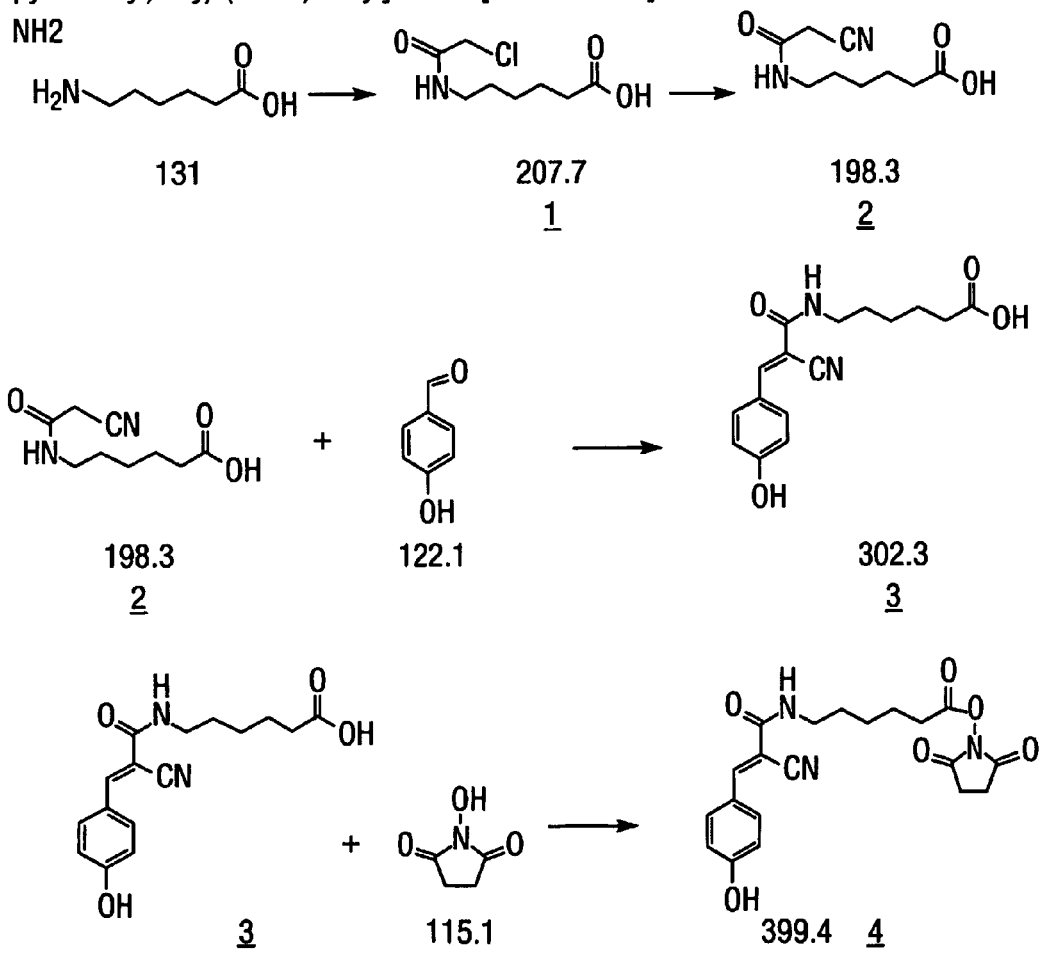
131
207.7
1
198.3
2
198.3
2
122.1
302.3
3
3
115.1
399.4  4

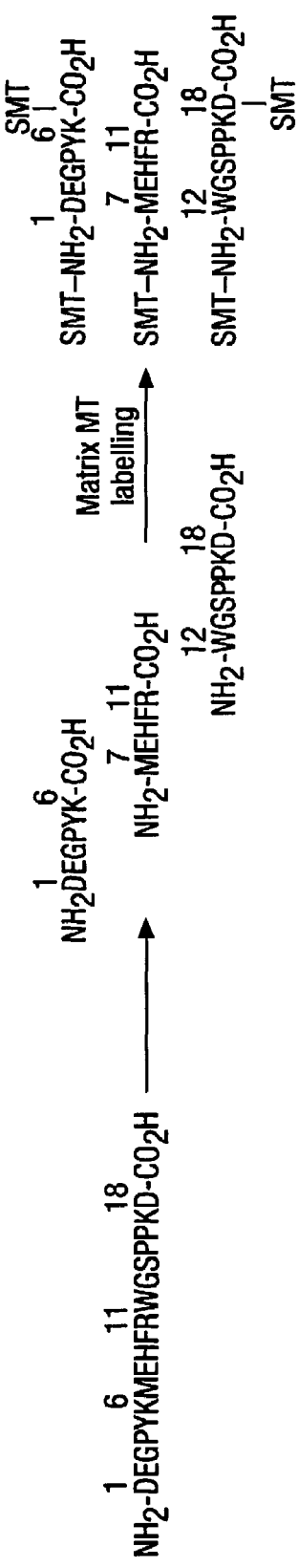
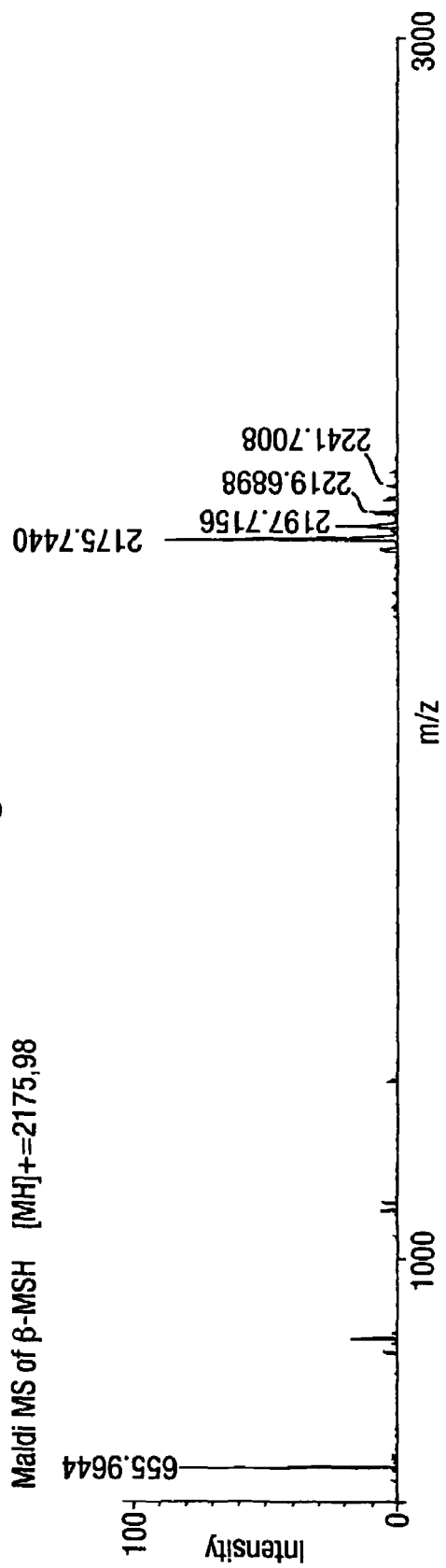

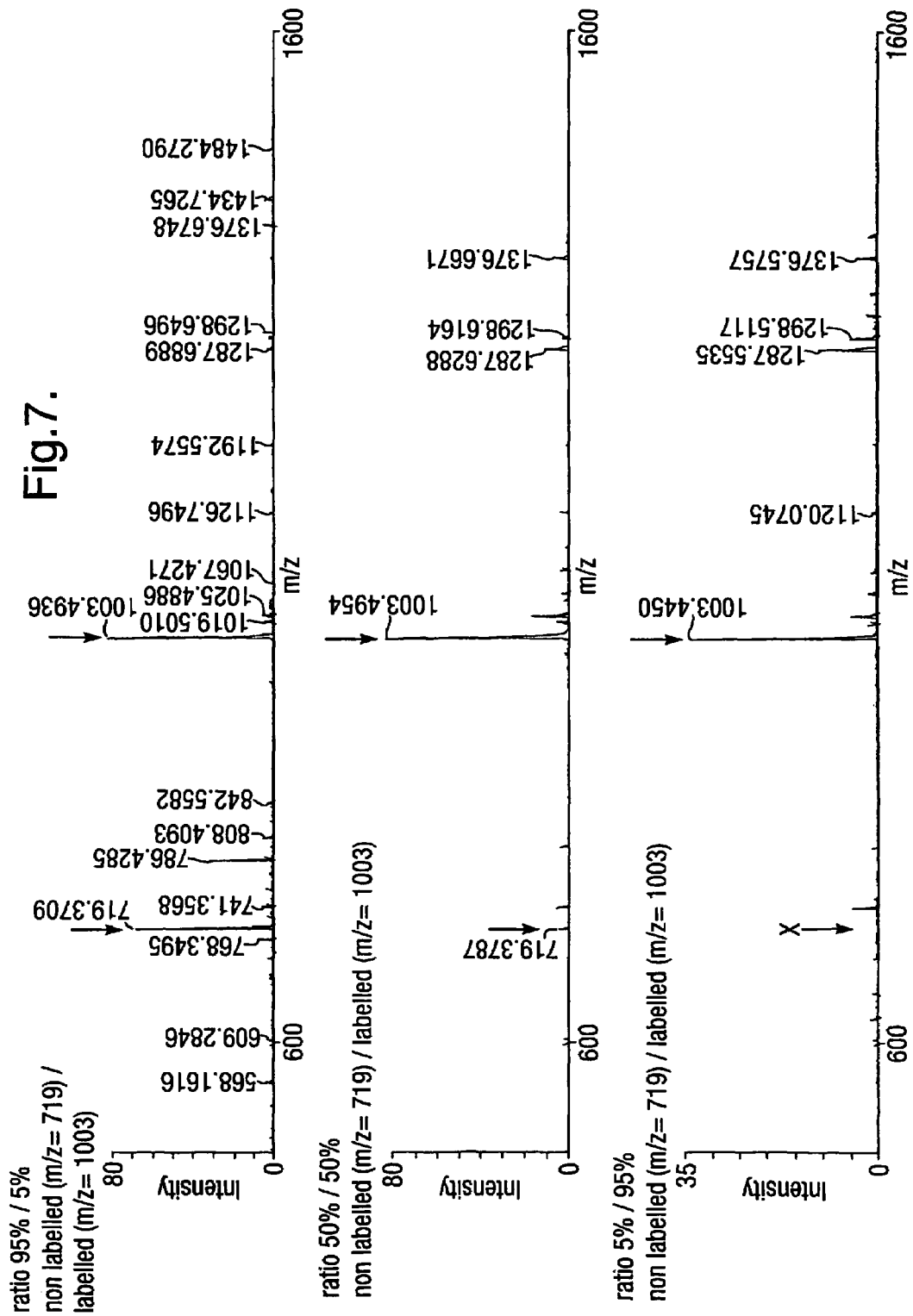

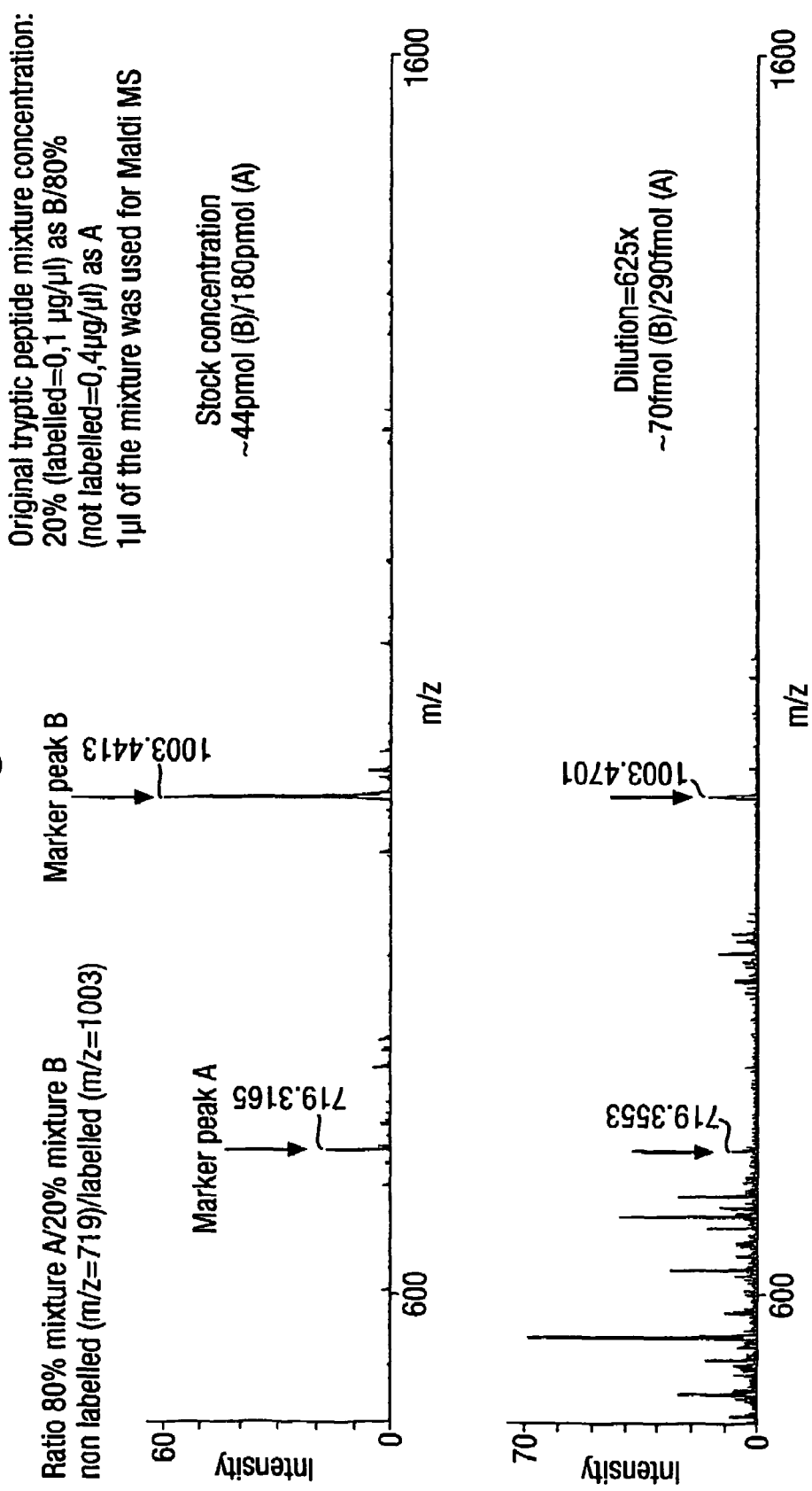

Fig. 10.

15/42 matches (35%). 69293.9 Da, pI=5.82. Acc. # swiss:P02769. BOVIN. SERUM ALBUMIN PRECURSOR..

| m/z submitted | MH+ matched | Δppm | start | end | Peptide Sequence | Modifications |
|---|---|---|---|---|---|---|
| 927.4680 | 927.4940 | -28.0249 | 161 | 167 | (K)YLYEIAR (R) | |
| 1163.6069 | 1163.6312 | -20.8956 | 66 | 75 | (K)LVNELTEFAK (T) | |
| 1249.6052 | 1249.6217 | -13.2142 | 35 | 44 | (R)FKDLGEEHFK (G) | |
| 1283.6973 | 1283.7112 | -10.8252 | 361 | 371 | (R)HPEYAVSVLLR (L) | |
| 1305.6960 | 1305.7167 | -15.8348 | 402 | 412 | (K)HLVDEPQNLIK (Q) | |
| 1439.8041 | 1439.8123 | -5.7004 | 360 | 371 | (R)RHPEYAVSVLLR (L) | |
| 1479.7880 | 1479.7960 | -5.3985 | 421 | 433 | (K)LGEYGFQNALIVR (Y) | |
| 1567.7394 | 1567.7433 | -2.4778 | 347 | 359 | (K)DAFLGSFLYEYSR (R) | |
| 1639.9368 | 1639.9383 | -0.9122 | 437 | 451 | (R)KVPQVSTPTLVEVSR (S) | |
| 1667.8214 | 1667.8137 | 4.6234 | 469 | 482 | (R)MPCTEDYLSLILNR (L) | |
| 1823.9162 | 1823.9002 | 8.7746 | 508 | 523 | (R)RPCFSALTPDETYVPK (A) | |
| 1888.9371 | 1888.9274 | 5.1368 | 169 | 183 | (R)HPYFYAPELLYYANK (Y) | |
| 2045.0368 | 2045.0285 | 4.0547 | 168 | 183 | (R)RHPYFYAPELLYYANK (Y) | |
| 2506.2639 | 2506.2508 | 5.2276 | 469 | 489 | (R)MPCTEDYLSLILNRLCVLHEK (T) | 1Met-ox |
| 3395.6670 | 3395.6438 | 6.8340 | 558 | 587 | (K)HKPKATEEQLKTVMENFVAFVDKCCAADDK (E) | |

The matched peptides cover 28% (174/607 AA's) of the protein

Fig. 12.

16/50 matches (32%). 69293.9 Da, pI = 5.82. Acc. # swiss: P02769. BOVIN. SERUM ALBUMIN PRECURSOR.

| m/z submitted | MH+ matched | Δ ppm | start | end | Peptide Sequence | Modifications |
|---|---|---|---|---|---|---|
| 829.4550 | 829.4572 | -2.6686 | 101 | 105 | (K) VASLR (E) | 1SMT |
| 933.4466 | 933.4504 | -4.0854 | 205 | 209 | (K) IETMR (E) | 1SMT |
| 933.4466 | 933.4504 | -4.0854 | 223 | 228 | (R) CASIQK (F) | 1SMT |
| 973.4883 | 973.4896 | -1.3110 | 236 | 241 | (K) AWSVAR (L) | 1SMT |
| 996.4857 | 996.4903 | -4.6207 | 29 | 34 | (K) SEIAHR (F) | 1SMT |
| 1068.4785 | 1068.4791 | -0.5345 | 25 | 28 | (R) DTHK (S) | 1SMT |
| 1211.6119 | 1211.6101 | 1.4977 | 161 | 167 | (K) YLYEIAR (R) | 1SMT |
| 1217.5769 | 1217.5665 | 8.5367 | 223 | 228 | (R) CASIQK (F) | 2SMT |
| 1233.5978 | 1233.6097 | -9.6395 | 156 | 160 | (K) KFWGK (Y) | 2SMT |
| 1308.5650 | 1308.5717 | -5.0955 | 499 | 507 | (K) CCTESLVNR (R) | 1SMT |
| 1567.8258 | 1567.8273 | -0.9497 | 361 | 371 | (R) HPEYAVSVLLR (L) | 1SMT |
| 1569.8294 | 1569.8218 | 4.8352 | 233 | 241 | (R) ALKAWSVAR (L) | 2SMT |
| 1723.9240 | 1723.9284 | -2.5523 | 360 | 371 | (R) RHPEYAVSVLLR (L) | 1SMT |
| 1763.9128 | 1763.9121 | 0.4075 | 421 | 433 | (K) LGEYGFQNALIVR (Y) | 1SMT |
| 1795.9618 | 1795.9594 | 1.3222 | 438 | 451 | (K) VPQVSTPTLVEVSR (S) | 1SMT |
| 1851.8737 | 1851.8594 | 7.7344 | 347 | 359 | (K) DAFLGSFLYEYSR (R) | 1SMT |
| 2208.1692 | 2208.1705 | -0.5801 | 437 | 451 | (R) KVPQVSTPTLVEVSR (S) | 2SMT |

The matched peptides cover 17% (109/607 AA's) of the protein

Fig. 14.

7/56 matches (12%). 35691.1 Da, pI=8.52. Acc. # swiss:P46406. RABIT. GLYCERALDEHYDE 3-PHOSPHATE DEHYDROGENASE (EC 1.2.1.12) (GAPDH)..

| m/z submitted | MH+ matched | Δppm | start | end | Peptide Sequence | Modifications |
|---|---|---|---|---|---|---|
| 977.5324 | 977.5420 | -9.8265 | 70 | 77 | (K)AIITFQER (D) | |
| 1499.7853 | 1499.7892 | -2.5929 | 232 | 245 | (R)VPTPNVSVVDLTCR (L) | |
| 1615.8755 | 1615.8808 | -3.2682 | 70 | 83 | (K)AIITFQERDPANIK (W) | |
| 1763.8175 | 1763.8029 | 8.2636 | 307 | 320 | (K)LISWYDNEFGYSNR (V) | |
| 2618.3883 | 2618.3765 | 4.5189 | 160 | 183 | (K)VIHDHFGIVEGLMTTVHAITATQK (T) | |
| 3317.5310 | 3317.5651 | -10.2886 | 25 | 52 | (K)VDVVAINDPFIDLHYMVYMFQYDSTHGK (F) | 1Met-ox |
| 3339.6063 | 3339.6432 | -11.0492 | 84 | 115 | (K)WGDAGAEYVVESTGVFTTMEKAGAHLKGGAKR (V) | |

The matched peptides cover 37% (126/332 AA's) of the protein

Fig. 16.

9/52 matches (17%). 35691.1 Da, pI=8.52. Acc. # swiss:P46406. RABIT. GLYCERALDEHYDE 3-PHOSPHATE DEHYDROGENASE (EC 1.2.1.12) (GAPDH)..

| m/z submitted | MH+ matched | Δppm | start | end | Peptide Sequence | Modifications |
|---|---|---|---|---|---|---|
| 1056.5512 | 1056.5267 | 23.1986 | 111 | 115 | (K)GGAKR(V) | 2SMT |
| 1079.5357 | 1079.5348 | 0.8227 | 225 | 231 | (K)LTGMAFR (V) | 1SMT |
| 1089.5473 | 1089.5482 | -0.7836 | 3 | 10 | (K)VGVNGFGR (I) | 1SMT |
| 1164.5842 | 1164.5842 | -0.0042 | 105 | 110 | (K)AGAHLK(G) | 2SMT |
| 1261.6667 | 1261.6581 | 6.8178 | 70 | 77 | (K)AITIFQER (D) | 1SMT |
| 1783.9148 | 1783.8808 | 19.0702 | 184 | 194 | (K)TVDGPSGKLWR(D) | 2SMT |
| 1783.9148 | 1783.9053 | 5.3359 | 232 | 245 | (R)VPTPNVSVVDLTCR (L) | 1SMT |
| 1960.0024 | 1959.9897 | 6.4986 | 252 | 260 | (K)YDDIKKVVK(Q) | 3SMT |
| 1981.9910 | 1982.0096 | -9.3660 | 195 | 212 | (R)DGRGAAQNIIPASTGAAK (A) | 1SMT |
| 2047.9688 | 2047.9190 | 24.3090 | 307 | 320 | (K)LISWYDNEFGYSNR (V) | 1SMT |

The matched peptides cover 30% (100/332 AA's) of the protein

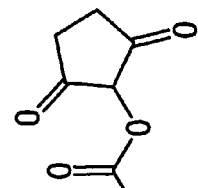
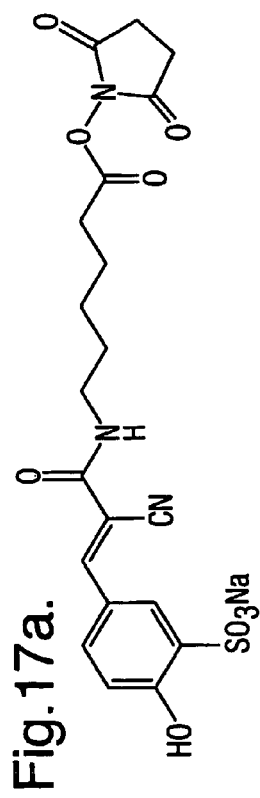
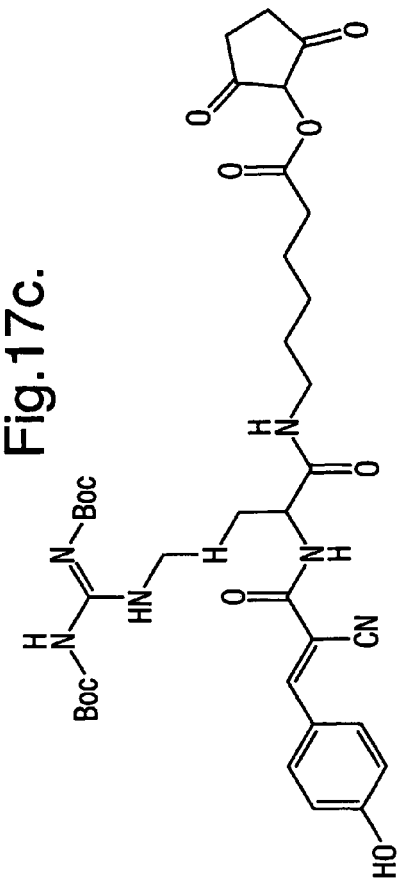
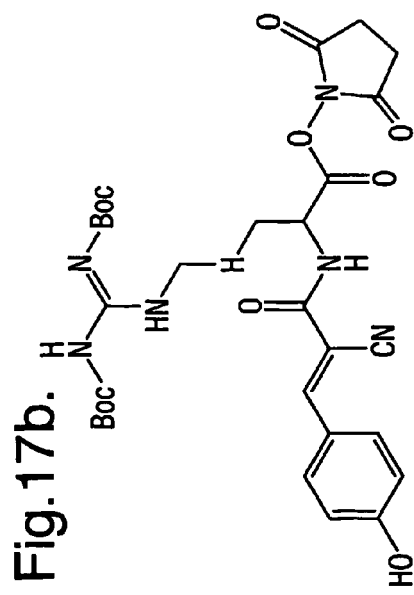
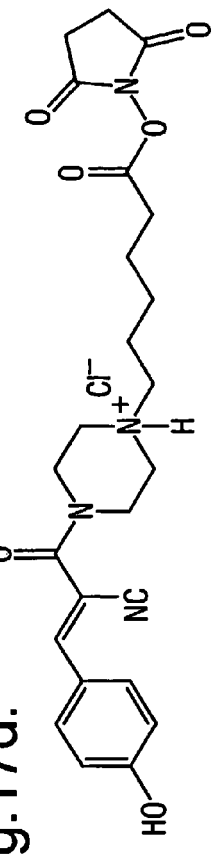
Fig. 17a. Fig. 17b. Fig. 17c. Fig. 17d.

(a) HO-Su, DCC, CH$_2$Cl$_2$, 6-Amino-hexanoic acid; (b) HO-Su, DCC, CH$_2$Cl$_2$

SEQUENCE LISTING

<160> NUMBER OF SEQ ID NOS: 58

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:labelled peptide

<400> SEQUENCE: 1

His Arg Asp Pro Tyr Arg Phe Asp Pro His Lys Asp
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence:labelled peptide

<400> SEQUENCE: 2

His Ser Arg Gly Ala Arg Gly His Ser His Ala His Arg Gly
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:labelled peptide

<400> SEQUENCE: 3

Tyr Asp Ser Gly Glu Gly Asp Glu Ser Asp Ala Tyr Glu Gly
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence:labelled peptide

<400> SEQUENCE: 4

Leu Gly Trp Ser Gly Phe Gly Trp Ser Phe Ser Tyr Leu Gly
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:labelled peptide

<400> SEQUENCE: 5

Asp Glu Gly Pro Tyr Lys Met Glu His Phe Arg Trp Gly Ser Pro Pro
 1               5                  10                  15

Lys Asp

<210> SEQ ID NO 6
<211> LENGTH: 6

```
<212> TYPE: PRT
<213> ORGANISM: Artificial Sequence
<220> FEATURE:
<223> OTHER INFORMATION: Description of Artificial Sequence:labelled
      peptide

<400> SEQUENCE: 6

Asp Glu Gly Pro Tyr Lys
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:labelled
      peptide

<400> SEQUENCE: 7

Met Glu His Phe Arg
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:labelled
      peptide

<400> SEQUENCE: 8

Trp Gly Ser Pro Pro Lys Asp
  1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence:labelled
      peptide

<400> SEQUENCE: 9

His Ser Arg Gly His Arg Gly His Ser His Ala His Arg Gly
  1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:labelled
      peptide

<400> SEQUENCE: 10

Lys Tyr Leu Tyr Glu Ile Ala Arg Arg
  1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:labelled
      peptide

<400> SEQUENCE: 11

Lys Leu Val Asn Glu Leu Thr Glu Phe Ala Lys Thr
```

```
                           1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence:labelled
      peptide

<400> SEQUENCE: 12

Arg Phe Lys Asp Leu Gly Glu Glu His Phe Lys Gly
 1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:labelled
      peptide

<400> SEQUENCE: 13

Arg His Pro Glu Tyr Ala Val Ser Val Leu Leu Arg Leu
 1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:labelled
      peptide

<400> SEQUENCE: 14

Lys His Leu Val Asp Glu Pro Gln Asn Leu Ile Lys Gln
 1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence:labelled
      peptide

<400> SEQUENCE: 15

Arg Arg His Pro Glu Tyr Ala Val Ser Val Leu Leu Arg Leu
 1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:labelled
      peptide

<400> SEQUENCE: 16

Lys Leu Gly Glu Tyr Gly Phe Gln Asn Ala Leu Ile Val Arg Tyr
 1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence:labelled
``` peptide

<400> SEQUENCE: 17

Lys Asp Ala Phe Leu Gly Ser Phe Leu Tyr Glu Tyr Ser Arg Arg
 1               5                  10                  15

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence:labelled
      peptide

<400> SEQUENCE: 18

Arg Lys Val Pro Gln Val Ser Thr Pro Thr Leu Val Glu Val Ser Arg
 1               5                  10                  15

Ser

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence:labelled
      peptide

<400> SEQUENCE: 19

Arg Met Pro Cys Thr Glu Asp Tyr Leu Ser Leu Ile Leu Asn Arg Leu
 1               5                  10                  15

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:labelled
      peptide

<400> SEQUENCE: 20

Arg Arg Pro Cys Phe Ser Ala Leu Thr Pro Asp Glu Thr Tyr Val Pro
 1               5                  10                  15

Lys Ala

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence:labelled
      peptide

<400> SEQUENCE: 21

Arg His Pro Tyr Phe Tyr Ala Pro Glu Leu Leu Tyr Tyr Ala Asn Lys
 1               5                  10                  15

Tyr

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence:labelled
      peptide

<400> SEQUENCE: 22

```
Arg Arg His Pro Tyr Phe Tyr Ala Pro Glu Leu Leu Tyr Tyr Ala Asn
  1               5                  10                  15

Lys Tyr

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence:labelled
      peptide

<400> SEQUENCE: 23

Arg Met Pro Cys Thr Glu Asp Tyr Leu Ser Leu Ile Leu Asn Arg Leu
  1               5                  10                  15

Cys Val Leu His Glu Lys Thr
                 20

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence:labelled
      peptide

<400> SEQUENCE: 24

Lys His Lys Pro Lys Ala Thr Glu Glu Gln Leu Lys Thr Val Met Glu
  1               5                  10                  15

Asn Phe Val Ala Phe Val Asp Lys Cys Cys Ala Ala Asp Asp Lys Glu
                 20                  25                  30

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:labelled
      peptide

<400> SEQUENCE: 25

Lys Val Ala Ser Leu Arg Glu
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:labelled
      peptide

<400> SEQUENCE: 26

Lys Ile Glu Thr Met Arg Glu
  1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:labelled
      peptide

<400> SEQUENCE: 27
```

```
Arg Cys Ala Ser Ile Gln Lys Phe
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:labelled
      peptide

<400> SEQUENCE: 28

Lys Ala Trp Ser Val Ala Arg Leu
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:labelled
      peptide

<400> SEQUENCE: 29

Lys Ser Glu Ile Ala His Arg Phe
  1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:labelled
      peptide

<400> SEQUENCE: 30

Arg Asp Thr His Lys Ser
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:labelled
      peptide

<400> SEQUENCE: 31

Lys Tyr Leu Tyr Glu Ile Ala Arg Arg
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:labelled
      peptide

<400> SEQUENCE: 32

Arg Cys Ala Ser Ile Gln Lys Phe
  1               5

<210> SEQ ID NO 33
<211> LENGTH: 7
<212> TYPE: PRT
<213> ORGANISM: Artificial Sequence
<220> FEATURE:
```

<223> OTHER INFORMATION: Description of Artificial Sequence:labelled
      peptide

<400> SEQUENCE: 33

Lys Lys Phe Trp Gly Lys Tyr
  1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:labelled
      peptide

<400> SEQUENCE: 34

Lys Cys Cys Thr Glu Ser Leu Val Asn Arg Arg
  1               5                  10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:labelled
      peptide

<400> SEQUENCE: 35

Arg His Pro Glu Tyr Ala Val Ser Val Leu Leu Arg Leu
  1               5                  10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence:labelled
      peptide

<400> SEQUENCE: 36

Arg Ala Leu Lys Ala Trp Ser Val Ala Arg Leu
  1               5                  10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence:labelled
      peptide

<400> SEQUENCE: 37

Arg Arg His Pro Glu Tyr Ala Val Ser Val Leu Leu Arg Leu
  1               5                  10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence:labelled
      peptide

<400> SEQUENCE: 38

Lys Leu Gly Glu Tyr Gly Phe Gln Asn Ala Leu Ile Val Arg Tyr
  1               5                  10                  15

```
<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:labelled
      peptide

<400> SEQUENCE: 39

Lys Val Pro Gln Val Ser Thr Pro Thr Leu Val Glu Val Ser Arg Ser
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence:labelled
      peptide

<400> SEQUENCE: 40

Lys Asp Ala Phe Leu Gly Ser Phe Leu Tyr Glu Tyr Ser Arg Arg
 1               5                  10                  15

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence:labelled
      peptide

<400> SEQUENCE: 41

Arg Lys Val Pro Gln Val Ser Thr Pro Thr Leu Val Glu Val Ser Arg
 1               5                  10                  15

Ser

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence:labelled
      peptide

<400> SEQUENCE: 42

Lys Ala Ile Thr Ile Phe Gln Glu Arg Asp
 1               5                  10

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence:labelled
      peptide

<400> SEQUENCE: 43

Arg Val Pro Thr Pro Asn Val Ser Val Val Asp Leu Thr Cys Arg Leu
 1               5                  10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence:labelled
      peptide
```

<400> SEQUENCE: 44

Lys Ala Ile Thr Ile Phe Gln Glu Arg Asp Pro Ala Asn Ile Lys Trp
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence:labelled
      peptide

<400> SEQUENCE: 45

Lys Leu Ile Ser Trp Tyr Asp Asn Glu Phe Gly Tyr Ser Asn Arg Val
1               5                   10                  15

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence:labelled
      peptide

<400> SEQUENCE: 46

Lys Val Ile His Asp His Phe Gly Ile Val Glu Gly Leu Met Thr Thr
1               5                   10                  15

Val His Ala Ile Thr Ala Thr Gln Lys Thr
            20                  25

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence:labelled
      peptide

<400> SEQUENCE: 47

Lys Val Asp Val Val Ala Ile Asn Asp Pro Phe Ile Asp Leu His Tyr
1               5                   10                  15

Met Val Tyr Met Phe Gln Tyr Asp Ser Thr His Gly Lys Phe
            20                  25                  30

<210> SEQ ID NO 48
<211> LENGTH: 34
<212> TYPE: PRT
<213> ORGANISM: Artificial Sequence
<220> FEATURE:
<223> OTHER INFORMATION: Description of Artificial Sequence:labelled
      peptide

<400> SEQUENCE: 48

Lys Trp Gly Asp Ala Gly Ala Glu Tyr Val Val Glu Ser Thr Gly Val
1               5                   10                  15

Phe Thr Thr Met Glu Lys Ala Gly Ala His Leu Lys Gly Gly Ala Lys
            20                  25                  30

Arg Val

<210> SEQ ID NO 49
<211> LENGTH: 7
<212> TYPE: PRT
<213> ORGANISM: Artificial Sequence
<220> FEATURE:

-continued

<223> OTHER INFORMATION: Description of Artificial Sequence:labelled
      peptide

<400> SEQUENCE: 49

Lys Gly Gly Ala Lys Arg Val
 1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence:labelled
      peptide

<400> SEQUENCE: 50

Lys Leu Thr Gly Met Ala Phe Arg Val
 1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence:labelled
      peptide

<400> SEQUENCE: 51

Lys Val Gly Val Asn Gly Phe Gly Arg Ile
 1               5                  10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence:labelled
      peptide

<400> SEQUENCE: 52

Lys Ala Gly Ala His Leu Lys Gly
 1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence:labelled
      peptide

<400> SEQUENCE: 53

Lys Ala Ile Thr Ile Phe Gln Glu Arg Asp
 1               5                  10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence:labelled
      peptide

<400> SEQUENCE: 54

Lys Thr Val Asp Gly Pro Ser Gly Lys Leu Trp Arg Asp
 1               5                  10

```
<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence:labelled
      peptide

<400> SEQUENCE: 55

Arg Val Pro Thr Pro Asn Val Ser Val Val Asp Leu Thr Cys Arg Leu
 1               5                  10                  15

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence:labelled
      peptide

<400> SEQUENCE: 56

Lys Tyr Asp Asp Ile Lys Lys Val Val Lys Gln
 1               5                  10

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence:labelled
      peptide

<400> SEQUENCE: 57

Arg Asp Gly Arg Gly Ala Ala Gln Asn Ile Ile Pro Ala Ser Thr Gly
 1               5                  10                  15

Ala Ala Lys Ala
            20

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence:labelled
      peptide

<400> SEQUENCE: 58

Lys Leu Ile Ser Trp Tyr Asp Asn Glu Phe Gly Tyr Ser Asn Arg Val
 1               5                  10                  15
```

METHOD FOR CHARCTERISING ANALYTES

CROSS-REFERENCE TO PRIOR APPLICATION

This is a U.S. national phase application under 35 U.S.C. §371 of International Patent Application No. PCT/GB03/01485 filed Apr. 4, 2003, and claims the benefit of European Patent Application No. 02252440.9 filed Apr. 4, 2002 which is incorporated by reference herein. The International Application was published in English on Oct. 23, 2003 as WO 03/087839 A1 under PCT Article 21(2).

This invention relates to methods of labelling analyte molecules, particularly non-volatile biomolecules, with markers that enhance the sensitivity with which their associated analyte biomolecule is detectable by Matrix Assisted Laser Desorption Ionisation (MALDI) Mass Spectrometry. Specifically this invention relates to the ability of certain dyes to improve the sensitivity of detection by MALDI mass spectrometry of analytes labelled with these dyes.

The identification of proteins in biological samples is an essential activity of biochemical analysis, particularly the determination of the sequence of a protein, since the sequence determines the structure of a protein, which, in turn, determines the function of the protein. Traditional techniques for protein identification are cumbersome and relatively slow. The mainstay of protein identification techniques has been chemical sequencing of peptides using the Edman degradation, which can sequentially identify amino acids in a peptide from the N-terminus. This sequencing technique is typically used in conjunction with enzymatic digestion of a protein or polypeptide. Typically, an unidentified polypeptide is digested and its component peptides are separated from each other by chromatography. The individual peptides are then subjected to Edman degradation. The sequences of the peptides can be ordered by comparing the sequences of peptides from digestion of the polypeptide with different sequence specific cleavage reagents. This process allows the complete sequence of a polypeptide to be determined. While this has been a highly successful technique for the identification of proteins, it is quite laborious. New technologies have, made rapid protein identification more feasible such as Matrix Assisted Laser Desorption Ionisation Time-of-Flight (MALDI-TOF) mass spectrometry, which has permitted the development of peptide mass fingerprinting as a relatively rapid procedure for protein identification.

A typical peptide mass fingerprinting protocol involves determining the mass of the unidentified protein followed by digestion of the protein (in gel or in solution) with enzymes such as trypsin. Trypsin cleaves polypeptides selectively at arginine and lysine residues, leaving either arginine or lysine at the C-termini of the product peptides. The positions of lysine and arginine in the sequence of a polypeptide determine where the polypeptide is cut giving rise to a characteristic series of peptides. The pattern of peptides can be easily detected by MALDI-TOF mass spectrometry. This mass spectrometric technique has a large mass range, can readily ionise large biomolecules, will preferentially produce singly charged ions and competition for ionisation with this technique is not severe, although competition can be problematic. This means that there is generally one peak in the mass spectrum for each peptide, the mass-to-charge ratio for each peak has essentially the same value as the mass of the peptide, with an added proton to ionise the peptide, and most (and sometimes all) the peptides from the tryptic digest of an unidentified protein can be analysed simultaneously. In effect the mass spectrum is a 'bar-code' in which the lines in the spectrum represent the masses of the characteristic cleavage peptides of the protein. For any given protein, there may be some peptides, which have the same mass as a peptide from another protein but it is very unlikely that two different proteins will give rise to peptides that all have identical masses. This means that the pattern of masses of the tryptic digest of a protein is a fairly unique identifier of that protein and is called a Peptide Mass Fingerprint (PMF). The relative uniqueness of PMFs means that databases of calculated (or theoretical) PMFs, determined from known protein sequences or sequences that have been predicted from genomic DNA or expressed sequence tags (ESTs), can be used to identify proteins in biological samples (Pappin D J C, Höjrup P and Bleasby A J, Current Biology 3: 327-332, "Rapid identification of proteins by peptide-mass fingerprinting." 1993; Mann M, Hojrup P, Roepstorff P, Biol Mass Spectrom 22(6): 338-345, "Use of mass spectrometric molecular weight information to identify proteins in sequence databases." 1993; Yates J R 3rd, Speicher S, Griffin P R, Hunkapiller T, Anal Biochem 214(2): 397-408, "Peptide mass maps: a highly informative approach to protein identification." 1993). The PMF for an unidentified protein can be compared with all of the PMFs in a database to find the best match, thereby identifying the protein. Searches of this kind can be constrained by determining the mass of the protein prior to digestion. In this way the pattern of masses of an unidentified polypeptide can be related to its sequence, which in turn can help to determine the role of a protein in a particular sample.

There are, however, many technical difficulties involved in determining the PMF for a protein. A typical protein will give rise to twenty to thirty peptides after cleavage with trypsin, but not all of these peptides will appear in the mass spectrum. The precise reasons for this are not fully understood. One factor that is believed to cause incomplete spectra is competition for protonation during the ionisation process, resulting in preferential ionisation of arginine containing peptides (Krause E. & Wenschuh H. & Jungblut P. R., Anal Chem 71(19): 4160-4165, "The dominance of arginine-containing peptides in MALDI-derived tryptic mass fingerprints of proteins." 1999). In addition, there are surface effects that result from the process of preparing MALDI targets. The targets are prepared by dissolving the peptide digest in a solution of the matrix material. Small droplets of the peptide/matrix solution are dropped onto a metal target and left to dry. Differences in solubility of peptides will mean that some peptides will preferentially crystallise near the top surface of the matrix where they will be desorbed more readily.

Sensitivity is also a problem with conventional protocols for identifying proteins from their PMF. To be an effective tool, it should be possible to determine a PMF for as small a sample of protein as possible to improve the sensitivity of the analysis of protein samples.

Some attempts have been made to improve the ionisation of peptides that do not contain arginine by chemical derivatisation of peptides. Conversion of lysine to homo-arginine is one approach that has met with some success (V. Bonetto et al., Journal of Protein Chemistry 16(5): 371-374, "C-terminal Sequence Determination of Modified Peptides by MALDI MS", 1997; Francesco L. Brancia, Stephen G. Oliver and Simon J. Gaskell, Rapid Commun. in Mass Spec., 14, 2070-2073, "Improved matrix-assisted laser desorption/ionisation mass spectrometric analysis of tryptic hydrolysates of proteins following guanidination of lysine-containing peptides." 2000; Brancia et al., Electrophoresis 22: 552-559, "A combination of chemical derivatisation and improved bioinformatics tools optimises protein identification for proteomics", 2001). The conversion of lysine to homo-arginine introduces guanidino functionalities into all of the peptides from a tryptic digest, with the exception of C-terminal peptides, greatly improving the representation of lysine containing peptides in the MALDI-TOF mass spectra.

The derivatisation of peptides to introduce guanidino-groups is a method of improving the proton affinity of the derivatised peptide. This approach to improve sensitivity has been moderately successful in enhancing the sensitivity of detection in techniques that depend on protonation to achieve ionisation such as electrospray ionisation (ESI) and MALDI analysis. These techniques are most effective if the analyte does not already possess a functionality with a high proton affinity, e.g. oligosaccharides (Okamoto et al., Anal Chem. 69(15): 2919-2926, "High-sensitivity detection and post-source decay of 2-aminopyridine-derivatized oligosaccharides with matrix-assisted laser desorption/ionisation mass spectrometry." 1997). However, analytes that already contain functionalities that are readily protonated, such as trypsin digested peptides, do not benefit significantly from such reagents and other methods to improve the sensitivity of these sorts of analyte are needed.

Various other reagents for derivatising peptides have also been developed. Reagents that introduce quaternary ammonium functionalities and quaternary phosphonium functionalities have been developed for positive ion mass spectrometry. Halogenated compounds, particularly halogenated aromatic compounds are well known electrophores, i.e. they pick up thermal electrons very easily. A variety of derivatisation reagents based on fluorinated aromatic compounds (Bian N. et al., Rapid Commun Mass Spectrom 11(16): 1781-1784, "Detection via laser desorption and mass spectrometry of multiplex electrophore-labelled albumin." 1997) have been developed for electron capture detection, which is a highly sensitive ionisation and detection process that can be used with negative ion mass spectrometry (Abdel-Baky S. & Giese R. W., Anal Chem 63(24):2986-2989, "Gas chromatography/electron capture negative-ion mass spectrometry at the zeptomole level." 1991). A fluorinated aromatic group could also be used as a sensitivity-enhancing group. Aromatic sulphonic acids have also been used for improving sensitivity in negative ion mass spectrometry.

Each type of derivatisation reagent that has been disclosed in the prior art has different benefits and limitations, which depend on the method of ionisation used and on the methods of mass analysis used (for a review see Roth et al., Mass Spectrometry Reviews 17:255-274, "Charge derivatisation of peptides for analysis by mass spectrometry", 1998). The mechanism by which sensitivity is enhanced may also be different for each type of group. Some derivatisation methods increase basicity and thus promote protonation and charge localisation, which improves sensitivity in surface desorption techniques like Matrix Assisted Laser Desorption ionisation (MALDI) and Fast Atom Bombardment (FAB). So far, reagents that introduce charge-carrying functionalities or functionalities with high proton affinities have been developed for MALDI mass spectrometry but no reagents that improve the desorption of the analyte by increasing its ability to absorb light and to mix with the matrix have been reported.

Negative ion mass spectrometry is sometimes more sensitive because there is less background noise. A tag that can enhance both negative ion mode detection and positive ion mode detection would have significant advantages. A tag for uniformly improving sensitivity of all associated analytes has yet to be found for all mass spectrometry techniques and it is unlikely that a universal reagent will be found. However, for specific mass spectrometric techniques it should be possible to design reagents that take advantage of features of a particular technique to promote detection sensitivity.

In this invention, derivatisation reagents and methods for their use have been developed to enhance the sensitivity of detection by MALDI mass spectrometry and it is anticipated that the reagents should be effective for most analytes that may be detected by this technique. This technique even enhances detection of peptides that contain easily protonated functionalities such as amino and guanidino groups. The inventors have observed that coupling a MALDI matrix dye directly to a biomolecule such as a peptide prior to embedding that peptide in the free matrix will greatly enhance the sensitivity with which the peptide can be detected.

WO98/31830 describes arrays of cleavable labels that are detectable by mass spectrometry which identify the sequence of a covalently linked nucleic acid probe. These mass labels have a number of advantages over other methods of analysing nucleic acids. At present commercially favoured systems are based on fluorescent labelling of DNA. Fluorescent labelling schemes permit the labelling of a relatively small number of molecules simultaneously, typically 4 labels can be used simultaneously and possibly up to eight. However the costs of the detection apparatus and the difficulties of analysing the resultant signals limit the number of labels that can be used simultaneously in a fluorescence detection scheme. An advantage of using mass labels is the possibility of generating large numbers of labels which have discrete peaks in a mass spectrum allowing similar numbers of distinct molecular species to be labelled simultaneously. Fluorescent dyes are expensive to synthesize whereas mass labels can comprise relatively simple polymers permitting combinatorial synthesis of large numbers of labels at low cost. This application describes the use of mass-modified MALDI matrix molecules for the labelling of biomolecules. Tags comprising MALDI matrix agents such as cinnamic and sinapinic acid can be attached to biomolecules through a photocleavable linker allowing cleavage and desorption of tags within a laser desorption ionisation mass spectrometer without requiring additional matrix.

WO99/60007 discloses mass tags comprising trityl functionalities for the labelling of nucleic acids and oligonucleotides. These tags can be cleaved from their associated oligonucleotides by photolysis in a MALDI-TOF mass spectrometer prior to desorption. The cleavage product is charged which is advantageous as it improves the sensitivity of the detection of the tags. This method also does not require additional matrix.

The prior art therefore discloses methods and reagents for cleavable tags for use in MALDI mass spectrometry that may be desorbed without additional matrix. The present invention is distinguished by the fact that the tags are not cleaved from the analyte and that the tags are used in the presence of free matrix material. The absence of free matrix material is detrimental to the present invention.

It is an object of this invention to overcome the problems associated with the above prior art. In particular, it is an aim of this invention to provide methods and labels that can be used to produce improved peptide mass fingerprints and which will improve the sensitivity of detection of other labelled non-volatile macromolecules particularly other biomolecules such as nucleic acids.

It is a further object of this invention to provide compounds which have desirable features as mass labels, and methods for the use of those compounds to provide improved mass spectra of associated analytes.

Accordingly, the present invention provides a method for characterising an analyte by matrix assisted laser desorption ionisation (MALDI) mass spectrometry, which method comprises:
- (a) labelling the analyte with a light-absorbing label that absorbs light at a pre-determined frequency, to form a labelled analyte;
- (b) embedding the labelled analyte in a matrix formed from at least one compound that absorbs light, to form an embedded labelled analyte;
- (c) desorbing the embedded labelled analyte by exposing it to light having the pre-determined frequency, to form a desorbed analyte; and
- (d) detecting the desorbed analyte by mass spectrometry to characterise the analyte.

Thus, the presence of a light-absorbing label attached to the analyte causes the labelled analyte molecule to absorb energy, which in turn aids in energising the analyte to bring it into the gaseous phase where it can be detected by the mass spectrometer. Generally the substance or compound forming the matrix will also absorb the light and be brought into the gas phase at the same time as the analyte. Thus, it is advantageous in the present invention, if the light-absorbing label and/or the compound forming the matrix are rapidly desorbed on the application of light.

The advantage of the methods, (and the compounds and kits) of the present invention is that they contribute to improving sensitivity, and can increase the number of peptides (e.g. small peptides, which are not detectable in conventional MALDI experiments) that are detected from a protein. In addition, through the use of appropriate tags, it is possible with this invention to analyse multiple samples simultaneously and it is also possible to determine the ratios of corresponding peptides in the different samples. With appropriate labelling procedures, it is also possible facilitate the conditioning of polypeptide sample for detection by mass spectrometry.

In a preferred embodiment, the desorbed analyte is directly detected by mass spectrometry. In the context of the present invention, this means that it is the analyte itself that is detected by mass spectrometry, rather than some other moiety such as a mass label which is only relatable to the analyte. This embodiment is particularly preferred when one or more peptide mass fingerprints (PMFs) are being produced to characterise a protein, or a population o0f proteins.

Alternatively the desorbed analyte may be indirectly detected by mass spectrometry. In this embodiment the analyte is additionally labelled with a mass label relatable to the analyte. The mass label is preferably cleaved from the desorbed analyte before being fed into the mass spectrometer. The analyte is characterised by detecting the mass label and relating it to the analyte.

In the present invention, the light employed is not especially limited, provided that it is able to sufficiently excite the light-absorbing label and thus the analyte. Typically the light to which the embedded labelled analyte is exposed is a laser light. The frequency of the light is also not especially limited, and UW, visible or infrared light may be employed.

It is particularly preferred that the compound forming the matrix absorbs light at the same frequency as the light-absorbing label. This is efficient, since a single light source can be employed in the apparatus. One way of achieving this is to ensure that the matrix and the light-absorbing label are formed from the same compound. This is a preferred way of practising the present invention. In this respect the final light-absorbing label and matrix-forming compound need not be identical (they cannot be, since one is attached chemically to the analyte) but should instead be substantially the same, or should comprise the same or similar groups such that they absorb light at the same, or substantially the same, wavelengths.

It is preferred that the light-absorbing label is formed from a dye, such as a non-fluorescent dye. The advantage of a non-fluorescent dye is that the energy absorbed is retained in the molecule to aid in the dissipation into the gas phase, rather than lost by re-emitance as fluorescence.

In the present invention, the analyte is not especially limited, and the invention may be employed to characterise any analyte. However, it is particularly well suited to biomolecules, such as proteins, polypeptides, peptides, peptide fragments and amino acids.

The methods of the present invention are useful in producing a PMF from a protein or polypeptide. Accordingly, the present invention also provides a method for characterising a polypeptide, which method comprises the steps of:
- (a) optionally reducing cysteine disulphide bridges in the polypeptide to form free thiols, and capping the free thiols;
- (b) cleaving the polypeptide with a sequence specific cleavage reagent to form peptide fragments;
- (c) optionally deactivating the cleavage reagent;
- (d) capping one or more ϵ-amino groups that are present with a lysine reactive agent;
- (e) analysing peptide fragments according to a method as defined above to form a mass fingerprint for the polypeptide; and
- (f) determining the identity of the polypeptide from the mass fingerprint.

When a population of proteins or polypeptides is to be investigated, the present invention can also be employed. In this respect, the present invention also provides a method for characterising a population of polypeptides, which method comprises the steps of:
- (a) optionally reducing cysteine disulphide bridges in one or more polypeptides to form free thiols, and capping the free thiols;
- (b) separating one or more polypeptides from the population;
- (c) cleaving one or more polypeptides with a sequence specific cleavage reagent to form peptide fragments;
- (d) optionally deactivating the cleavage reagent;
- (e) capping one or more ϵ-amino groups that are present with a lysine reactive agent;
- (f) analysing peptide fragments according to a method as defined above to form a mass fingerprint for one or more polypeptides; and
- (g) determining the identity of one or more polypeptides from the mass fingerprint.

The present invention can also be used to compare a number of protein or polypeptide samples. Thus, the present invention further provides a method for comparing a plurality of samples, each sample comprising one or more polypeptides, which method comprises the steps of:
- (a) optionally reducing cysteine disulphide bridges and capping the free thiols in one or more polypeptides from the samples;
- (b) separating one or more polypeptides from each of the samples;
- (c) cleaving the polypeptides with a sequence specific cleavage reagent to form peptide fragments;
- (d) optionally deactivating the cleavage reagent;
- (e) capping one or more ϵ-amino groups that are present with a lysine reactive agent;

(f) analysing peptide fragments according to a method as defined above to form a mass fingerprint for one or more polypeptides from the samples; and (g) determining the identity of one or more polypeptides in the samples from one or more mass fingerprints.

In the latter three aspects of the present invention it is preferred that the lysine-reactive agent is a labelled lysine-reactive agent. The label can be employed to distinguish which proteins or polypeptides originate from which samples, so that the samples can be pooled for analysis where appropriate.

In these aspects of the present invention, the sequence specific cleavage agent cleaves the one or more polypeptides on the C-terminal side of a lysine residue. Preferably the specific cleavage reagent comprises Lys-C or Trypsin. It is also preferred that the peptide fragments having capped F-amino groups are removed by affinity capture. This can be achieved by ensuring that the lysine reactive agent comprises biotin.

The most preferred lysine reactive agent for use in the present invention comprises a hindered Michael reagent. Typically the hindered Michael agent comprises a compound having the following structure:

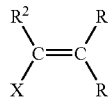

wherein X is an electron withdrawing group that is capable of stabilising a negative charge; the R groups independently comprise a hydrogen, a halogen, an alkyl, an aryl, or an aromatic group with the proviso that at least one of the R groups comprises a sterically hindering group; and the group $R^2$ comprises a hydrogen, a halogen, a hydrocarbon group, an electron withdrawing group and/or a linker capable of attachment to an affinity capture functionality or a solid phase support.

The present invention also provides a compound for labelling an analyte, which compound has the following structure:

wherein D comprises a light absorbing label, M comprises a mass modifier, L comprises a linker and A comprises an analyte.

In a preferred embodiment of the present invention, D comprises a dye, such as a non-fluorescent dye. Typically, the non-fluorescent dye comprises a compound selected from 4-dimethylaminoazobenzine-4'-sulphonyl chloride (DABSYL chloride), 3-hydroxypicolinic acid, 2,5-dihydroxybenzoic acid and 4-hydroxy-alpha-cyanocinnamic acid. M may be any mass marker, and is not especially limited. Preferably M is selected from a compound formed from an aryl ether, and an oligomer formed from 2 or more aryl ether units.

The linker is not especially limited and preferably comprises a group selected from —$CR_2$—$CH_2$—$SO_2$—, —$N(CR_2$—$CH_2$—$SO_2$—$)_2$, —NH—$CR_2$—$CH_2$—$SO_2$—, —CO—NH—, —CO—O—, —NH—CO—NH—, —NH—CS—NH—, —$CH_2$-NH—, —$SO_2$—NH—, —NH—CH2—CH2— and —OP(=O)(O)O—.

The analyte, A may be any analyte, as already discussed above in relation to the methods of the present invention. Preferably A is a biomolecule, such as a protein, a polypeptide, a peptide, a peptide fragment or an amino acid.

The present invention also provides a kit for characterising an analyte by matrix assisted laser desorption ionisation (MALDI) mass spectrometry, which kit comprises:
(a) a light absorbing label having a reactive functionality for attaching the label to an analyte; and
(b) a compound for forming a matrix, which compound absorbs light at the same frequency as the light-absorbing label.

The present invention will be described in further detail by way of example only with reference to the accompanying Figures, in which:

FIG. 1 shows a schematic description of the synthesis of two MALDI matrix mass tags based on 4-hydroxy-alpha-cyano-cinnamic acid;

FIG. 5a shows a schematic of the labelling protocol for beta-MSH (DEGPYKMEHFRWGSPPKD—SEQ ID NO: 5; DEGPYK—SEQ ID NO: 6; MEHFR—SEQ ID NO: 7; WGSPPKD—SEQ ID NO: 8).

Figure 6:
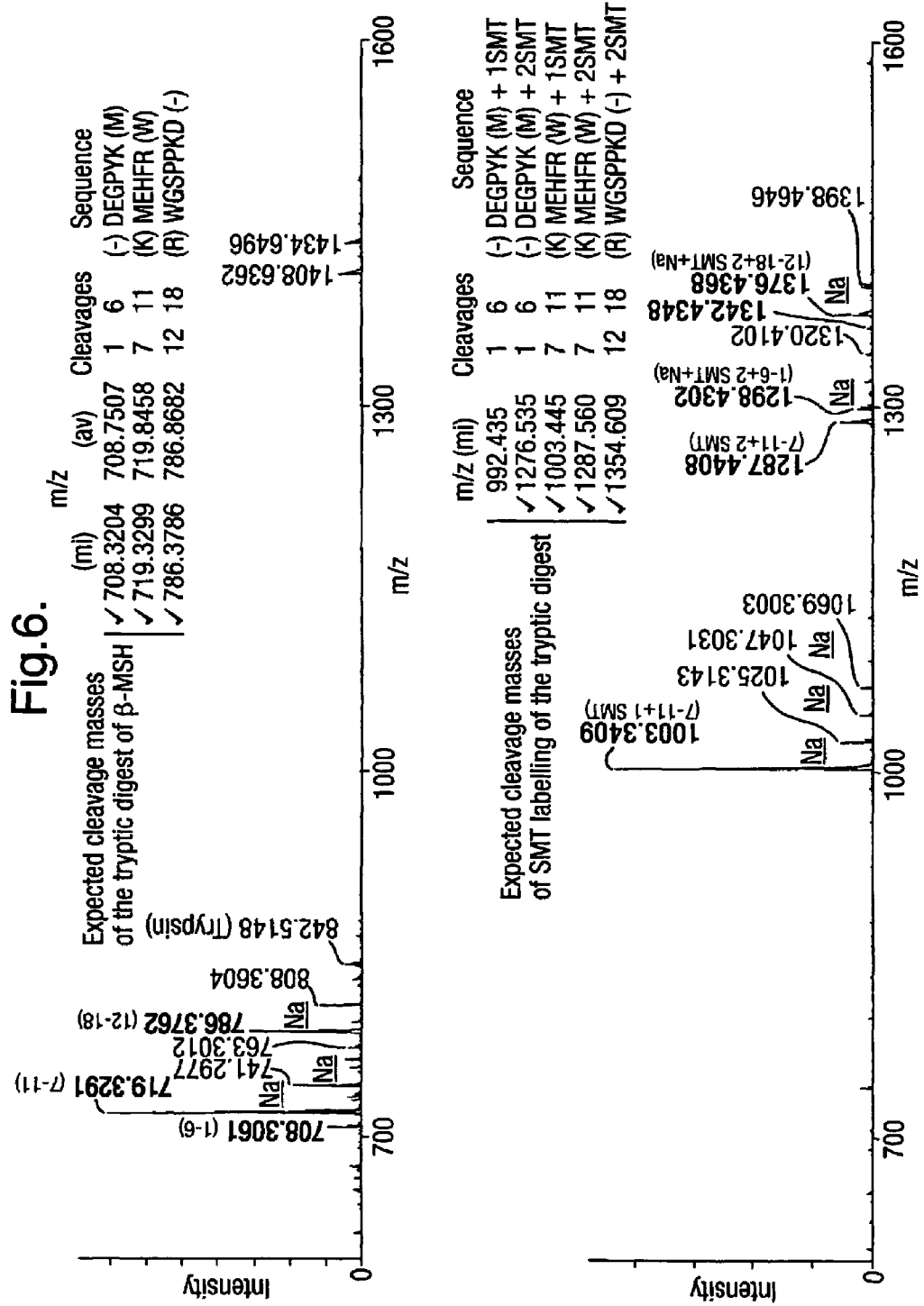
Figure 8:
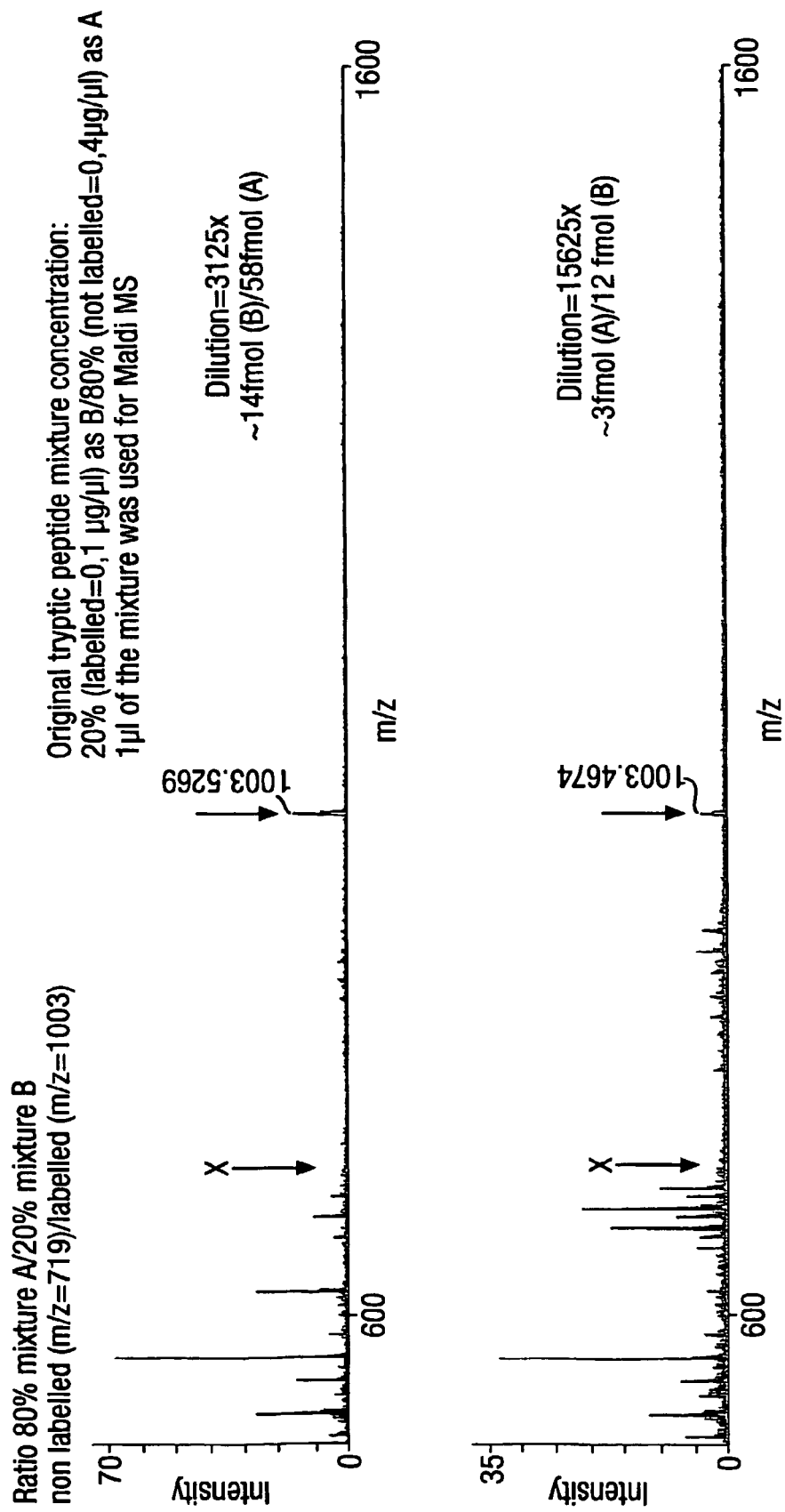
Figure 9:
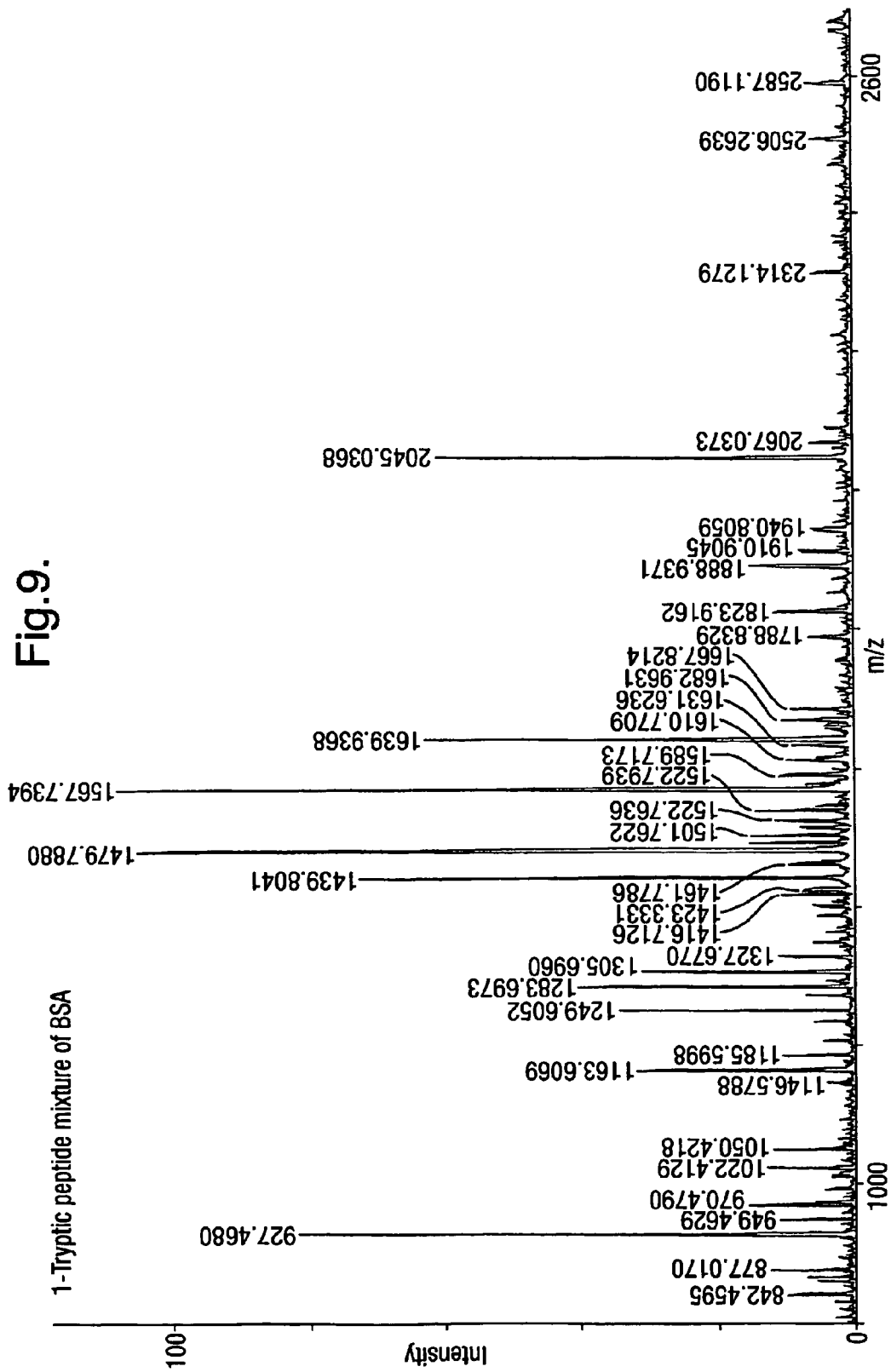
Figure 11:
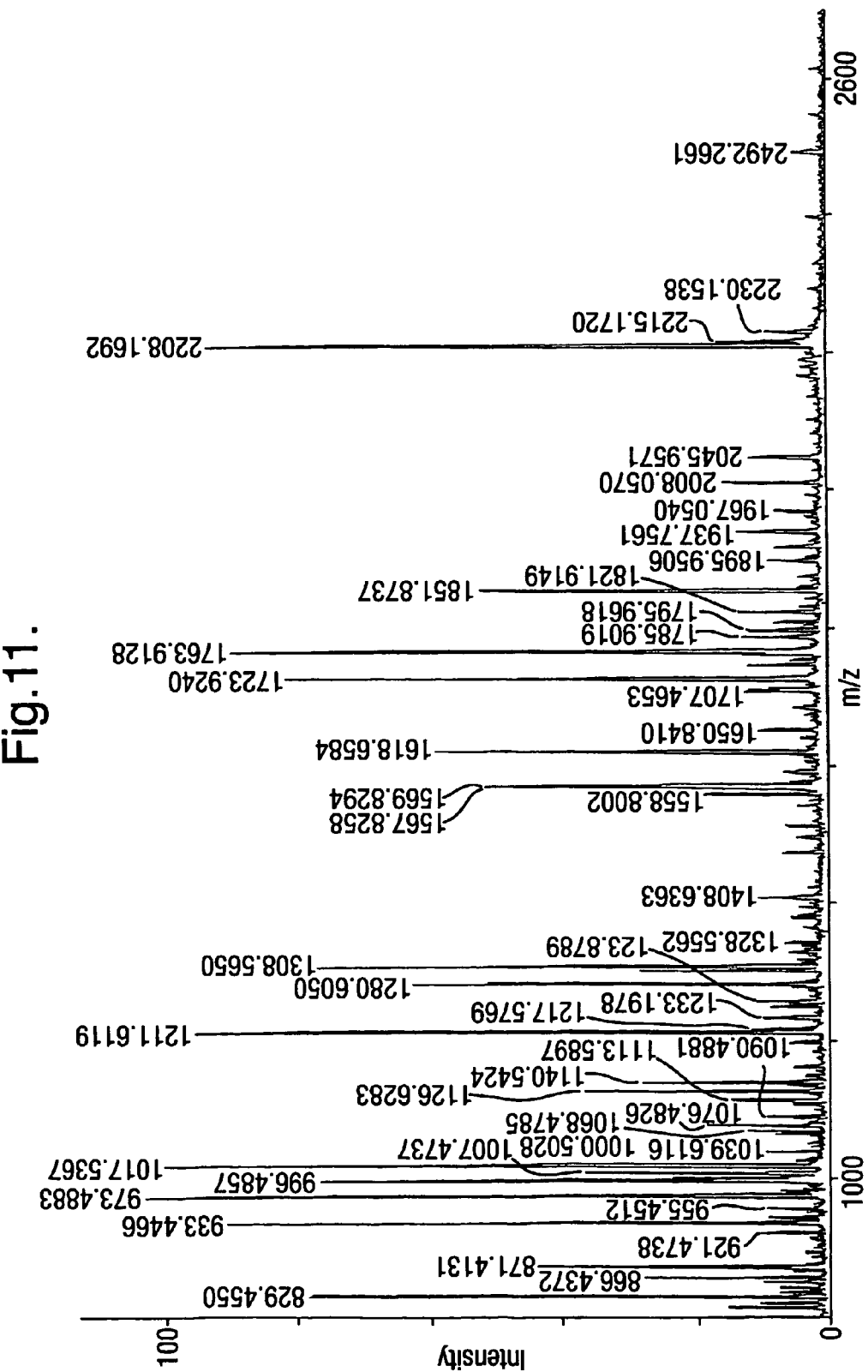
Figure 13:
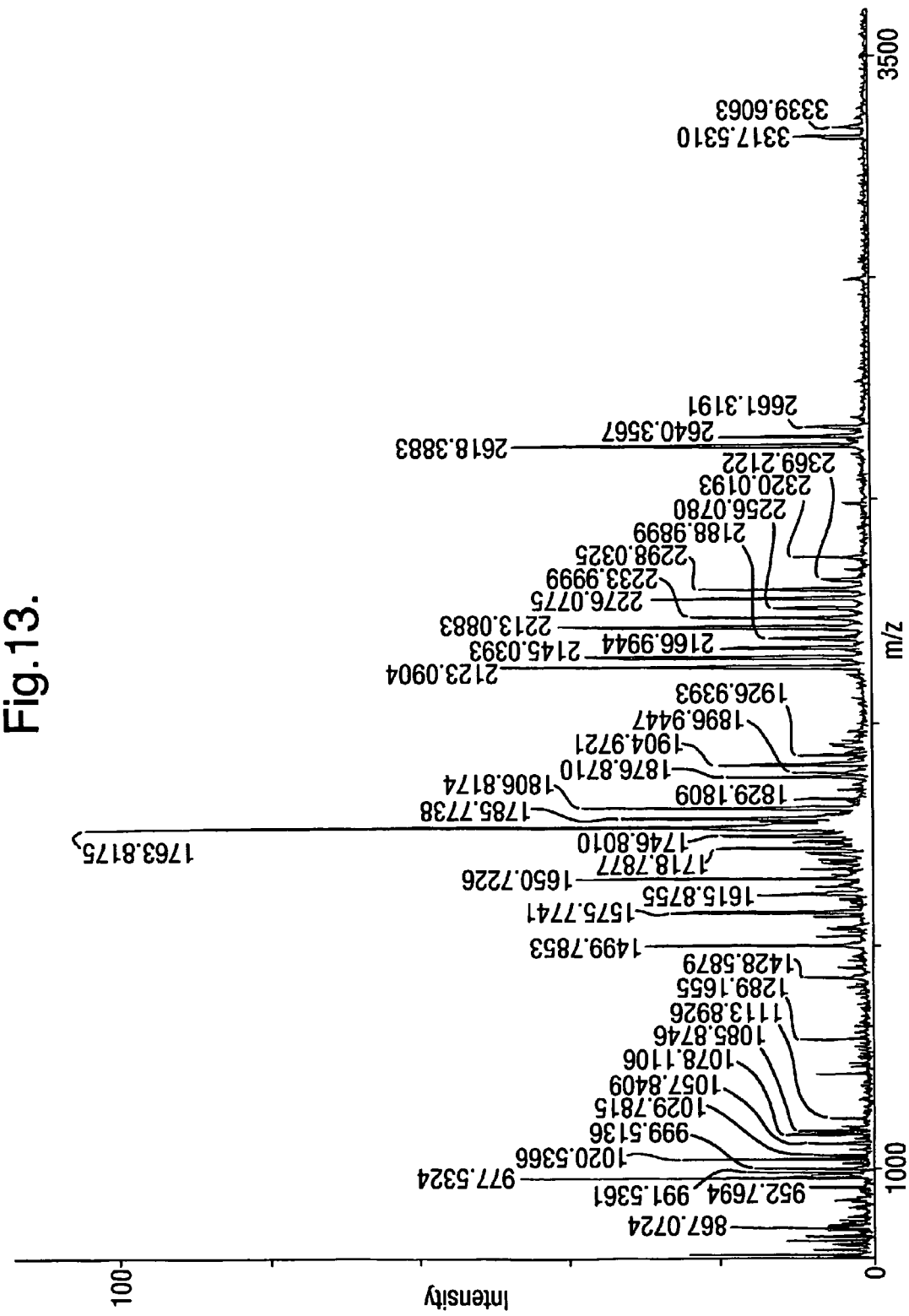
Figure 15:
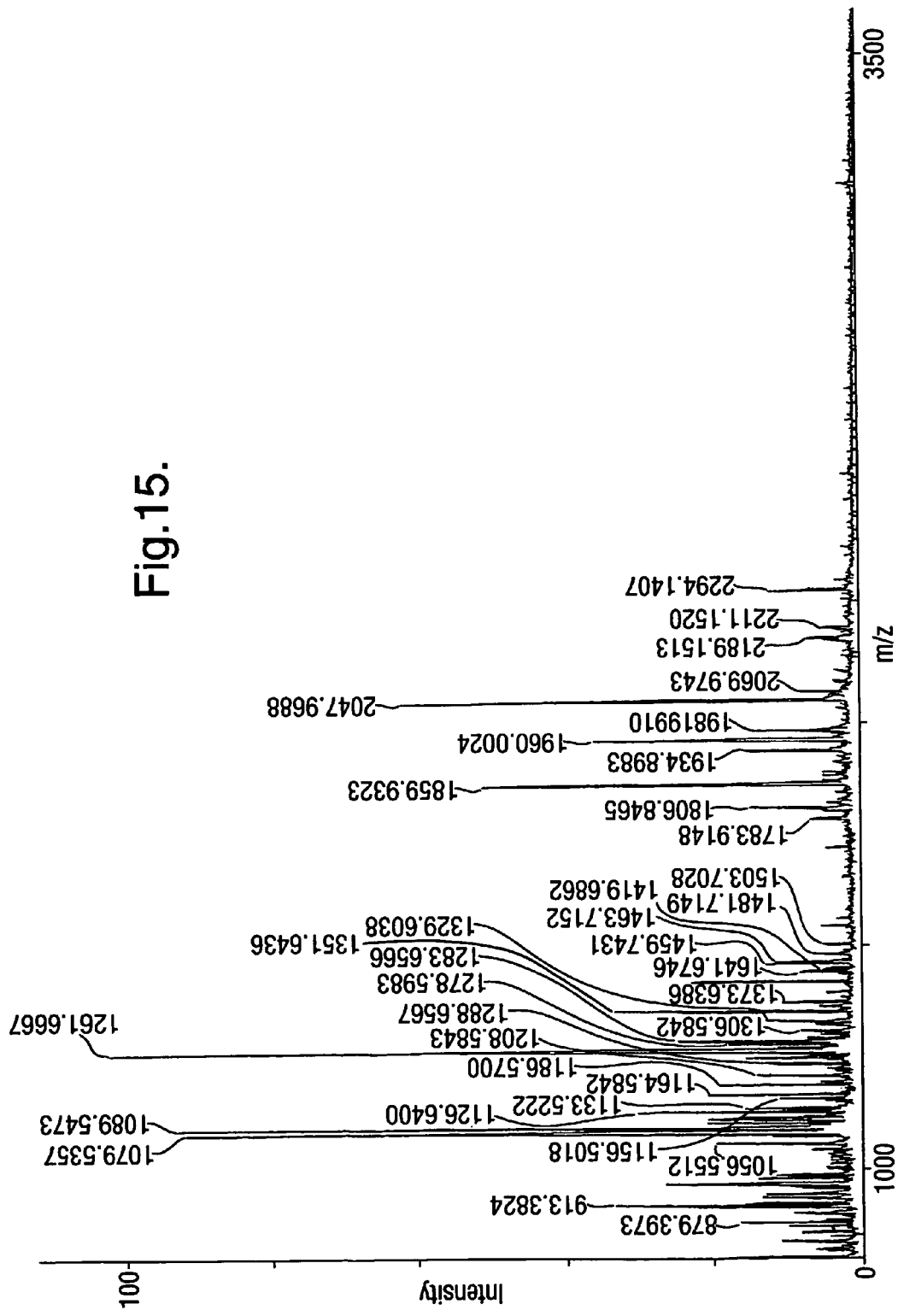
Figure 18:
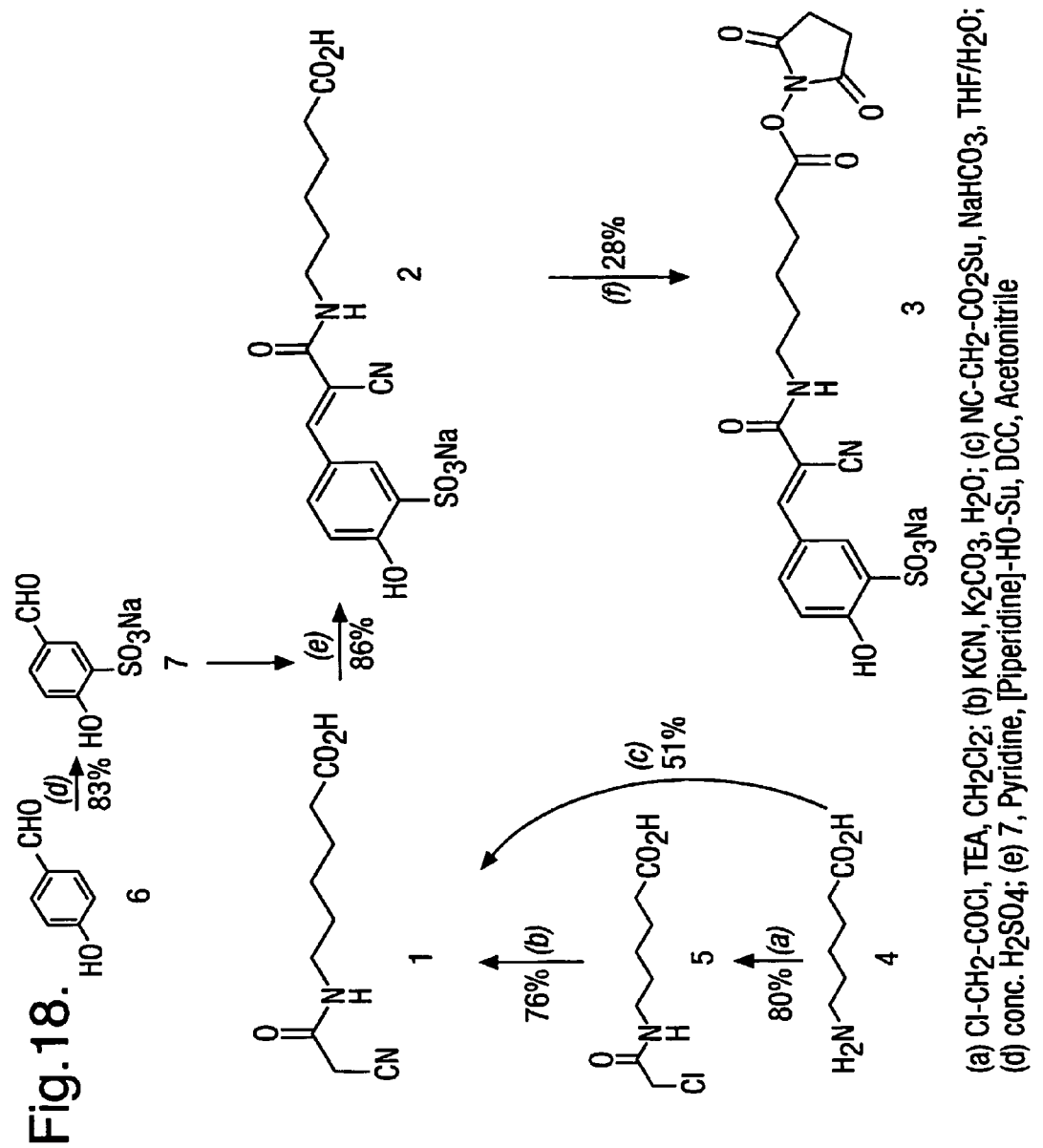
Figure 19:
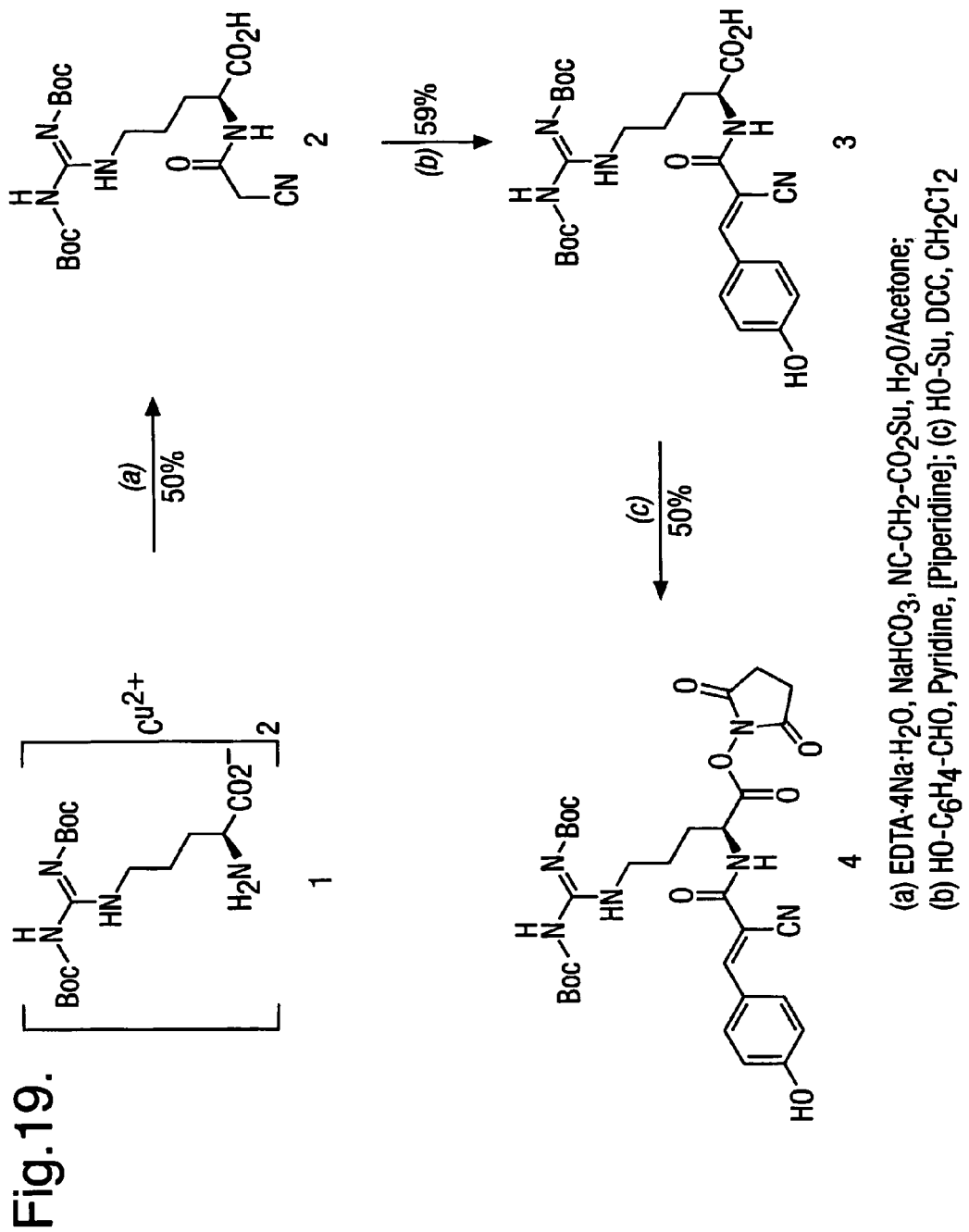
Figure 20:
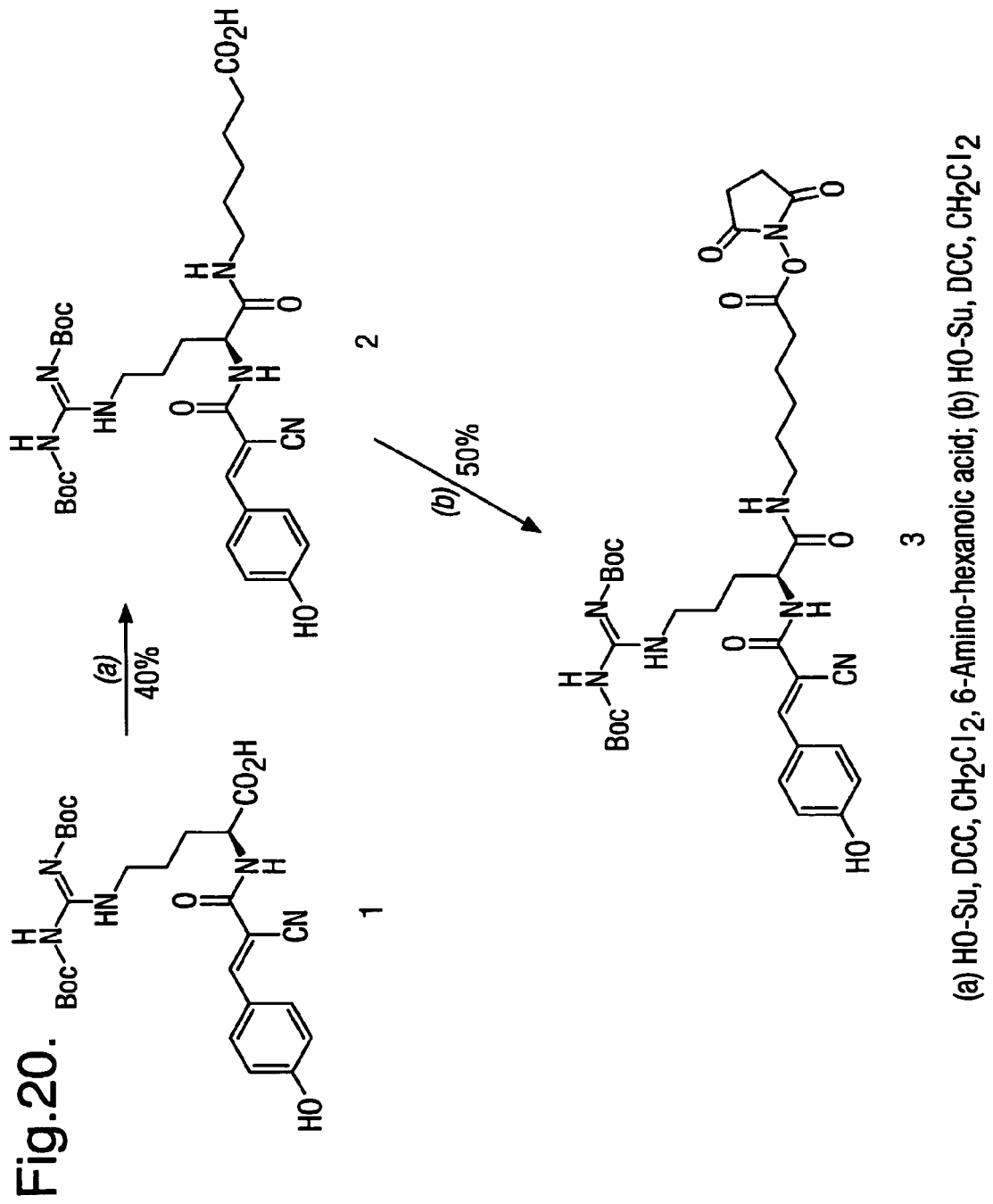
Figure 21:
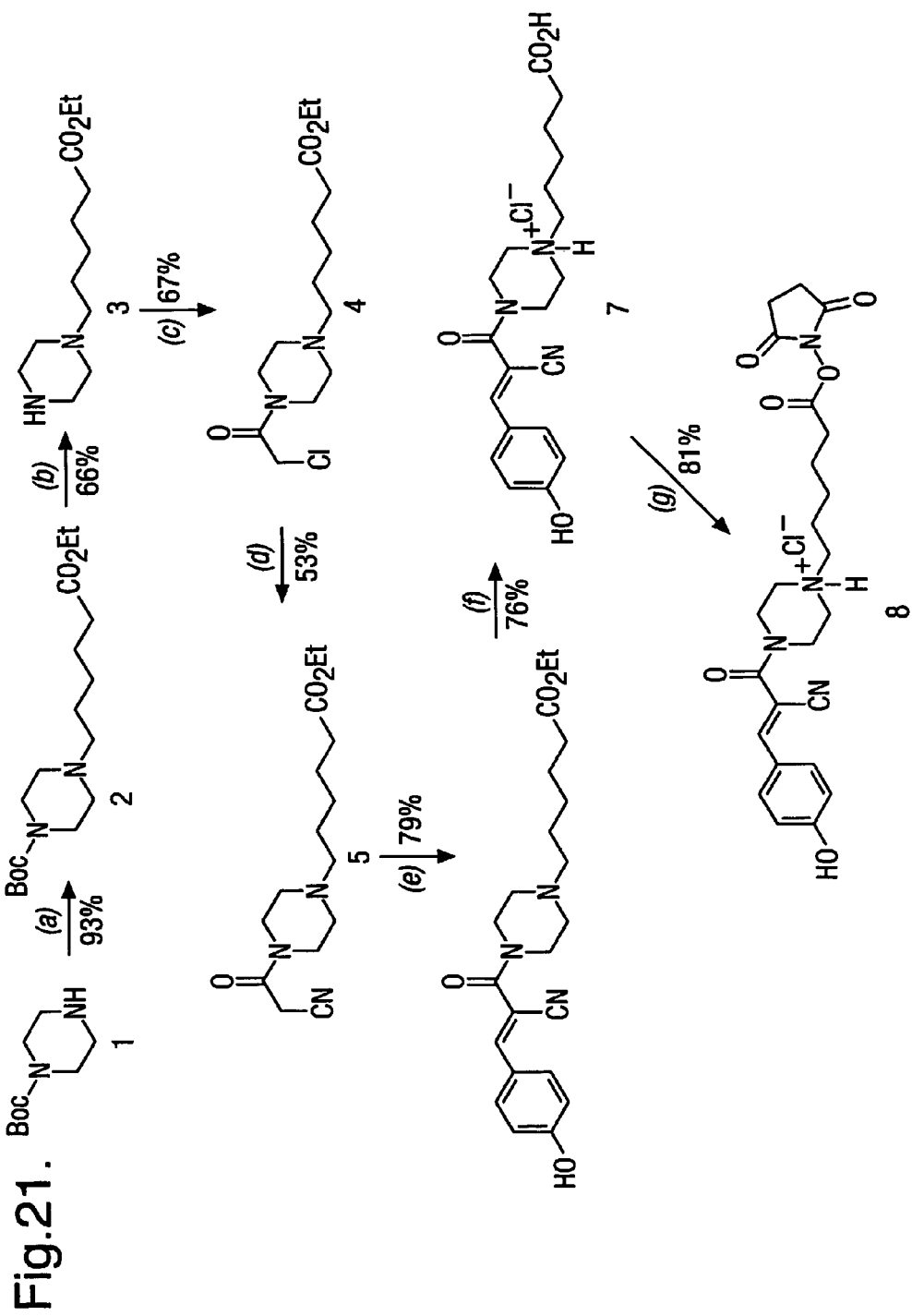

FIG. 5b shows the MALDI TOF mass spectrum of the unlabelled and undigested beta-MSH peptide;

FIG. 6 shows spectra MALDI TOF for the unlabelled and labeled digests of beta-MSH (DEGPYK—SEQ ID NO: 6; MEHFR—EQ ID NO: 7; WGSPPKD—SEQ ID NO: 8);

FIG. 7 shows MALDI TOF mass spectra of this peptide mixed in various molar ratios with the digest of unlabeled beta-MSH;

FIG. 8 shows a number of MALDI TOF mass spectra for a serial dilution of a stock solution of 44 pmol of the labelled peptide comprising amino acids 7 to 11 of beta-MSH mixed with 180 pmols of digested and unlabeled beta-MSH—the first spectrum shows the MALDI TOF analysis of the stock solution;

FIG. 9 shows a typical MALDI TOF peptide mass fingerprint mass spectrum for unlabelled BSA;

FIG. 10 shows the results of a search for unmodified BSA peptides in the SWISSPROT database using the MS-Fit database search program (KYLYEIARR —SEQ ID NO: 10; KLVNELTEFAKT—SEQ ID NO: 11, RFKDLGEEH-FKG—SEQ ID NO 12; RHPEYAVSVLLRL—SEQ ID NO: 13; KHLVDEPQNLIKQ—SEQ ID NO: 14; RRHPEYAVS-VLLRL—SEQ ID NO: 15; KLGEYGFQNALIVRY —SEQ ID NO: 16; KDAFGLSFLYEYSRR—SEQ ID NO: 17; RKVPQVSTPTLVEVSRS—SEQ ID NO: 18; RMPCT-EDYLSLILNRL—SEQ ID NO: 19; RRPCFSALTP-DETYVPKA—SEQ ID NO: 20; RHPYFYAPELLYYANKY —SEQ ID NO: 21; RRHPYFYAPELLYYANKY—SEQ ID NO: 22; RMPCTEDYLSLILNRLCVLHEKT—SEQ ID NO: 23; KHKPKATEEQLKTVMENFVAFVDKC-CAADDKE—SEQ ID NO: 24);

FIG. 11 shows a MALDI TOF peptide mass fingerprint mass spectrum for labelled BSA;

FIG. 12 shows the results of a search for modified BSA peptides in the SWISSPROT database using the MS-Fit database search program KVASLRE—SEQ ID NO: 25; KIET-MRE—SEQ ID NO: 26; RCASIQKF—SEQ ID NO: 27; KAWSVARL—SEQ ID NO: 28; KSEIAHRF—SEQ ID NO:

29; RDTHKS—SEQ ID NO: 30; KYLYEIARR—SEQ ID NO: 31; RCASIQKF—SEQ ID NO: 32; KKFWGKY—SEQ ID NO: 33; KCCTESLVNRR—SEQ ID NO: 34; RHPEYAVSVLLRL—SEQ ID NO: 35; RALKAW-SVARL—SEQ ID NO: 36; RRHPEYAVSVLLRL—SEQ ID NO: 37; KLGEYGFQNALIVRY—SEQ ID NO: 38; KVPQVSTPTLVEVSRS—SEQ ID NO: 39; KDAFLGS-FLYEYSRR—SEQ ID NO: 40; RKVPQVSTPTLVEVSRS—SEQ ID NO: 41);

FIG. 13 shows a typical MALDI TOF peptide mass fingerprint mass spectrum for unlabelled GAPDH;

FIG. 14 shows the results of a search for unmodified GAPDH peptides in the SWISSPROT database using the MS-Fit database search program (KAITIFQERD—SEQ ID NO: 42; RVPTPNVSVVDLTCRL—SEQ ID NO: 43; KAITIFQERDPANIKW—SEQ ID NO: 44; KLISWYD-NEFGYSNRV—SEQ ID NO: 45; KVIHDHGIVEGLMT-TVHAITATQKT—SEQ ID NO: 46; KVDVVAINDPFIDL-HYMVNMFQYDSTHGKF—SEQ ID NO: 47; KWGDAGAEYVVESTGVFTTMEKAGAHL-KGGAKRV—SEQ ID NO: 48);

FIG. 15 shows a MALDI TOF peptide mass fingerprint mass spectrum for labelled GAPDH;

FIG. 16 shows the results of a search for modified GAPDH peptides in the SWISSPROT database using the MS-Fit database search program KGGAKRV—SEQ ID NO: 49; KLTG-MAFRV—SEQ ID NO: 50; KVGVNGFGRI—SEQ ID NO: 51; KAGAHLKG—SEQ ID NO: 52; KAITIFQERD—SEQ ID NO: 53; KTVDGPSGKLWRD—SEQ ID NO: 54; RVPT-PNVSVVDLTCRL—SEQ ID NO: 55; KYDDIKKVVKQ—SEQ ID NO: 56; RDGRGAAQNIIPASTGAAKA—SEQ ID NO: 57; KLISWYDNEFGYSNRV—SEQ ID NO: 58);

FIG. 17a shows the tag compound 6-[2-Cyano-3-(4-hydroxy-3-sulfonato-phenyl)-acryloylamino]-hexanoic acid-(2,5-dioxo-pyrrolidin-1-yl)-ester Sodium;

FIG. 17b shows the tag compound N$^\alpha$-[2-Cyano-3-(4-hydroxyphenyl)-acryloyl]-Arg$^{\omega\omega'}$)(Boc$_2$)-2,5-dioxo-pyrrolidine-1-yl ester;

FIG. 17c shows the tag compound N$^\alpha$-[2-Cyano-3-(4-hydroxyphenyl)-acryloyl]-Arg-$^{\omega\omega'}$(Boc$^2$)-N-(6-amino-hexanoic acid-OSu-ester);

FIG. 17d shows the tag compound 4-[2-Cyano-3-(4-hydroxy-phenyl)-acryloyl]-1-[5-(2,5-dioxo-pyrrolidine-1-yloxycarbonyl)-pentyl]-piperazine-1-ium hydrochloride;

FIG. 18 shows a scheme for the synthesis of the tag compound 6-[2-Cyano-3-(4-hydroxy-3-sulfonato-phenyl)-acryloylamino]-hexanoic acid-(2,5-dioxo-pyrrolidin-1-yl)-ester Sodium shown in FIG. 17a;

FIG. 19 shows a scheme for the synthesis of the tag compound N$^\alpha$-[2-Cyano-3-(4-hydroxyphenyl)-acryloyl]-Arg$^{\omega\omega'}$(Boc$_2$)-2,5-dioxo-pyrrolidine-1-yl ester shown in FIG. 17b;

FIG. 20 shows a scheme for the synthesis of the tag compound N$^\alpha$-[2-Cyano-3-(4-hydroxyphenyl)-acryloyl]-Arg-$^{\omega\omega'}$(Boc$_2$)-N-(6-amino-hexanoic acid-OSu-ester) shown in FIG. 17c; and FIG. 21 shows a scheme for the synthesis of the tag compound 4-[2-Cyano-3-(4-hydroxy-phenyl)-acryloyl]-1-[5-(2,5-dioxo-pyrrolidine-1-yloxycarbonyl)-pentyl]-piperazine-1-ium hydrochloride shown in FIG. 17d.

The present invention will now be described in more detail.

In the present invention a label molecule of the following structure is employed for attaching the light-absorbing label (or dye) to the analyte of interest:

Dye—Reactive Functionality where the dye is preferably non-fluorescent and preferably dissipates absorbed radiation thermally.

In a preferred embodiment the label molecules comprise the following structure:

Dye—Mass Modifier-Linker—Reactive Functionality

In either case, the reactive functionality is not especially limited, provided that it is suitable for attaching the label to the analyte of interest.

In a preferred aspect of this invention there is provided a method of analysing an analyte molecule comprising the steps of:

1. Labelling the analyte molecule with a dye that absorbs light of a predetermined frequency.
2. Embedding the labelled analyte molecule in a matrix comprising a dye that absorbs light at the frequency of the laser to be used in the desorption step.
3. Desorbing the labelled analyte by application of laser light of the predetermined frequency so as to effect sublimation of the matrix and thus also the labelled analyte.
4. Detecting ions formed during the desorption step by mass spectrometry.

In a further aspect of this invention these is provided a kit comprising:

1. A mass label molecule usable in the first aspect of this invention; and
2. A compatible MALDI matrix reagent.

MALDI Matrix Dyes

Various compounds have been found to be useful as matrices for MALDI analysis of large biomolecules. These compounds are generally characterised by a number of properties. The compounds generally have a strong extinction coefficient at the frequency of the laser used for desorption. The compounds are also able to isolate analyte molecules in a solid solution and the compounds are sufficiently volatile to rapidly sublime when exposed to laser shots in the MALDI mass spectrometer. The subliming dye should vaporise rapidly in a jet that entrains the embedded analyte molecules and for most purposes this should take place without fragmentation of the analyte (although fragmentation may sometimes be desirable if structural information about the analyte is sought). However, a matrix should not be too volatile as experiments can sometimes take several hours and the analyte/matrix co-crystal must remain stable under vacuum in the ion source for this period of time. The property of volatility to laser irradiation can be measured approximately by determining the initial velocity of analyte ions generated by the matrix. It has been observed that higher initial velocities correspond to 'softer' ionisation, i.e. reduced fragmentation, (Karas M. & Glückmann M., J Mass Spectrom 34: 467-477, "The initial ion velocity and its dependence on matrix, analyte and preparation method in Ultraviolet Matrix-assisted Laser Desorption/Ionisation", 1999) but high initial ion velocities of some matrices also correlates to rapid sublimation under vacuum.

Different matrices have different properties in terms of their ability to assist in the desorption of embedded analytes and in the subsequent sensitivity with which the analytes are detected. It has been found empirically that certain matrices are more appropriate for the analysis of particular analytes than others. For example, 3-hydroxypicolinic acid has been found to be most effective for analysing oligonucleotides (Wu et al., Rapid Commun. Mass Spectrom. 7:142-146, "Matrix-assisted laser desorption time-of-flight mass spectrometry of oligonucleotides using 3-hydroxypicolinic acid as an ultraviolet sensitive matrix", 1993), while 2,5-dihydroxybenzoic acid and 4-hydroxy-alpha-cyano-cinnamic acid (HCCA) are both most effective for the analysis of peptides and proteins (Strupat et al., Int. J. Mass Spectrom. Ion Proc. 111: 89-102, "2,5-dihydroxybenzoic acid: a new matrix for laser desorption/ionisation mass spectrometry", 1991; Beavis et al., Org. Mass Spectrom. 27: 156-158, "α-cyano-4-hydroxy cinnamic acid as a matrix for matrix-assisted laser desorption mass spectrometry", 1992). Various cinnamic acid derivatives have been found to be effective for the analysis of proteins (Beavis R. C. & Chait B. T., Rapid Commun Mass Spectrom 3(12): 432-435, "Cinnamic acid derivatives as matrices for ultraviolet laser desorption mass spectrometry of proteins." 1989) and the choice of matrix is dependant on the nature of the analyte, for example sinnapinic acid may be preferred over HCCA for large peptides and polypeptides, while HCCA is generally preferred for smaller peptides. 2,5-dihydroxybenzoic acid may produce less fragmentation than the cinnamic acid derivatives in some cases.

Most of the matrices discussed above have been acidic matrices. Basic matrices have also been developed and may be more appropriate for the analysis of acid-sensitive compounds (Fitzgerald et al., Anal Chem. 65(22): 3204-3211, "Basic matrices for the matrix-assisted laser desorption/ionisation mass spectrometry of proteins and oligonucleotides." 1993).

Infrared MALDI (IR-MALDI) is similar in principal to ultraviolet MALDI (UV-MALDI) in that analytes must be embedded in a matrix that preferably has a strong extinction coefficient at the frequency of the laser in the desorption instrument. Appropriate matrices tend to be different compounds from those used in UV-MALDI and liquid matrices are often used. Glycerol, urea, ice and succinic acid have all been shown to be effective matrices for IR-MALDI (Talrose et al., Rapid Commun Mass Spectrom 13(21): 2191-2198, "Insight into absorption of radiation/energy transfer in infrared matrix-assisted laser desorption/ionisation: the roles of matrices, water and metal substrates." 1999). However, some UV-MALDI matrices, such as cinnamic acid derivatives, also work as IR matrices (Niu et al., J. Am. Soc. Mass Spectrom. 9:1-7, "Direct comparison of infrared and ultraviolet wavelength matrix-assisted laser desorption/ionisation mass spectrometry of proteins", 1998).

Liquid matrices for UV-MALDI have also been explored (Ring S. & Rudich Y., Rapid Commun Mass Spectrom 14(6): 515-519, "A comparative study of a liquid and a solid matrix in matrix-assisted laser desorption/ionisation time-of-flight mass spectrometry and collision cross section measurements." 2000; Sze et al., J Am Soc Mass Spectrom 9(2): 166-174, "Formulation of matrix solutions for use in matrix-assisted laser desorption/ionisation of biomolecules." 1998; Karas et al. Mass Spectrom Rev 10: 335, 1991). The simplest examples of liquid matrices comprise solutions of the matrices used as solids. True liquid matrices are also known such as nitrobenzoyl alcohol. Both types of matrix have some advantages in terms of sample consistency, stability under vacuum and ease of handling, however solid matrices tend to be more sensitive. In the context of the present invention, the improvements in sensitivity may justify the use of liquid matrices. This may have particular advantages in the automation of sample preparation, as liquid handling robotics are widely available and the use of solutions of matrices, for solid matrix co-crystallisation, which readily clog dispensing devices can be avoided.

Reactive Tags Comprising Dyes and MALDI Matrix Dyes

In the one aspect of this invention light-absorbing dye molecules attached to analytes are provided. Various dyes that are not conventionally used in MALDI mass spectrometry may be used with this invention. Some dyes that absorb strongly in UV frequencies are commercially available with reactive functionalites, e.g. 4-dimethylaminoazobenzene-4'-sulfonyl chloride (DABSYL Chloride, Sigma-Aldrich, Poole, Dorset, UK). This reagent and similar UV absorbing dyes that thermally dissipate luminal excitation are applicable with this invention.

It is also possible to prepare reactive dyes from commercially available intermediates. A number of acidic matrices that are widely used for MALDI mass spectrometry, such as cinnamic, nicotinic and hydroxybenzoic acid derivatives, are commercially available. The acidic functionality in most of these reagents is a carboxylic acid group. This functionality may be readily converted to an active ester or acid chloride by conventional chemical methods (see for example Solomons, "Organic Chemistry", Fifth Edition published by Wiley). Preferred active esters include N-hydroxysuccinimide (NHS) esters and pentafluorophenyl esters. A variety of dyes will function in the methods of this invention, but preferred compounds absorb strongly in the frequency that is used for laser desorption in the mass spectrometer. Typically Ultra-Violet (UV) radiation is used. Infra-red lasers are also used for some MALDI applications.

Cinnamic acid derivatives are preferred dyes that are widely used in UV-MALDI TOF (Beavis R C, Chait B T, Rapid Commun Mass Spectrom 3(12):432-435, "Cinnamnic acid derivatives as matrices for ultraviolet laser desorption mass spectrometry of proteins." 1989). A reactive derivative of cinnamic acid is discussed in the examples below. It is anticipated that this reagent may be applicable to both UV- and IR-MALDI.

Reactive Functionalities

A variety of other reactive functionalities may be appropriate to prepare reactive dyes for use with this invention. Table 1 below lists some reactive functionalities that may be incorporated into a dye molecule. These reactive functionalities may be reacted with nucleophilic functionalities which are found in biomolecules, particularly in peptides and polypeptides. Reaction of the reactive functionalities with the nucleophilic functionalities shown generates a covalent linkage between the two entities. This covalent linkage is shown in the third column of the table. For applications involving synthetic oligonucleotides, primary amines or thiols are often introduced during the synthesis at the termini of the molecules to permit labelling. Any of the functionalities listed below could be introduced into the compounds of this invention to permit the mass markers to be attached to a molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —$SO_2$—CH=$CR_2$ | —S—$CR_2$—$CH_2$—$SO_2$— |
| —$NH_2$ | —$SO_2$—CH=$CR_2$ | —N($CR_2$—$CH_2$—$SO_2$—$)_2$ or —NH—$CR_2$—$CH_2$—$SO_2$— |

TABLE 1-continued

| Nucleophilic Functionality | Reactive Functionality | Resultant Linking Group |
|---|---|---|
| —NH$_2$ —OH | 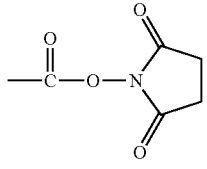 | —CO—NH— —CO—O— |
| —NH$_2$ —OH | 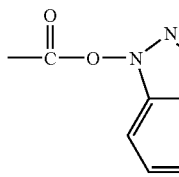 | —CO—NH— —CO—O— |
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | CH$_2$=CH— | —NH—CH$_2$—CH$_2$— |
| —OH | —OP(NCH(CH$_3$)$_2$)$_2$ | —OP(=O)(O)O— |

It should be noted that in applications involving labelling oligonucleotides with the mass markers of this invention, some of the reactive functionalities above or their resultant linking groups might have to be protected prior to introduction into an oligonucleotide synthesiser. Preferably unprotected ester, thioether and thioesters, amine and amide bonds are to be avoided, as these are not usually stable in an oligonucleotide synthesiser. A wide variety of protective groups is known in the art which can be used to protect linkages from unwanted side reactions. Alternatively, amine functionalised oligonucleotides can be prepared using standard methods known in the art and these can be labelled with amine reactive reagents such as NHS-esters.

Analysis of Labelled Biomolecules

In the second aspect of this invention, a method of detecting biomolecules is provided. In this method the biomolecules are covalently labelled with a dye molecule. The labelled molecules are then embedded in a MALDI matrix of a further dye molecule, which may be the same or different from the dye used to label the biomolecule. The labelled and embedded biomolecules are then analysed in a MALDI mass spectrometer. The dye used to label the analyte biomolecule and the dye chosen as a free matrix are both chosen to absorb light strongly in the frequency used for the MALDI process. Typically, laser Ultra-Violet (UV) frequencies of 266 nm (Nd-YAG lasers) or 337 nm (Nitrogen Lasers) are used.

Peptides and proteins are preferred biomolecules that benefit from the methods of this invention. A polypeptide or peptide or mixtures of polypeptides or peptides can be isolated for analysis by any of the conventional means such as electrophoresis, chromatography or affinity chromatography. For the purposes of mass spectrometry, it is preferred that polypeptides or proteins are not contaminated with salts or detergents, particularly metal salts. Various techniques for desalting a polypeptide or peptide mixture are known in the art such as gel filtration, dialysis or the use of hydrophobic resins. A particularly convenient and simple method for desalting peptides involves aspiration of a small quantity of a solution of the peptide or polypeptide mixture in a pipette tip incorporating C18 packing materials. Salts and detergents will be removed first, substantially improving the detection sensitivity of the analysis of the peptides. Pipette tips prepackaged with appropriate resins and instructions for their use are commercially available from Millipore (Bedford, Mass., USA) under the trademark 'Zip Tip'. Desalting procedures may take place after labelling of the analyte to remove unreacted tags, if preferred.

Proteins contain various nucleophilic functionalities that can be labelled using reagents that are reactive to these functionalities. Proteins typically contain thiol, amino, hydroxyl and imidazole groups. These may all be labelled with appropriate reagents if desired. In preferred embodiments of this invention, amino groups are labelled. Amino groups may be labelled with a variety of labels but acid chlorides and active esters are usually the most selective reactive functionalities. Preferred UV-absorbing dyes for use with this invention include active esters of cinnamic acid and its derivatives, active esters of nicotinic acid or active esters of hydroxybenzoic acid derivatives. Thus, in one embodiment of the second aspect of this inventions, isolated peptides in a mixture are labelled with an active ester of 4-hydroxy-alpha-cyano-cinnamic acid. The peptides are desalted using a Zip tip and then embedded in a matrix of unmodified 4-hydroxy-alpha-cyano-cinnamic acid. Typically, a solution of the matrix is prepared in a volatile solvent such as acetonitrile containing a small amount of trifluoroacetic acid (0.1 to 0.5% by volume is sufficient). This solution is then pipetted onto a metal target to form small droplets. A small quantity of the desalted, labelled peptide solution is then dropped into the droplet of matrix solution. This solution is then left to dry so that the peptides can co-crystallise with the matrix. In other techniques the matrix solution is allowed to dry and crystallise before the peptide solution is added on top (Hutchens and Yip, Rapid Commun. Mass Spectrom. 7: 576-580, 1993). This procedure may also be repeated to produce layers of co-crystallised analyte and matrix. These and other variations of the co-crystallisation technique may be used to improve the analysis of peptides or polypeptides. Liquid matrices, as discussed above may also be used. The matrix/peptide co-crystals are then analysed by laser desorption in a MALDI-TOF mass spectrometer.

Mass Spectrometers

The essential features of a mass spectrometer are as follows

Inlet System->Ion Source->Mass Analyser->Ion
        Detector->Data Capture System There are various inlet systems, ion sources and mass analysers that can be used for the purposes of analysing large biomolecules but in the context of this invention the ion source is a Matrix Assisted Laser Desorption ion source for which there are only a limited number of inlet systems. A variety of mass analysers, ion detectors and data capture systems may be used with MALDI although some mass spectrometer geometries are not commercially produced. Time-of-flight mass analysers are typically used with MALDI as well as Fourier Transform Ion Cyclotron Resonance mass analysers and Quadrupole/Time-of-flight mass analysers. In principle ion traps and sector instruments can be used with MALDI but generally these are not commercially produced.

Inlet Systems

Moving belt systems are one of the few inlet systems that have been used with laser desorption for the analysis of labelled nucleic acids (Linxiao Xu et al., Anal. Chem. 69: 3595-3602, "Electrophore Mass Tag Dideoxy DNA sequencing", 1997). Although this technology has not been used with MALDI it should be trivial to adapt such interfaces for use with the reagents and methods of this invention.

Matrix Assisted Laser Desorption Ionisation (MALDI)

MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. The laser energy and the timing of the application of the potential difference used to accelerate the ions from the source can be used to control fragmentation with this technique. This technique is highly favoured for the determination of peptide mass fingerprints due to its large mass range, due to the prevalence of singly charged ions in its spectra and due to the ability to analyse multiple peptides simultaneously.

The photo-excitable matrix comprises a 'dye', i.e. a compound that strongly absorbs light of a particular frequency, and which preferably does not radiate that energy by fluorescence or phosphorescence but rather dissipates the energy thermally, i.e. through vibrational modes. It is the vibration of the matrix caused by laser excitation that results in rapid sublimation of the dye which simultaneously takes the embedded analyte into the gas phase.

Mass Analysers

Time-Of-Flight Mass Analysers

As the name implies, Time-of-flight mass analysers measure the time it takes for ions to travel a predetermined distance under the influence of a predetermined potential difference. The time-of-flight measurement allows the mass-to-charge ratio of ions string a detector to be calculated. These instruments measure the arrival of almost all of the ions in a sample and as a result can be quite sensitive although, selectivity with this technique is more difficult to achieve. This technique can also detect ions with higher mass-to-charge ratios than can typically be measured in an ion trap or quadrupole mass spectrometer. TOF mass analysers are presently widely used with MALDI.

Ion Traps

Ion Trap mass analysers are related to the quadrupole mass analysers. The ion trap generally has a 3-electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. A pair of plate electrodes that form two sides of a box generates the electric field. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radiofrequency pulse to two 'transmitter plates', which form two further opposing sides of the box. The cycloidal motion of the ions generates corresponding electric fields in the remaining two opposing sides of the box, which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed.

Analysis of Peptides by Mass Spectrometry

Fragmentation of peptides by collision induced dissociation, to determine their sequence, may be used in this invention to identify proteins, not identified by the pattern of masses of their digestion products. In addition, fragmentation can also be obtained by photo-excitation or by electron impact. Various mass analyser geometries may be used to fragment peptides and to determine the mass of the fragments.

MS/MS and $MS^n$ Analysis of Peptides

Tandem mass spectrometers allow ions with a pre-determined mass-to-charge ratio to be selected and fragmented (by collision induced dissociation (CID), for example). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

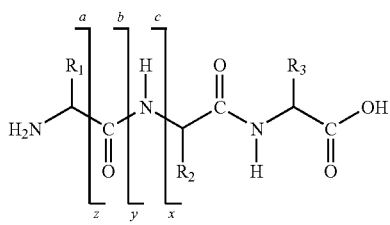

Trypsin, Lys-C and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

In general peptides fragment via a mechanism that involves protonation of the amide backbone follow by intramolecular nucleophilic attack leading to the formation of a 5-membered oxazolone structure and cleavage of the amide linkage that was protonated (Schlosser A. and Lehmann W. D. J. Mass Spectrom. 35: 1382-1390, "Five-membered ring formation in unimolecular reactions of peptides: a key structural element controlling low-energy collision induced dissociation", 2000). FIG. 16a shows one proposed mechanism by which this sort of fragmentation takes place. This mechanism requires a carbonyl group from an amide bond adjacent to a protonated amide on the N-terminal side of the protonated amide to carry out the nucleophilic attack. A charged oxazolonium ion gives rise to b-series ions, while proton transfer from the N-terminal fragment to the C-terminal fragment gives rise to y-series ions as shown in FIG. 16a. This requirement for an appropriately located carbonyl group does not account for cleavage at amide bonds adjacent to the N-terminal amino acid, when the N-terminus is not protected and, in general, b-series ions are not seen for the amide between the N-terminal and second amino acid in a peptide. However, peptides with acetylated N-termini do meet the structural requirements of this mechanism and fragmentation can take place at the amide bond immediately after the first amino acid by this mechanism. Peptides labelled on lysine or at an alpha-amino group with active ester tags of this invention should not undergo significant cleavage at the tag peptide during low energy CID analysis if there is no appropriately located carbonyl group in the tag molecule. This means that CID spectra for labelled peptides should be similar to the spectra for unlabelled peptides although the spectra will show mass shifts corresponding to multiples of the mass of the tag. This can be readily compensated for in the analysis of such CID spectra.

A typical tandem mass spectrometer geometry is a triple quadrupole which comprises two quadrupole mass analysers separated by a collision chamber, also a quadrupole. This collision quadrupole acts as an ion guide between the two mass analyser quadrupoles. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Induced cleavage can be performed in geometries other than tandem analysers. Ion trap mass spectrometers can promote fragmentation through excitation of a defined m/z range resulting in collision with the bath gas. Ion traps generally contain a bath gas, such as helium. Similarly photon induced fragmentation could be applied to trapped ions. Another favourable geometry is a Quadrupole/Orthogonal Time of Flight tandem instrument where the high selectivity of the quadrupole is coupled to the high sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Affinity Capture Ligands

In certain embodiments of this invention the mass markers comprise an affinity capture ligand. Affinity capture ligands are ligands, which have highly specific binding partners. These binding partners allow molecules tagged with the ligand to be selectively captured by the binding partner. Preferably a solid support is derivitised with the binding partner so that affinity ligand tagged molecules can be selectively captured onto the solid phase support. The use of an affinity capture ligand provides many advantages, in that tagged species can be selectively captured prior to analysis allowing separation of tagged and untagged material while also allowing for conditioning of the analyte for mass spectrometry. Conditioning of a sample may include removal of detergents and other contaminants that can suppress ionisation or otherwise interfere with mass spectrometry. Conditioning also includes removal of salts that may form adducts with analytes causing mass shifts in the mass spectrum. In addition, pH may be adjusted to optimise ionisation. Conditioning of tagged analytes captured onto a solid phase support is trivial as the captured material can be easily washed with an appropriate buffer comprising volatile salts such as ammonium carbonate or trifluoroacetic acid depending on the desired pH. This washing step can remove contaminants and can be used to adjust the pH appropriately.

A further advantage of the inclusion of an affinity ligand is the ability to selectively isolate certain analyte species if the tag additionally comprises a reactive functionality that will couple the affinity ligand to specific analytes. For example, Gygi et al. (Nature Biotechnology 17: 994-999, 1999) disclose the use of 'isotope encoded affinity tags' (ICAT) for the capture of peptides from proteins, to allow protein expression analysis. The authors report that a large proportion of proteins (>90%) in yeast have at least one cysteine residue (on average there are ~5 cysteine residues per protein). Reduction of disulphide bonds in a protein sample and capping of free thiols with iodoacetamidylbiotin results in the labelling of all cysteine residues. The labelled proteins are then digested, with trypsin for example, and the cysteine-labelled peptides may be isolated using avidinated beads. These captured peptides can then be analysed by liquid chromatography tandem mass spectrometry (LC-MS/MS) to determine an expression profile for the protein sample. Two protein samples can be compared by labelling the cysteine residues with a different isotopically modified biotin tag. In a useful embodiment of this invention, isotopically differentiated, cysteine reactive tags of this invention comprising an affinity ligand may be employed to improve the sensitivity of the ICAT analysis method. Similarly, Schmidt and Thompson (WO 98/32876) disclose the use biotin reagents to capture C- or N-terminal peptides for protein expression profiling analysis by mass spectrometry. The sensitivity of this process would also be enhanced by tags of this invention comprising an affinity ligand.

A preferred affinity capture ligand is biotin, which can be introduced into the tags of this invention by standard methods known in the art. In particular a lysine residue may be incorporated after amino acid 2 through which an amine-reactive biotin can be linked to the peptide mass tags (see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analog of [Lys]bradykinin." 1991; Natarajan S. et al., Int J Pept Protein Res 40(6): 567-567, "Site-specific biotinylation. A novel approach and its application to endothelin-1 analogs and PTH-analog.", 1992). Iminobiotin and desthiobiotin are also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Metal ion binding ligands such as hexahistidine, which readily binds $Ni^{2+}$ ions, are also applicable. Chromatographic resins, which present iminodiacetic acid chelated $Ni^{2+}$ ions are commercially available, for example. These immobilised nickel columns may be used to capture tagged peptide, which comprise oligomeric histidine. As a further alternative, an affinity capture functionality may be selectively reactive with an appropriately derivitised solid phase support. Boronic acid, for example, is known to selectively react with vicinal cis-diols and chemically similar ligands, such as salicylhydroxamic acid. Reagents comprising boronic acid have been developed for protein capture onto solid supports derivitised with salicylhydroxamic acid (Stolowitz M. L. et al., Bioconjug Chem 12(2): 229-239, "Phenylboronic Acid-Salicylhydroxamic Acid Bioconjugates. 1. A Novel Boronic Acid Complex for Protein Immobilization." 2001; Wiley J. P. et al., Bioconjug Chem 12(2): 240-250, "Phenylboronic Acid-Salicylhydroxamic Acid Bioconjugates. 2. Polyvalent Immobilization of Protein Ligands for Affinity Chromatography." 2001, Prolinx, Inc, Washington State, USA). It is anticipated that it should be relatively simple to link a phenylboronic acid functionality to the tags of this invention to generate capture reagents that can be captured by selective chemical reactions. The use of this sort of chemistry would not be directly compatible with biomolecules bearing vicinal cis-diol-containing sugars, however these sorts of sugars could be blocked with phenylboronic acid or related reagents prior to reaction with boronic acid derivitised tag reagents.

Charge Derivatisation of Peptides

In some embodiments of the this invention the tags may comprise readily ionisable groups, which can assist both in solubilisation of the tag and tagged analytes and in ionisation of the tagged analytes in the mass spectrometer. Various functionalities can be used as ionisable groups. The tertiary amino group and the guanidino group are both useful functionalities for solubilisation and ionisation (Francesco L. Branca, Stephen G. Oliver and Simon J. Gaskell, Rapid Commun. in Mass Spec., 14, 2070-2073, "Improved matrix-assisted laser desorption/ionisation mass spectrometric analysis of tryptic hydrolysates of proteins following guanidination of lysine-containing peptides." 2000).

Various other methods for derivatising peptides have been also been developed. These include the use of quaternary ammonium derivatives, quaternary phosphonium derivatives and pyridyl derivatives for positive ion mass spectrometry. Each type of ionisable functionality has different benefits, which depend on the method of ionisation used and on the methods of mass analysis used. Some derivitisation reagents increase basicity and thus promote protonation and/or charge localization for positive ion mass spectrometry while other reagents readily lose protons making them appropriate for negative ion mass spectrometry, which is often more sensitive than positive ion mass spectrometry because there is less background noise. Charge derivitisation can also change the fragmentation products of derivatised peptides, when collision induced dissociation is used. In particular some derivatisation techniques simplify fragmentation patterns, which is highly advantageous, if peptides are to be analysed by techniques such as collision induced dissociation. The choice of ionising functionality will be determined by the mass spectrometric techniques that will be employed (for a review see Roth et al., Mass Spectrometry Reviews 17:255-274, "Charge derivatisation of peptides for analysis by mass spectrometry", 1998). For the purposes of this invention ionising functions that promote positive or negative ion formation are equally applicable.

Charged groups such as tertiary amino functionalities, guanidino functionalities and sulphonic acid functionalities provide an additional advantage. These groups can act as affinity ligands allowing tagged analytes to be purified by ion exchange. Tags comprising guanidino and tertiary amino functions can be captured onto a strong cation exchange resin allowing conditioning prior to mass spectrometry analysis. Similarly, tags comprising sulphonic acid functions can be captured onto anion exchange resins allowing conditioning prior to mass spectrometry analysis. Additionally, the interaction between unreacted tags and the resin, anion or cation exchange, is weaker than the interaction of tagged analytes allowing unreacted tag to be readily washed away. The tagged analytes can be eluted with an appropriate buffer comprising a suitable concentration of a volatile acid, base or salt depending on the resin. Accordingly, it is envisaged that pipette tips, spin columns and cartridges packed with a cation exchange resin or an anion exchange resin will be useful tools for the preparation of labelled samples to allow facile clean-up of the labelled peptides prior to analysis.

In addition sulphonic acid groups are advantageous for MALDI TOF analysis. Sulphonic acid derivatives of the alpha-amino functionality of peptides have been shown to enhance fragmentation efficiency in MALDI-Ion Trap analysis of peptides with improved spectra for certain classes of peptides that typically give poor MS/MS spectra in the ion trap, such as peptides containing aspartic and glutamic acid (Keough, T., Lacey M. P., et al., Rapid Commun Mass Spectrom 15(23): 2227-2239, "Atmospheric pressure matrix-assisted laser desorption/ionisation ion trap mass spectrometry of sulphonic acid derivatised tryptic peptides.", 2001). The strongly acidic functionality facilitates protonation of the amide backbone of singly charged peptides in MALDI leading to increased fragmentation.

In specific embodiments of this invention, tags comprising guanidino groups and sulphonic acid groups have been synthesized, see FIGS. 17, 18 and 19 and the examples section. In general preferred charged groups include guanidino groups, tertiary amino groups and sulphonic acid groups.

Surface Enhanced Laser Desorption Ionisation

Surface Enhanced Laser Desorption Ionisation (SELDI) is a variant of MALDI in which the usual metal targets for MALDI are derivatised (Weinberger S. R., Morris T. S., Pawlak M., Pharmacogenomics 1(4):395-416 "Recent trends in protein biochip technology.", 2000). These surface modifications include derivatisation with anion exchangers, cation exchangers, hydrophobic surfaces or hydrophilic surfaces. When protein or peptide samples are applied to these surfaces, the sample adsorbs to the surface and with appropriate washing steps, fractions of the sample can be selectively removing leaving specific components on the target for further analysis by MALDI TOF mass spectrometry. It is envisaged that this may be a useful technique to apply with the labels of this invention, both for analytical purposes and for separating labelled analytes from unreacted tags, particularly surfaces coated with cation or anion exchange resins. The present invention will be described in further detail by way of example only with reference to the following specific embodiments.

EXAMPLES

Example 1

Synthesis of amine-reactive derivatives of 4-hydroxy-alpha-cyano-cinnamic acid

Two different reactive derivatives of 4-hydroxy-alpha-cyano-cinnamic acid (HCCA) were synthesised. The first derivative prepared was the N-hydroxysuccinimide (NHS) ester of the carboxyl function of HCCA. The NHS ester of HCCA (NHS-HCCA) is an amine reactive derivative (see FIG. 1). The first synthesis was successful and gave good results on the MALDI but the yield of the reaction with peptides was not as good as desired so a second synthesis was devised to provide a derivative of HCCA which incorporated a spacer between the cinnamic acid functionality and the reactive NHS ester group. This second reagent (see FIG. 1) will be referred to as NHS-L-HCCA is also amine reactive.

Example 2

Synthesis of 2-cyano-3-(4-tert-butoxycarbonyloxyphenyl) acrylic acid N-hydroxysuccinimide ester [NHS-HCCA]

The synthesis of NHS-HCCA is shown in FIG. 1. In the first step the hydroxyl function of HCCA is protected followed by activation of the carboxylic acid moiety.

Example 2a

Synthesis of 2-cyano-3-(4-tert-butoxycarbonyloxyphenyl) acrylic acid 5.6 g (30 mmol) of 2-cyano-3-(4-hydroxyphenyl) acrylic acid dissolved in 40 ml acetonitrile were stirred with 4.6 ml (33 mmol) of triethylamine until a clear solution was obtained. 0.2 g (4 mmol) 4-dimethylaminopyridine and 7.3 g (33 mmol) tert-butylpyrocarbonate were then added to the clear solution. After 2 hours reaction (the solution is at that point colourless), the solution was reduced to its half volume and washed with 200 ml of a cold 5% citric acid solution.

The organic layer was extracted by ethyl acetate. After evaporation of the solvent, the product was precipitated from heptane/ethyl acetate.

Yield: 7.4=85% Melting Point: 120-121° C.

Example 2b

Synthesis of 2-cyano-3-(4-tert-butoxycarbonyloxyphenyl) acrylic acid N-hydroxysuccinimide ester 0.95 g (5 mmol) 2-cyan-3-(4-tert-butoxycarbonyloxyphenyl) acrylic acid and 0.6 g (5 mmol) N-hydroxysuccinimide were dissolved in 10 ml acetonitrile. 1.1 g (5.7 mmol) N-ethyl-N'-3-dimethylaminodicyclohexylcarbodiimide hydrochloride were added in portions to the reaction mixture. After 2 hours, the solvent was evaporated. The residue obtained was washed with ethyl acetate and with a cold 5% citric acid solution and then with a saturated NaCl solution. The product was purified by chromatography.

Yield: 1.2 g=63%

Example 3

Synthesis of 2-cyano-3-(4-hydroxyphenyl) acrylic acid (6-[2,5-dioxo-pyrrolidinyl-N-oxy]-6-oxo) hexyl amide [NHS-L-HCCA]

The synthesis of NHS-L-HCCA is shown in FIG. 1. In the first step a chlorinated linker is produced. The chlorine group is then nucleophilically substituted by a cyanide ion. This cyano linker is then condensed with 4-hydroxybenzaldehyde to give a cinnamic acid derivative with a six carbon chain linker with a free carboxyl group that is activated to form an NHS-ester in the final step of the synthesis.

Example 3a

Synthesis of 6-(chloracetamido) hexanoic acid 18 ml (221 mMol) chloracetylchloride was added dropwise to 20 g (153 mmol) 6-aminohexanoic acid dissolved in 80 ml cold NaOH solution (2N) at room temperature (RT). The reaction mixture was stirred for 30 minutes while the pH of the solution was kept between 10-11 with occasional addition of NaOH solution (6N). The pH of the reaction mixture was then altered to pH 5 with HCl (2N) and the residue was filtered. The residue was then washed with water until the pH of the water was neutral. The product, dried over phosphorus pentoxide, was re-dissolved in 300 ml chloroform and filtered to remove the undissolved residue. Heptane was added to the filtrate and a syrup was obtained by stirring under cooling. The product was filtered, dried and was then crystallized from water.

Yield: 20 g=63% Melting Point: 82° C.

Example 3b

Synthesis of 6-(cyanoacetamido) hexanoic acid 2.8 g (20 mmol) potassium hydrogen carbonate were added to 8.3 g (40 mmol) 6-(chloracetamido) hexanoic acid dissolved in 25 ml water. 3.2 g (48 mmol) potassium cyanide was then added to the clear solution which was cooled on ice. The reaction mixture was stirred for 17 hours and was then acidified with HCl (2N). The residue after extraction was purified by chromatography (silica gel, solvent: ethyl acetate).

Yield: 6 g=76% Melting Point: 80-81° C.

Example 3c

Synthesis of 2-cyano-3-(4-hydroxyphenyl) acrylic acid (6-hydroxy-6-oxo-hexyl)amide 7.5 g (38 mmol 6-(cyanacetamido) hexanoic acid was dissolved in 50 ml pyridine. 4.6 g (38 mmol) 4-hydroxybenzaldehyde and 0.7 ml (7 mmol) piperidine were added to the solution and the reaction mixture was stirred for 2 hours at 50° C. A further aliquot of 0.4 ml piperidine was then added to the reaction and the solution was stirred at RT for 60 hours. The residue after evaporation of the pyridine was acidified with HCl (2N) and was extracted with ethyl acetate. The organic layer was poured into 300 ml of a saturated solution of sodium hydrogen carbonate. The aqueous layer was then carefully acidified with HCl (2N). The precipitated residue was filtered and washed with water. The dried product was crystallized from dioxane.

Yield: 8.4 g=74% Melting Point: 178° C.

Example 3d

Synthesis of 2-cyano-3-(4-hydroxyphenyl) acrylic acid (6-[2,5-dioxo-pyrrolidinyl-N-oxy]-6-oxo) hexyl amide 2.3 g (20 mmol) N-hydroxysuccimide and 6.0 g (20 mmol) 2-Cyan-3-(4-hydroxyphenyl) acrylic acid [6-hydroxy 6-oxo-hexyl] amide were dissolved in 200 ml dioxane at 60-70° C. 4.6 g (22 mmol) of dicyclohexylcarbodiimide was added to the reaction mixture which was stirred and cooled to 30° C. This temperature was maintained for one hour. The reaction mixture was then brought to room temperature and stirred for 20 hours. The solution was filtered and evaporated. The residue was treated with dichloromethane and a solution of sodium bicarbonate. The organic layer after extraction was washed with water and dried over sodium sulphate. After evaporation of the solvent, the residue was then chromatographed on silica gel. The product was crystallised from ethyl acetate. To avoid the exothermic reaction caused by depositing the product onto silica gel, the column was first cooled.

Yield: 50 g=63% Melting Point: 142° C.

Example 4

Reaction of NHS-HCCA with Resin-Bound Peptide

The first active ester cinnamic acid mass tag (NHS-HCCA), whose synthesis is described above, was attached to resin bound peptides according to the following procedure.

Target Peptide

The peptide sequence, HRDPYRFDPHKD (SEQ ID NO: 1), was synthesized on a Wang type resin using standard Fmoc/tBu synthesis procedures (see for example Fields G. B. & Noble R. L., Int J. Pept Protein Res 35(3): 161-214, "Solid phase peptide synthesis utilizing 9-flourenylmethoxycarbonyl amino acids." 1990). The resin-bound peptide yields a free acid moiety after cleavage.

NHS—HCCA

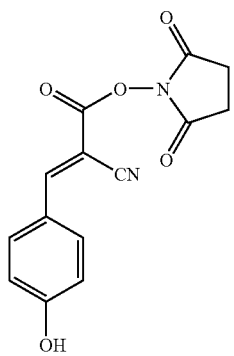

Molecular Weight=286.24

Exact Mass=286.06

Molecular Formula=$C_{14}H_{10}N_2O_5$

Molecular Composition=C 58.7%, H 3.5%, N 9.8%, O 28.0%

Protocol for the Labelling

The resin bound peptide was deprotected at the N-terminus following standard methods (piperidine in DMF) and reacted with an excess of the above reagent NHS-HCCA and with excess of a base (117 mg=0.4 mol in 800 μl DMF with 1 eq.=44.3 mg DIPEA). The mixture was incubated at room temperature for 3 h.

Cleavage and Work-Up

After the labelling, the resin was washed and the peptide was cleaved off of the resin by incubation for 2 hours with the following scavenger mix: TFA:thioanisole:triethylsilane:water; 92.5%:2.5%:2.5%:2.5% respectively. The peptide was precipitated and washed with diethyl ether and lyophilised from tert-butanol/water (4:1) to yield a white powder.

Structure of the Desired Compound

NH—HRDPYRFDPHKD—COOH (SEQ ID NO: 1)

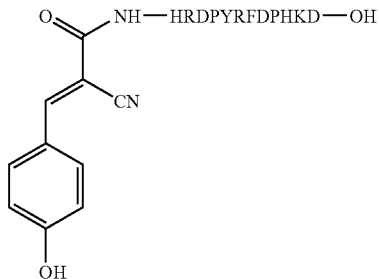

Molecular weight: 1753.87 g/mol (average)/1752.78 g/mol (monoisotopic)

Mono-isotopic composition: $C_{80}H_{104}N_{24}O_{22}$

Example 5

Figure 2:
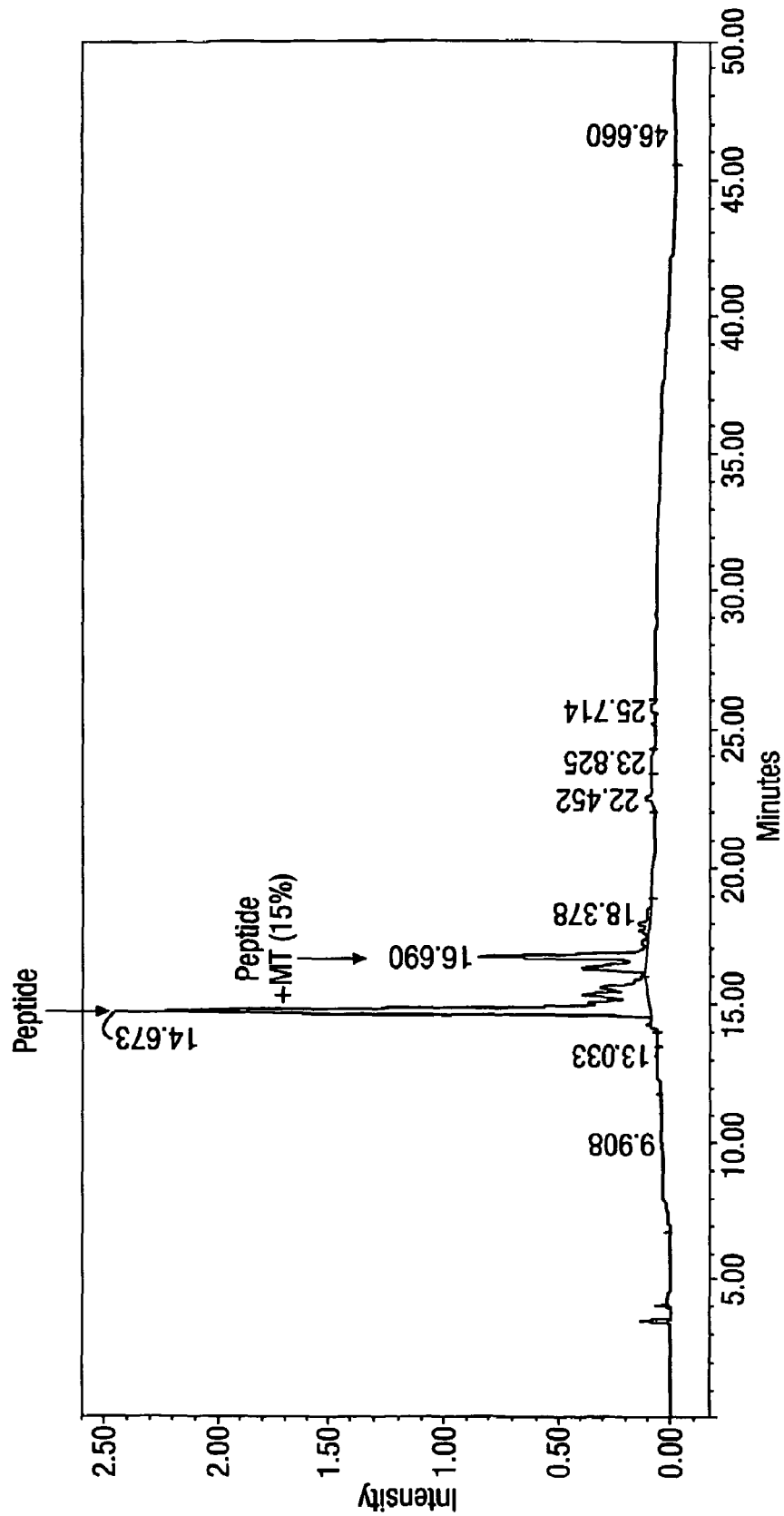
FIG. 2 shows a High Performance Liquid Chromatography (HPLC) trace from the coupling reaction of a reactive tag of this invention with a synthetic peptide (HRDPYRFDPHKD—SEQ. ID NO: 1)
Figure 3:
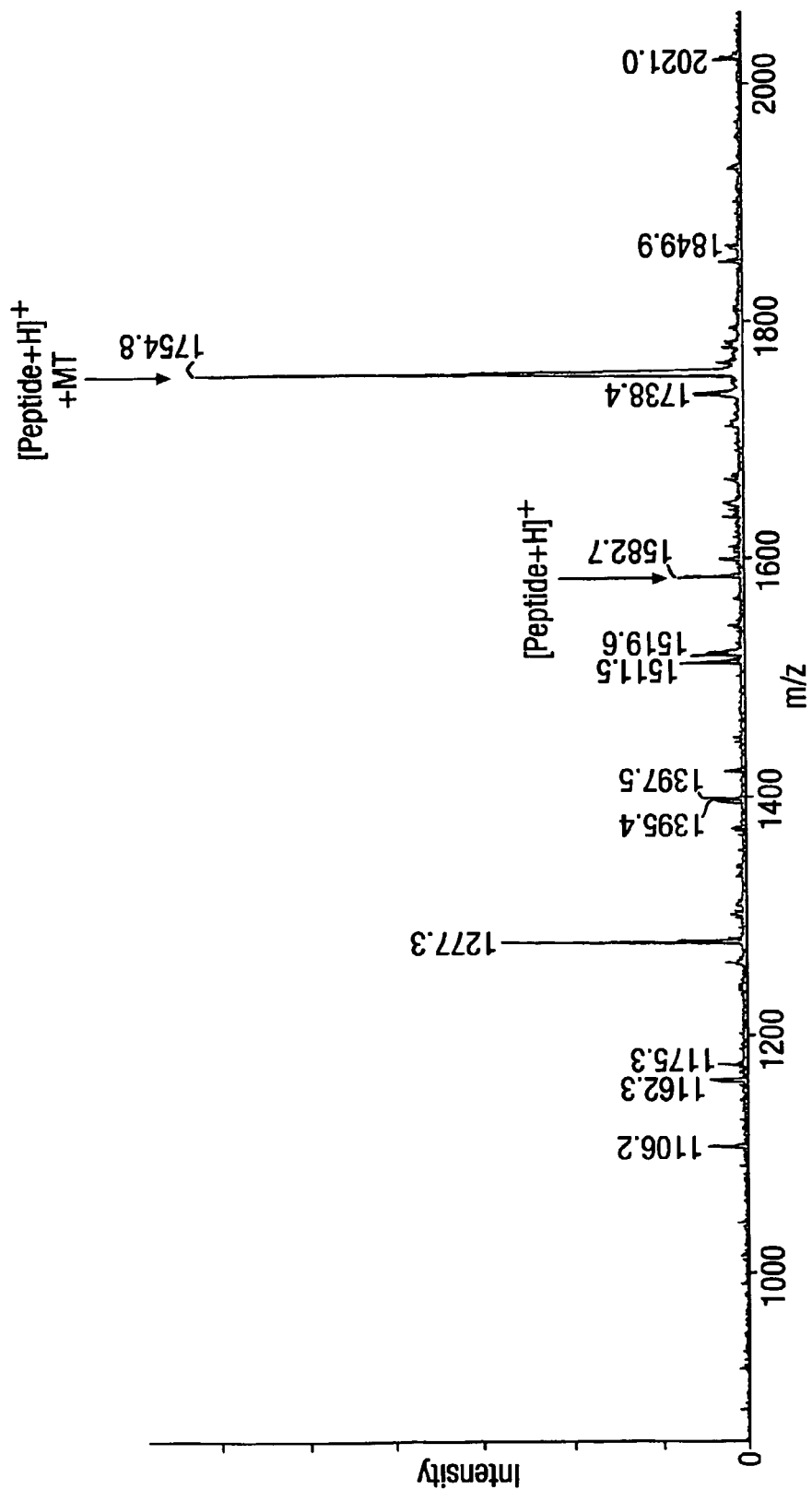
FIG. 3 shows a MALDI TOF MS spectrum of the peptide mixture shown in FIG. 1 (HRDPYRFDPHKD—SEQ ID NO: 1)
Figure 4:
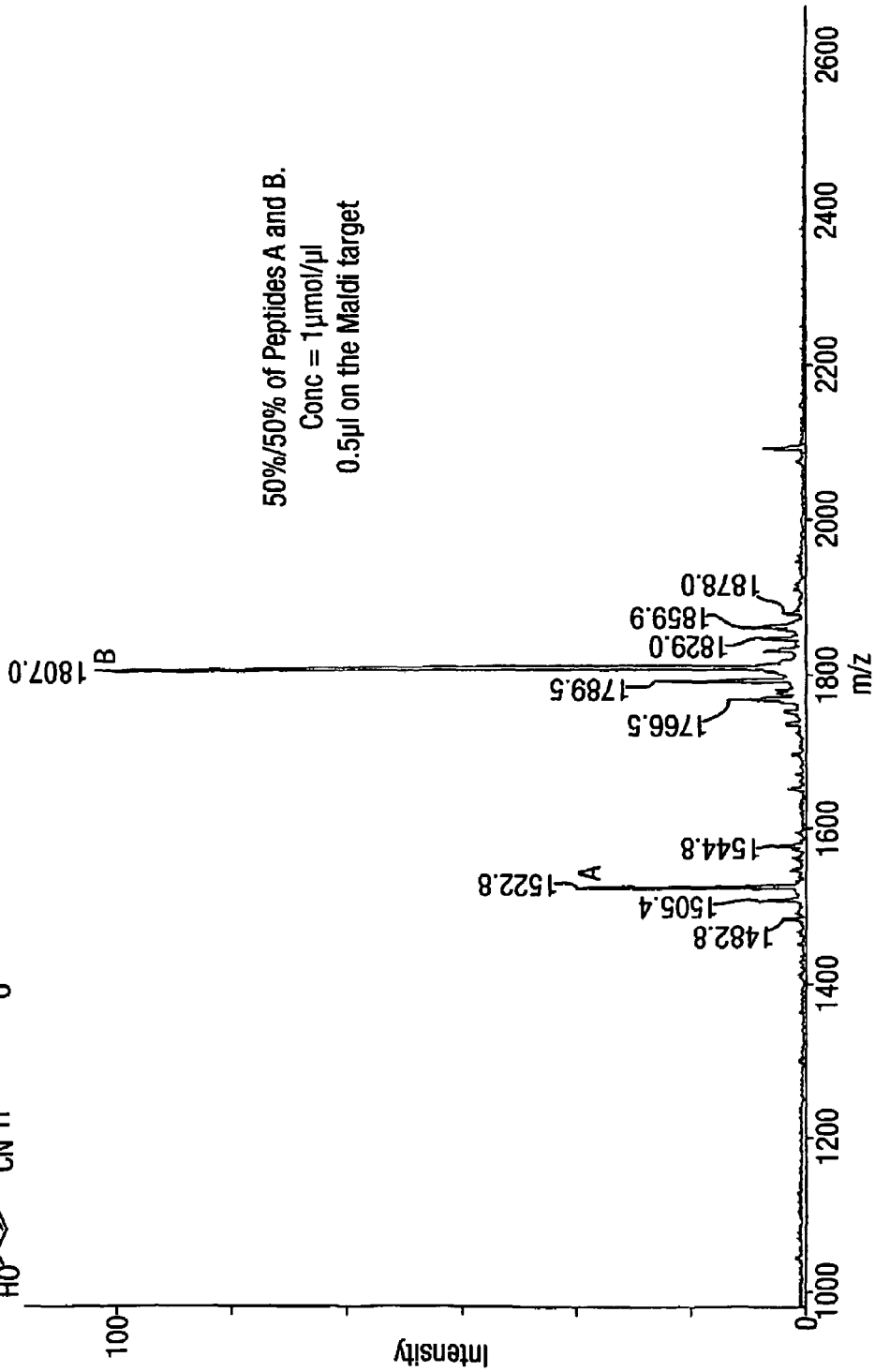
FIG. 4 shows a MALDI TOF MS spectrum from the labelling reaction of a synthetic peptide with a reactive MALDI matrix mass tag that comprises a linker (HSRGHRGHS-HAHRG—SEQ ID NO: 9).

Analysis of NHS-HCCA Labelled Peptide and Comparison with Unlabelled Peptide The product of the labelling reaction was analysed by HPLC (see FIG. 2) and was found to comprise a mixture of labelled and unlabelled peptide. The labelled peptide comprises about 85% of the mixture while the unlabelled peptide comprises about 15% of the mixture. Analysis of the mixture by electrospray ionisation mass spectrometry does not show any improvement in the sensitivity of detection of the labelled peptide however analysis of the mixture by MALDI TOF MS (FIG. 3) shows that the labelled peptide, which is present as a smaller percentage of the mixture is detected with far greater sensitivity than the unlabelled peptide.

Example 6

Reaction of NHS-L-HCCA with Resin-Bound Peptides

The second active ester cinnamic acid mass tag (NHS-L-HCCA) comprising an additional six carbon chain linker, whose synthesis is described above, was attached to resin bound peptides according to the following procedures.

Peptides

The following peptide sequences were synthesised on a Wang type resin using standard Fmoc/tBu synthesis procedures:

| | | |
|---|---|---|
| HSRGARGHSHAHRG (SEQ ID NO: 2) | (highly basic) | M: 1522.62 |
| YDSGEGDESDAYEG (SEQ ID NO: 3) | (highly acidic) | M: 1493.38 |
| LGWSGFGWSFSYLG (SEQ ID NO: 4) | (highly hydrophobic) | M: 1563.75 |

(bound to a trityl type resin to yield a free acid after cleavage)

NHS—L—HCCA

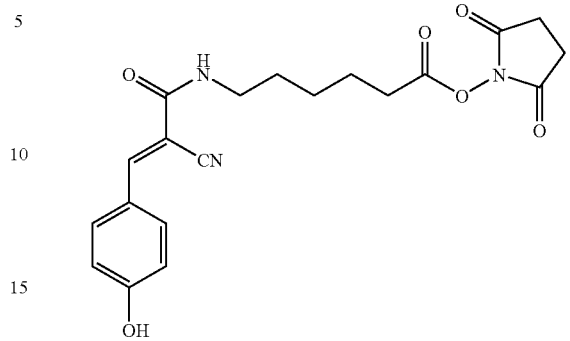

Molecular Weight=399.40

ExactMass=399.14

Molecular Formula=$C_{20}H_{21}N_3O_6$

Molecular Composition=C 60.14%, H 5.30%, N 10.52%, O 24.04%

Protocol for Peptide Labelling

The resin bound peptide was deprotected at the N-terminus following standard methods (piperidine in DMF) and reacted with an excess of the reagent NHS-L-HCCA and with an excess of a base (128 mg=0.4M in 800 µl DMF with 1 eq.=44.3 mg DIPEA). The mixture was incubated at room temperature for 3 hours.

Cleavage and Work-Up

After the labelling reaction, the resin was washed and the peptides were cleaved from the resin by incubation for 2 hours with the following scavenger mix: TFA 92.5%/thioanisole; 2.5%/triethylsilane; 2.5%/water; 2.5%. The peptides were precipitated and washed with diethyl ether. Finally, the peptides were lyophilised from tert-butanol/water (4:1) to yield a white powder.

Structure of the Desired Compounds

NH—HSRGARGHSHAHRG—COOH

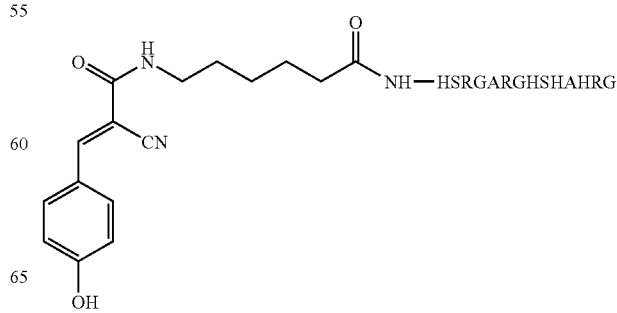

Molecular weight: 1806.94 g/mol (average)/1805.87 g/mol (mono-isotopic)

Mono-isotopic composition: $C_{76}H_{111}N_{33}O_{20}$

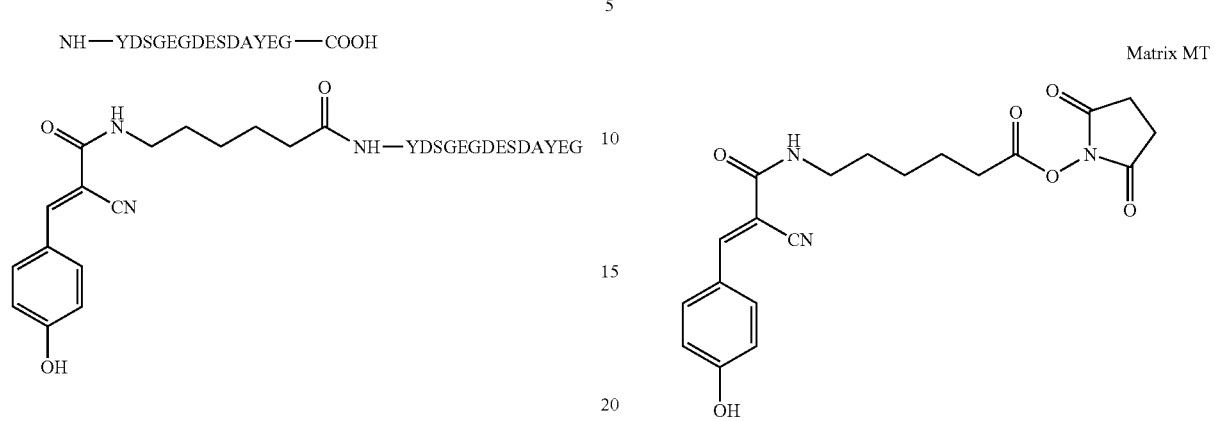

Molecular weight: 1777.70 g/mol (average)/1776.63 g/mol (mono-isotopic)

Mono-isotopic composition: $C_{76}H_{96}N_{16}O_{34}$.

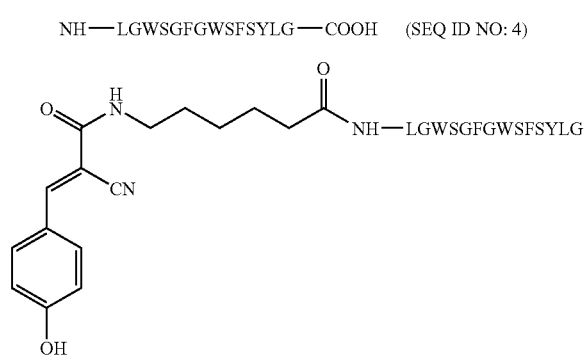

Molecular weight: 1848.06 g/mol (average)/1846.84 g/mol (mono-isotopic)

Mono-isotopic composition: $C_{94}H_{114}N_{18}O_{22}$.

Example 6

Analysis of NHS-L-HCCA Labelled Peptide and Comparison with Unlabelled Peptide

The peptides were analysed by HPLC. The first peptide, HSRGARGHSHAHRG (SEQ ID NO: 2), was isolated pure as the reaction with the tag containing the linker went to completion. The labelled peptide was combined with unlabelled peptide to give a 50/50 mixture at a concentration of 1 μmol/μl of each peptide. Analysis of the mixture by electrospray ionization mass spectrometry does not show any improvement in the sensitivity of detection of the labelled peptide compared to the unlabelled peptide. However, 0.5 μl of the mixture on a metal target analysed by MALDI TOF MS shows that the labelled peptide is detected with greater sensitivity than the unlabelled peptide. This indicates that the linker functionality does not reduce the effectiveness of the tag and can be used to improve the yield of the labelling reaction.

Example 7

Reaction of NHS-L-HCCA with Beta-MSH Peptides

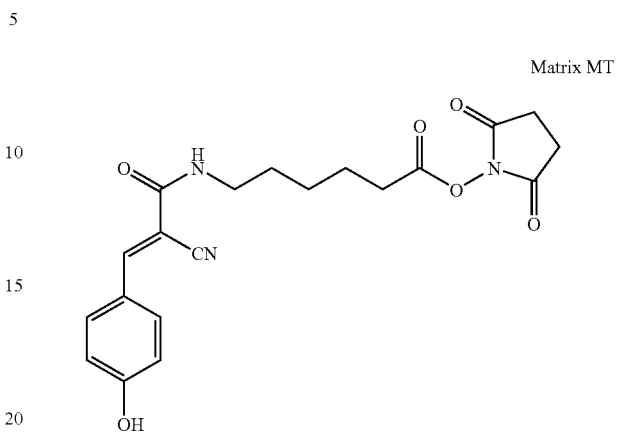

Molecular Formula of NHS-L-HCCA: $C_{20}H_{21}N_3O_6$

Molecular Weight: 399.41

Peptide Labelling in Solution

Protein: β-MSH (DEGPYKMEHFRWGSPPKD, M: 2175) 1 mg (0.46 μmol) peptide is dissolved in water/acetonitrile (250 μl, 90/10). 30 μg trypsin in borate buffer (100 μl, pH 8.0) are added to the peptide solution. The digestion is carried out for 18 h at 37° C.

2.5 mg (6.3 mmol) NHS-L-HCCA in 250 μL acetonitrile are added to 175 μl (½ of the digest solution) of the tryptic peptide solution. The labelling reaction is carried out for 5 h at RT and at pH 7.5. The reaction is then quenched by adding 100 μl H$_2$O/acetonitrile (95/5) and 1% TFA. The labelled peptide solution is then experimented in MALDI MS.

Example 8

Comparison of Spectra from AHS-L-HCCA Labelled Beta-MSH Peptides with Unlabeled Beta-MSH Peptides Peptide Mass Fingerprints from Beta-MSH Tryptic digest of unlabeled beta-MSH gives rise to 3 fragments as shown in Table 2 below.

TABLE 2

| m/z | | Fragment Cleavage Positions | | Composition | |
|---|---|---|---|---|---|
| Isotopic Mass | Average Mass | | | No. of reactive | |
| (Daltons) | (Daltons) | Start | Finish | groups | Sequence |
| 708.3204 | 708.7507 | 1 | 6 | 2 | DEGPYK (SEQ ID NO: 6) |
| 719.3299 | 719.8458 | 7 | 11 | 2 | MEHFR (SEQ ID NO: 7) |
| 786.3786 | 786.8682 | 12 | 18 | 2 | WGSPPKD (SEQ ID NO: 8) |

Tryptic digest of labelled beta-MSH gives rise to 3 fragments as shown in Table 3 below.

TABLE 3

| m/z Isotopic Mass | Fragment Cleavage Positions | | Composition | |
|---|---|---|---|---|
| | | | No. of tagged reactive | |
| (Daltons) | Start | Finish | groups | Sequence |
| 992.435 | 1 | 6 | 1 | DEGPYK + 1 tag (SEQ ID NO: 6) |
| 1276.535 | 1 | 6 | 2 | DEGPYK + 2 tags (SEQ ID NO: 6) |
| 1003.445 | 7 | 11 | 1 | MEHFR + 1 tag (SEQ ID NO: 7) |
| 1287.560 | 7 | 11 | 2 | MEHFR + 2 tags (SEQ ID NO: 7) |
| 1354.609 | 12 | 18 | 2 | WGSPPKD + 2 tags (SEQ ID NO: 8) |

Various experiments were performed on the above labelled and unlabelled digests. A schematic of the labelling protocol for beta-MSH is shown in FIG. 5a. FIG. 5b shows the MALDI TOF mass spectrum of the unlabelled and undigested peptide.

FIG. 6 shows spectra MALDI TOF for the unlabelled and labelled digests of beta-MSH. It can be seen that the 3 expected peptides for the unlabeled digest are present in the spectrum of the unlabeled peptides. The labelled peptide spectrum shows 4 different species. The peptide comprising amino acids 1 to 6 has 2 sites available for labelling; the alpha-amino group and the lysine epsilon amino group. Both of these appear to be fully labelled and only one species corresponding to the doubly labelled peptide appears in the spectrum. Similarly, the peptide comprising amino acids 12 to 18 has 2 sites available for labelling; the alpha-amino group and the lysine epsilon amino group and again both appear to be fully labelled and only one species corresponding to the doubly labelled peptide appears in the spectrum. The peptide comprising amino acids 7 to 11 should only label at the alpha-amino group but appears to have been labelled twice in the mass spectrum as 2 species corresponding to this peptide are detected in the spectrum of the labelled fragments. There is a minor side-reaction where the NHS-L-HCCA reacts with histidine giving rise to a second peak in the spectrum for this peptide.

The singly labelled peptide comprising amino acids 7 to 11 of beta-MSH appeared most strongly in the spectrum of the labelled protein. This peptide fragment was isolated by HPLC chromatography and solutions of this peptide were prepared. FIG. 7 shows MALDI TOF mass spectra of this peptide mixed in various molar ratios with the digest of unlabelled beta-MSH. It can clearly be observed that the detected abundance of the labelled peptide is greater than the unlabelled peptides even at the lowest ratio of labelled to unlabelled peptides (5:95).

FIG. 8 shows the results of a further experiment to demonstrate the enhancement in sensitivity provided by the tags of this invention. FIG. 8 shows a number of MALDI TOF mass spectra for a serial dilution of a stock solution of 44 pmol of the labelled peptide comprising amino acids 7 to 11 of beta-MSH mixed with 180 pmol of digested and unlabeled beta-MSH. The first spectrum shows the MALDI TOF analysis of the stock solution. Both the labelled peptide and the unlabeled peptides can be seen in various dilutions of the stock solution (spectra not shown) until a 625-fold dilution is reached, which is the second spectrum shown in FIG. 8. Labelled and unlabelled peptides can still be seen at this dilution but noise can be seen in the low mass ranges of the spectrum. A further 5-fold dilution to a dilution of 3125-fold gives a spectrum in which the unlabeled peptides can no longer be detected but the labelled peptide is still detectable. The labelled peptide is still detectable in a further 5-fold dilution of the solution (15625-fold). The above results all indicate that there is a significant enhancement in the sensitivity of detection of peptides when covalently attached to a tag comprising a MALDI matrix.

Example 9

Peptide Mass Fingerprinting Experiments with Proteins

A further set of experiments with whole proteins were carried out. The proteins bovine serum albumin (BSA) and glyceraldehyde 3-phosphate dehydrogenase (GAPDH) were analysed individually.

Labelling of Tryptic Digests of BSA and GAPDH:

| BSA (Probe A): | 69.2 kDa/60 * Lys/26 * Arg |
|---|---|
| GAPDH (Probe B): | 35.7 kDa/26 * Lys/10 * Arg |

A stock solution of 2 µg/µl protein in borate buffer (50 mmol, pH 8) and urea/thiourea (100 mmol, 2/1) is freshly prepared. 20 µl (1 µg/µl) trypsin are added to 260 µl of protein stock solution. The enzymatic cleavage reaction is carried out for 16 h at 37° C., pH 8.0

160 µl of the tryptic peptide solution are labelled with 2.5 mg NHS-L-HCCA dissolved in 250 µl acetonitrile. After 5 hours labelling at 25° C., pH 7.8, the reaction is then quenched by adding 100 µl H$_2$O/acetonitrile (95/5)+1% TFA.

Example 10

Comparison of Spectra from NHS-HCCA Labelled BSA Peptides with Unlabeled BSA Peptides FIG. 9 shows a typical MALDI TOF peptide mass fingerprint mass spectrum for BSA. The mass determined in this spectrum can be used to search a database of known and predicted mass spectra to identify the protein from its component tryptic peptide fragment masses. FIG. 10 shows the results of a search of the SWISS-PROT database, with some of the masses from the spectrum shown in FIG. 10, using the MS-Fit program on the ProteinProspector database server. This tool is available on the world wide web and allows the identification of proteins with modified amino acids (Clauser K. R, Baker P. R. and Burlingame A. L., Analytical Chemistry, Vol. 71(14): 2871, "Role of accurate mass measurement (+/−10 ppm) in protein identification strategies employing MS or MS/MS and database searching." (1999)). The modified amino acid masses are entered into the program along with a series of modified peptide masses. The output of the program is a list of proteins that contain peptides that match the masses submitted to the database. The matching peptides for each matching protein, identified by MS-Fit, can then be displayed to determine how well the peptides match the protein, which is shown in FIG. 10. This analysis was performed with unmodified lysine.

FIG. 11 shows the corresponding MALDI TOF peptide mass fingerprint mass spectrum for NHS-L-HCCA labelled BSA. FIG. 12 shows the peptides that match BSA from a search of the SWISS-PROT database using the MS-Fit program, in which the appropriately modified lysine mass has been entered, along with peptide masses from the spectrum in FIG. 11.

FIG. 13 shows a typical MALDI TOF peptide mass fingerprint mass spectrum for GAPDH. The mass determined in this spectrum can be used to search a database of known and predicted mass spectra to identify the protein from its component tryptic peptide fragment masses. FIG. 14 shows the results of a search of the SWISS-PROT database, with some of the masses from the spectrum shown in FIG. 13, using the MS-Fit program, where unmodified lysine is searched for.

FIG. 15 shows the corresponding MALDI TOF peptide mass fingerprint mass spectrum for NHS-L-HCCA labelled BSA. FIG. 16 shows the peptides that match GAPDH from a search of the SWISS-PROT database using the MS-Fit program, in which the appropriately modified lysine mass has been entered, along with peptide masses from the spectrum in FIG. 15.

Example 11

Preparation of Exemplary Tags

The following examples show the syntheses of further novel tags, shown in FIGS. 17a-17d, provided by this invention. These tags all include an ionisable functionality. Ionisable functionalities serve several useful purposes. Ionisable functionalities improve the solubility of the tags in aqueous solvents and buffers. Ionisable functionalities can act as affinity ligands allowing unreacted tag to be separated from labelled analytes using ion exchange resins. The sulphonic acid moiety has an affinity to anion exchange resins while the positively ionising groups all have an affinity for cation exchange resins. In addition, ionisable functionalities promote ionisation in the mass spectrometer. The tag shown in FIG. 17a comprises a sulphonic acid functionality. The tags in FIGS. 17b and 17c comprise a guanidino functionality, while the tag in FIG. 17d comprises a tertiary amino functionality.

Synthesis of 6-[2-Cyano-3-(4-hydroxy-3-sulfonato-phenyl)-acryloylamino]-hexanoic acid-(2,5-dioxo-pyrrolidin-1-yl)-ester Sodium The synthesis of the tag compound shown in FIG. 17a is now described. The intermediates are numbered according to the scheme shown in FIG. 18.

6-(2-Chloroacetylamino)-hexanoic acid (5)

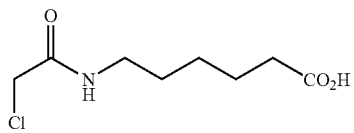

20 g (153 mMol) 6-Amino-hexanoic acid was mixed with 80 ml of 2N Sodium Hydroxide (NaOH). 18 ml (221 mMol) of Chloro-acetylchloride and 6N NaOH were added to the mixture at Room Temperature (RT). The pH of the reaction mixture was maintained between 10 and 11 during the addition of Chloro-acetylchloride and 6N NaOH by using a burette to control the addition. The mixture was stirred for 30 mins at this constant pH. Ethyl acetate (EtOAc) was then added to the reaction mixture and the pH was adjusted to 2 with 2N Hydrochloric Acid (HCl). To work up the product, the EtOAc-layer was separated and the aqueous phase was extracted with EtOAc. The organic layers were dried and the solvent was evaporated. The residue was then re-crystallized from diisopropylether/EtOAc (1:1, v:v).

Yield: 25.3 g (80%); Mp 82° C.

6-(2-Cyano-acetylamino)-hexanoic acid (1)

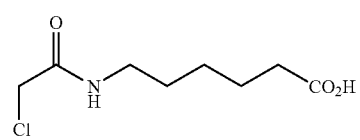

8.3 g (40 mMol) 6-(2-Chloro-acetylamino)-hexanoic acid 5 was dissolved with 2.8 g (20 Mol) $K_2CO_3$ in 25 ml water at RT. After having added 3.2 g (48 mMol) KCN, the reaction mixture was stirred for 17 h at RT. The pH of the solution was then altered to 2 with 2N HCl and the product was extracted with EtOAc. After drying the product over sodium sulphate and evaporating the solvent, the product was purified by chromatography using ethyl acetate. The compound was then re-crystallized from EtOAc.

Yield: 6 g (76%); Mp 90° C. HPLC: 97% [LiChrospher 100, RP 18, (5 μm); $CH_3CN$: ($H_2O$+0.01M TBAS)=40:60, flow 1 ml/Min.; 2.4 Min.] $^1$H-NMR ($d_6$DMSO) δ 1.23-1.50 (m, m, m, 6H, N—C—$(CH_2)_3$—C—CO); 2.18 (t, 2H, $CH_2$—$CO_2$); 3.05 (m, 2H, N—$CH_2$); 3.56 (s, 2H, NC—$CH_2$); 8.15 (t, 1H, NH); 11.94 (s, 1H, OH)

6-(2-Cyano-acetylamino)-hexanoic acid (1)

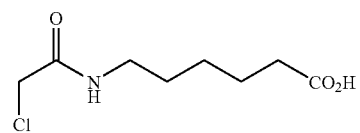

6.55 g (50 mMol) 6-Amino-hexanoic acid and 9.2 g (110 mMol) $NaHCO_3$ were dissolved in 80 ml water. A solution of 9.1 g Cyanoacetic acid-(2,5-dioxo-pyrrolidine-1-yl)-ester [C. Bartolucci et al., 47, 1367 (1992)] was added in portions to the mixture at RT. After stirring the reaction mixture for 16 h at RT, the pH of the solution was altered to 2 with 2N HCl and the product was extracted with ethyl acetate. The organic layer was dried over sodium sulphate and the solvent was then evaporated. The compound was then re-crystallized from EtOAc.

Yield: 5 g (51%); Mp: 95° C. HPLC: >98% [LiChrospher 100, RP 18, (5 μm); $CH_3CN$: ($H_2O$+0.01M TBAS)=40:60, flow 1 ml/Min.; 2.4 Min.] $^1$H-NMR ($d_6$DMSO) δ 1.23-1.50 (m, m, m, 6H, N—C—$(CH_2)_3$—C—CO); 2.18 (t, 2H, $CH_2$—$CO_2$); 3.05 (m, 2H, N—$CH_2$); 3.56 (s, 2H, NC—$CH_2$); 8.15 (t, 1H, NH); 11.94 (s, 1H, OH)

Sodium 3-Formyl-6 hydroxy-phenyl-sulfonate (7)

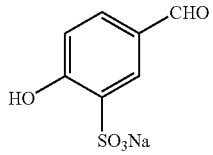

7

20 g (164 mMol) 4-Hydroxybenzaldehyde was dissolved in 100 mM conc. $H_2SO_4$ and the solution was stirred for 20 h at 80° C. The cooled solution was then poured onto 350 g ice. After adding 60 g Sodium Chloride (NaCl), a crystallized colourless product formed after a short time. After cooling to 0° C., the product was filtered off and was washed twice with 50 ml saturated NaCl solution. The solid residue was then heated in 150 ml saturated NaCl solution, cooled down and filtered off. The residue was washed again twice with 25 ml saturated NaCl solution and twice with 15 ml ice-cold water. The sodium salt was obtained by slurrying the product in 150 ml water and by neutralisation the solution to pH 7.2 with 2N NaOH. At this point, traces of starting material in the solution (aldehyde adduct) could be extracted with ethyl acetate. The aqueous layer was treated with A-Kohle, filtered off and the solution was evaporated under vacuum. The dried solid residue was treated with acetone and filtered off.

Yield: 30.5 g (83%)
$R_f$=0.48 (EtOAc/AcOH=2:1)
HPLC: >98% [LiChrospher 100, RP 18, (5 µm) Merck# 50377; $CH_3CN$: ($H_2O$+0.01M TBAS)=40:60, flow 1 ml/Min.; 5.2 Min.]
$^1$H-NMR ($d_6$DMSO) δ 6.53 (d, 1H, 5-H-Ph); 7.50 (m, 1H, 4-H-Ph); 7.92 (d, 1H, 2-H-Ph); 9.50 (s, 1H, OH)

Sodium 6-[2-Cyano-3-(4-hydroxy-3-sulfonato-phenyl)-acryloylamino]-hexanoic acid (2)

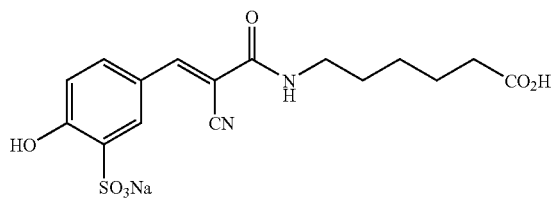

2

17.85 g (90 mMol) 6-(2-Cyano-acetylamino)-hexanoic acid (1) and 17.92 g (80 mMol) Sodium 3-Formyl-6 hydroxy-phenyl-sulfonate (7) were stirred in 160 ml Pyridine and 1.6 ml Piperidine for 3 days at 65° C. The reaction mixture was diluted with 200 ml Acetonitrile and the residue was filtered off and washed with Acetonitrile and Acetone. The solid residue was heated in 150 ml Acetonitrile for 1 h, cooled down and filtered off.

Yield: 28 g (86%) HPLC: 93% [LiChrospher 100, RP 18, (5 µm) Merck# 50377; $CH_3CN$: ($H_2O$+0.01M TBAS)=40:60, flow 1 ml/Min.; 6.3 Min.]$^1$H-NMR ($D_2O$) δ 1.29-1.36 u. 1.53-1.60 (m, m, 6H, N—C—$(CH_2)_3$—C—CO); 2.14-2.19 (m, 2H, $CH_2$—$CO_2$); 3.25-3.28 (m, 2H, N—$CH_2$); 6.73 (d, 1H, 5-H-Ph); 7.80 (m, 1H, 6-H-Ph); 8.30 (d, 1H, 2-H-Ph); 7.92 (s, 1H, CH=C—CN)

Sodium 6-[2-Cyano-3-(4-hydroxy-3-sulfonato-phenyl)-acryloylamino]-hexanoic acid-(2,5-dioxo-pyrrolidine-1-yl)-ester (3)

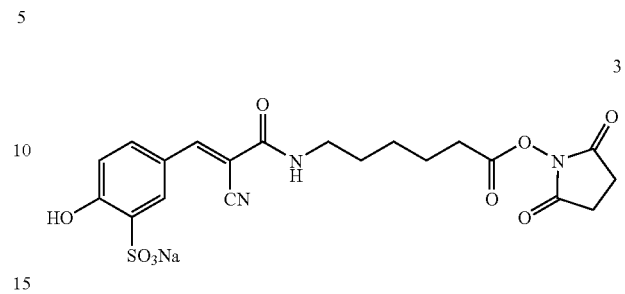

3

9.2 g (80 mMol) N-Hydroxy-succinimide was melt at 90-100° C. (water bath temperature). 4.04 g Sodium (10 mMol) 6-[2-Cyano-3-(4-hydroxy-3-sulfonato-phenyl)-acryloylamino]-hexanoic acid 2 was added in portions to the molten residue and the mixture was stirred to get a homogenous phase. After adding 15 mg DMAP to the reaction mixture, a solution of 4.12 g (20 mMol) Dicyclohexylcarbodiimide dissolved in 50 ml Acetonitrile was added drop-wise to the reaction mixture and the solution obtained was heated under reflux for 1 h. Then, a further 100 ml of Acetonitrile was added to the solution. The solid residue was filtered off and the filtrate was evaporated. The residue recovered from the filtrate was dissolved in acetone and separated from any insoluble residue. The solution was reduced to ca. 50 ml and the product was precipitated by adding 250 ml EtOAc. The precipitated product was dissolved in water and the aqueous layer was extracted several times with EtOAc. The aqueous phase was then lyophilised.

Yield: 1.42 g (28%) HPLC: >90% [Lichrosorb RP 18, (5 µm) Merck# 50333; $CH_3CN$: ($H_2O$+0.01M TBAS)=40:60, flow 1 ml/Min.; 10.3 Min.]$^1$H-NMR ($D_2$) δ 1.39-1.67 (m, m, m, 6H, N—C—$(CH_2)_3$—C—CO); 2.69 (t, 2H, $CH_2$—$CO_2$); 2.80 (s, 4H, OSu); 3.18-3.20 (m, 2H, N—$CH_2$); 6.97 (d, 1H, 5-H-Ph); 7.92 (m, 1H, 6-H-Ph); 8.13 (d, 1H, 2-H-Ph); 8.03 (s, 1H, CH=C—CN); 8.31 (t, 1H, NH); 11.22 (s, 1H, OH)

Synthesis of $N^α$-[2-Cyano-3-(4-hydroxyphenyl)-acryloyl]-Arg$^{ωω'}$(Boc$_2$)-2,5-dioxo-pyrrolidine-1-yl ester The synthesis of the tag compound shown in FIG. 17b is now described. The intermediates are numbered according to the scheme shown in FIG. 19.

$N^α$-(2-Cyano-acetyl)-Arg$^{ωω'}$(Boc2)-OH (2)

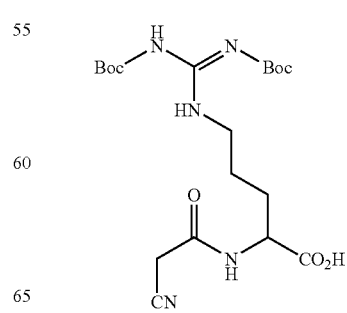

2

4 g (5 mMol) Cu[Arg$^{\omega\omega'}$(Boc$_2$)]$_2$ [M, Bernatowicz et al., Synth. Commun. 23, 3055 (1993)], 2.74 g (6 mMol) EDTA.4Na.H$_2$O and 1.97 g (23.5 in Mol) NaHCO$_3$ were dissolved in 19 ml water. A solution of 2.18 g (11.96 in Mol) 2-Cyano-acetic acid-OSu-ester dissolved in 46 ml Acetone was added drop-wise to the reaction mixture at RT. The mixture was then stirred for 16 h. The acetone layer was evaporated and the pH of the aqueous layer was adjusted to 3 with a 5% KHSO$_4$-solution. The product was extracted with EtOAc. After having dried the organic layer and evaporated the solvent, the product was purified by chromatography using CH$_2$Cl$_2$/CH$_3$OH (10:1, v:v).

Yield: 2.2 g (50%) HPLC: 96% [LiChrospher 100 RP 18, (5 μm) Merck# 50377; CH$_3$CN: (H$_2$O+0.01M TBAS)=90:10, flow 1 ml/Min.; 2.5 Min.]

N$^\alpha$-[2-Cyano-3-(4-hydroxyphenyl)-acryloyl]-Arg$^{\omega\omega'}$(Boc$_2$)-OH (3)

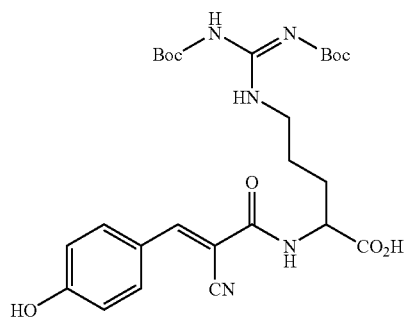

3

19.5 g (44 mMol) N$^\alpha$-(2-Cyano-acetyl)-Arg$^{\omega\omega'}$(Boc$_2$)-OH 2 and 5.37 g (4 mMol) 4-Hydroxy-benzaldehyde was added to 60 ml Pyridine with 0.9 ml Piperidine. The mixture was heated to 50° C. for 2 h and was then stirred for 16 h at RT. Pyridine was evaporated under vacuum and the pH of the solution obtained was altered to 3 with a 5% KHSO$_4$ solution. After extracting the residue with EtOAc and drying the organic layer over MgSO$_4$, the solvent was evaporated. The product was purified by chromatography using CH$_2$Cl$_2$/CH$_3$OH (100:3, v:v).

Yield: 14.2 g (59%) HPLC: >98% [LiChrospher 100 RP 18, (5 μm) Merck# 50377; CH$_3$CN: (H$_2$O+0.01M TBAS)= 90:10, flow 1 ml/Min.; 2.6 Min.]$^1$H-NMR (d$_6$-DMSO) δ 1.37 u. 1.45 (s, s, 18H, 2×t-Bu); 1.45-1.88 (m, 4H); 3.32 (m, 2H, N—CH$_2$); 4.31 (m, 1H, N—CH); 6.94 u. 7.88 (m, m, 4H, Ph); 8.06 (s, 1H, CH=C—CN); 8.31, 8.45, ~10.4, 11.5 u. 12.6 (5H, 3×NH, 2×OH)

N$^\alpha$-[2-Cyano-3-(4-hydroxyphenyl)-acryloyl]-Arg$^{\omega\omega'}$(Boc$_2$)-2,5-dioxo-pyrrolidine-1-yl ester (4)

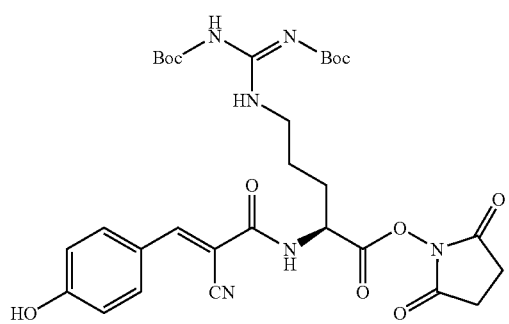

4

2.71 g (5 mMol) N$^\alpha$-[2-Cyano-3-(4-hydroxyphenyl)-acryloyl]-Arg$^{\omega\omega'}$(Boc$_2$)-OH 3 and 0.58 g (5 mMol) N-Hydroxy-succinimide were dissolved in 50 ml CH$_2$Cl$_2$. 1.03 g (5 mMol) Dicyclohexyl-carbodiimide was added to the reaction mixture and the solution was stirred for 20 h at RT. The precipitate was filtered off and the filtrate was evaporated. The residue obtained was dissolved in EtOAc. The EtOAc layer was washed twice with NaHCO$_3$-solution, twice with 5% Citric acid and twice with saturated NaCl-solution, dried over MgSO$_4$ and the solvent was then evaporated. The remaining solid foam was dissolved in ca. 5 ml EtOAc and ca. 50 ml Diethylether was carefully added to this solution until the solution became turbid. A-Kohle was then mixed to the mixture, stirred and filtered off. The filtrate was evaporated and the remaining residue was treated with Diisopropylether and then filtered off Yield: 1.58 g (50%) $^1$H-NMR (CDCl$_3$) δ 1.32 u. 1.43 (s, s, 18H, 2×t-Bu); 1.57-2.04 (m, 4H); 2.78 (s, 4H, O-Su); 3.25-3.67 (m, 2H, N—CH$_2$); 4.88 (m, 1H, N—CH); 6.88 u. 7.76 (m, m, 4H, Ph); 8.04 (s, 1H, CH=C—CN); 7.21, 8.49, ~8.75, 11.45 (4H, 3×NH, OH) MS: 643 (M+1)

Synthesis of N$^\alpha$-[2-Cyano-3-(4-hydroxyphenyl)-acryloyl]-Arg-$^{\omega\omega'}$(Boc$_2$)-N-(6-amino-hexanoic acid-OSu-ester)

The synthesis of the tag compound shown in FIG. 17c is now described. The intermediates are numbered according to the scheme shown in FIG. 20.

N$^\alpha$-[2-Cyano-3-(4-hydroxyphenyl)-acryloyl]-Arg-$^{\omega\omega'}$(Boc$_2$)-N-(6-amino-hexanoic acid) (2)

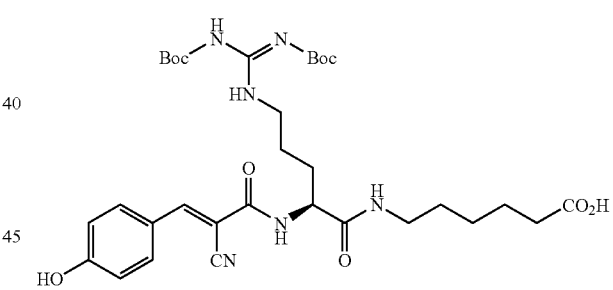

2

5.42 g (10 mMol) N$^\alpha$-[2-Cyano-3-(4-hydroxyphenyl)-acryloyl]-Arg-$^{\omega\omega'}$(Boc$_2$)-OH (1) and 1.15 g (10 mMol) N-Hydroxy-succinimide were dissolved in 100 mL Dichloromethane. 2.06 g (10 mMol) Dicyclohexyl-carbodiimide was added to the solution and the reaction mixture was stirred for 20 h at RT. The precipitate was filtered off and the filtrate was evaporated. The crude active ester product obtained from (1) was then dissolved in 45 ml THF. An aqueous solution of 1.31 g (10 mMol) 6-Amino-hexanoic acid and 0.84 g (10 mMol) NaHCO$_3$ was added to the reaction mixture. After having stirred the reaction mixture for 20 h at RT, the pH of the solution was altered to 3 with a 2N HCl solution and the product was extracted with EtOAc. The organic layer was then dried and evaporated. The residue was purified by chromatography using EtOAc/Diisopropylether (1:1,v:v).

Yield: 2.6 g (40%) HPLC: >98% [Lichrosorb RP 18, (5 μm) Merck# 50333; CH$_3$CN: (H$_2$O+0.01M TBAS)=55:45, flow 1 ml/Min.; 4.1 Min.]$^1$H-NMR (CDCl$_3$) δ 1.43 u. 1.48 (s, s, 18H, 2×t-Bu); 1.30-1.73 (m, 10H); 1.74-1.85 (m, 1H);

1.85-1.97 (m, 1H); 2.34 (m, 2H); 3.15-3.39 (m, 2H); 3.45 (m, 2H); 4.51 (m, 1H); 6.92 u. 7.76 (m, m, 4H, Ph); 8.0 (s, 1H, CH=C—CN); 7.03, 7.26, 8.55, 9.5 (4H, 3×NH, OH)

N$^\alpha$-[2-Cyano-3-(4-hydroxyphenyl)-acryloyl]-Arg-$^{\omega\omega'}$(Boc$_2$)-N-(6-amino-hexanoic acid-OSu-ester) (3)

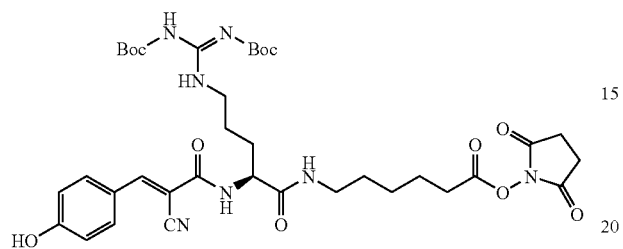

2.63 g (4 mMol) N$^\alpha$-[2-Cyano-3-(4-hydroxyphenyl)-acryloyl]-Arg-$^{\omega\omega'}$(Boc$_2$)-N-(6-amino-hexanoic acid) (2) and 0.46 g (4 mMol) N-Hydroxy-succinimide were dissolved in 50 ml CH$_2$Cl$_2$. Then, 0.91 g (4.4 mMol) Dicyclohexyl-carbodiimide was added to the solution and the reaction mixture was stirred for 20 h at RT. The precipitate was filtered off and the filtrate was evaporated. The residue obtained was then dissolved in EtOAc and the organic solution was washed with NaHCO$_3$ solution and water. After having dried and evaporated the organic layer, the residue was rapidly purified by chromatography using a short silica gel column and EtOAc under modest pressure.

Yield: 1.53 g (50%)
RF=0.56 (EtOAc)
HPLC: 95% [Lichrosorb RP 18, (5 µm) Merck# 50333; CH$_3$CN: (H$_2$O+0.01M TBAS)=55:45, flow 1 ml/Min.; 6.1 Min.] $^1$H-NMR (CDCl$_3$) δ 1.45 u. 1.49 (s, s, 18H, 2×t-Bu); 1.40-1.98 (m, 11H); 2.6 (t, 2H); 2.85 (s, 4H, OSu); 3.24-3.37 (m, 2H); 3.38-3.57 (m, 2H); 4.54 (m, 1H); 6.92 and 7.77 (m, m, 4H, Ph); 8.01 (s, 1H, CH=C—CN); 6.85, 7.09, 8.53, 11.45 (4H, 3×NH, OH)

Synthesis of 4-[2-Cyano-3-(4-hydroxy-phenyl)-acryloyl]-1-[5-(2,5-dioxo-pyrrolidine-1-yloxycarbonyl)-pentyl]-piperazine-1-ium hydrochloride The synthesis of the tag compound shown in FIG. 17*d* is now described. The intermediates are numbered according to the scheme shown in FIG. 21.

4-Boc-1-(5-ethoxycarbonyl-pentyl)-piperazine (2)

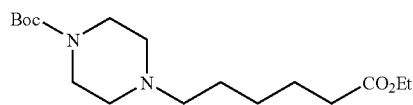

24.3 g (90 mMol) 6-Iodohexanoic acid-ethylester and 16.76 g (90 mMol) 1-Boc-piperazine 1 were dissolved in 75 ml THF and 16.95 ml (99 mMol) Diisopropyl-ethyl-amine was added to the solution. The reaction mixture was heated under reflux for 6 h.

The solvent was then evaporated under vacuum. The residue was dissolved in EtOAc and the solution obtained was washed 3 times with a NaHCO$_3$ solution and once with water. After having dried the organic layer over MgSO$_4$ and evaporated the solvent, the remaining oil was purified by chromatography using EtOAc.

Yield: 27.6 g (93%) $^1$H-NMR (CDCl3) δ 1.25 (t, 3H, O—C—CH$_3$); 1.3-1.38 (m, 2H); 1.45 (s, 9H, t-Bu); 1.48-1.55 (m, 2H); 1.6-1.68 (m, 2H); 2.27-2.4 (m, 8H, 3×C—N—CH$_2$, CH$_2$—CO); 3.42 (t, 4H, 2×CO—N—CH$_2$); 4.12 (q, 2H, O—CH$_2$)

6-(piperazine-1-yl)-hexanoic acid-ethylester (3)

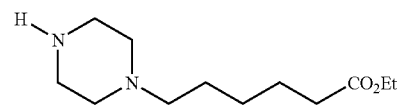

26.3 g (80 mMol) 4-Boc-1-(5-ethoxycarbonyl-pentyl)-piperazine (2) was dissolved in 150 ml 2N HCl and the solution was distilled using a rotary evaporator at 50° C. under vacuum. The pH of the residue was altered to 10 with a 15% NaOH solution and the product was extracted with EtOAc. The organic layer was dried over MgSO$_4$ and evaporated.

Yield: 2.2 g (66%) HPLC >98% [Lichrosorb RP 18 (5 µm) Merck# 50333; Acetonitrile/(H$_2$O+0.01M TBAS)=25:75; flow 1 ml/Min.; 6.3 Min.]

4-(2-Chloroacetyl)-1-(5-ethoxycarbonyl-pentyl)-piperazine (4)

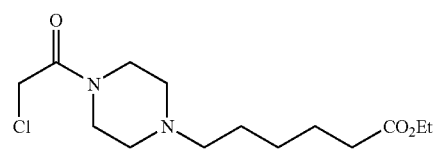

12.2 g (53 mMol) 6-(piperazine-1-yl)-hexanoic acid ethylester 3 and 7.35 ml (53 mMol) TEA were dissolved in 140 ml CH$_2$Cl$_2$. After having added 4.22 ml (53 mMol) Chloroacetylchloride drop-wise to the solution at 0° C., the reaction mixture was stirred for 2 h at RT. The solution was washed twice with a NaHCO$_3$-solution and 1 time with water. After having dried the organic layer over MgSO$_4$ and evaporated the solvent, the remaining oil was purified by chromatography using EtOAc/CH$_3$OH (10:1, v:v)

Yield: 10.3 g (67%) R$_F$=0.44 (EtOAc/CH$_3$OH=5:1) HPLC 91% [Lichrosorb RP 18 (5 µm) Merck# 50333; Acetonitrile/(H$_2$O+0.01M TBAS)=25:75; flow 1 ml/Min.; 2.1 Min.]

At this stage, the compound is pure enough for the synthesis of compound (5).

4-(2-Cyanoacetyl)-1-(5-ethoxycarbonyl-pentyl)-piperazine (5)

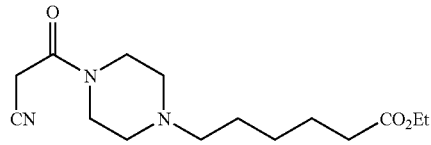

10.3 g (36 mMol) 4-(2-Chloroacetyl)-1-(5-ethoxycarbonyl-pentyl)-piperazine (4) and 2.76 g (42 mMol) KCN were dissolved in 50 ml DMSO and the mixture was stirred for 3 h at RT. After cooling down the solution, the mixture was poured into 300 ml water and the product was extracted with EtOAc. The organic layer was washed twice with saturated NaCl solution, dried over MgSO$_4$ and then the solvent was evaporated. The residue was purified by chromatography using EtOAc/CH$_3$OH (10:1, v:v)

Yield: 5.2 g (53%) HPLC >98% [Lichrosorb RP 18 (5 μm) Merck# 50333; Acetonitrile/(H$_2$O+0.01M TBAS)=25:75; flow 1 ml/Min.; 2.0 Min.]$^1$H-NMR (CDCl$_3$) δ 1.25 (t, 3H, O—C—CH$_3$); 1.31-1.39, 1.46-1.54, 1.6-1.68 (m, m, m, 6H, N—C—(CH$_2$)$_3$—C—CO); 2.3, 2.36, 2.42 u. 2.49 (t, t, t, t, 8H, 3×C—N—CH$_2$, CH$_2$—CO); 3.45 u. 3.62 (t, t, 4H, 2×CO—N—CH$_2$); 3.53 (s, 2H, NC—CH$_2$); 4.12 (q, 2H, O—CH$_2$)

4-[2-Cyano-3-(4-hydroxy-phenyl)-acryloyl]-1-(5-ethoxycarbonyl-pentyl)-piperazine (6)

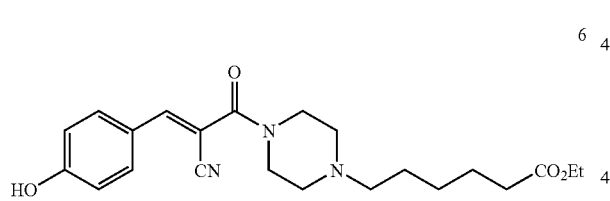

5.15 g (18.4 mMol) 4-(2-Cyano-acetyl)-1-(5-ethoxycarbonyl-pentyl)-piperazine 5 and 2.25 g (18.4 mMol) 4-Hydroxy benzaldehyde was dissolved in 30 mL Pyridine. After adding 0.33 ml Piperidine to the solution, the reaction mixture was stirred for 3 h at 55° C. and 20 h at RT. Pyridine was then evaporated under vacuum and the residue was dissolved in EtOAc. The organic solution was washed 3 times with a saturated NaCl-solution, dried over MgSO$_4$ and the solvent was evaporated. The remaining product was purified by chromatography using EtOAc/CH$_3$OH (10:1, v:v)

Yield: 5.8 g (79%) HPLC >98% [Lichrosorb RP 18 (5 am) Merck# 50333; Acetonitrile/(H$_2$O+0.01M TBAS)=25:75; flow 1 ml/Min.; 3.0 Min.]$^1$H-NMR (d$_6$DMSO) δ 1.17 (t, 3H, O—C—CH$_3$); 1.23-1.32, 1.38-1.47, 1.49-1.57 (m, m, m, 6H, N—C—(CH$_2$)$_3$—C—CO); 2.24-2.31. 2.38, 2.42 u. 2.49 (m, t, 8H, 3×C—N—CH$_2$, CH$_2$—CO); 3.54 (t, 4H, 2×CO—N—CH$_2$); 4.04 (q, 2H, O—CH$_2$); 6.91 u. 7.83 (m, m, 4H, Ph); 7.62 (s, 1H, CH=C—CN); 10.47 (br.s, 1H, OH)

4-[2-Cyano-3-(4-hydroxy-phenyl)-acryloyl]-1-(5-hydroxycarbonyl-pentyl)-piperazine-1-ium; hydrochloride (7)

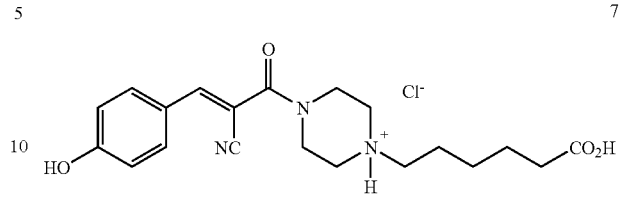

5.79 g (14.5 mMol) 4-[2-Cyano-3-(4-hydroxy-phenyl)-acryloyl]-1-(5-ethoxycarbonyl-pentyl)-piperazine (6) was dissolved in 25 ml Methanol. 20 ml (40 mMol) 2N NaOH was added to the solution at RT and the reaction mixture was stirred for 2 h at RT. The pH of the solution was then altered to 4.2 with 2N HCl and Methanol was distilled under vacuum. It remained an aqueous phase with an oily layer which recrystallised after a short time. The product was filtered off and washed with water and acetone.

Yield: 4.5 g (76%) HPLC 94% [Lichrosorb RP 18 (5 am) Merck# 50333; Acetonitrile/(H$_2$O+0.01M TBAS) =20:80; flow 1 ml/Min.; 2.3 Min.]$^1$H-NMR (d$_6$DMSO) δ 1.23-1.35, 1.46-1.56, 1.65-1.78 (m, m, m, 6H, N—C—(CH$_2$)$_3$—C—CO); 2.23 (t, 2H, CH$_2$—CO); 3.05 (m, 4H, 2×CO—N—CH$_2$); 3.5 (m, 4H, 2×N$^+$—CH$_2$—C—N); 4.25 (m, 2H, N$^+$—CH$_2$); 6.95 u. 7.86 (m, m, 4H, Ph); 7.71 (s, 1H, CH=C—CN); 10.66 (s, 1H, $^+$NH); 11.34 and 12.04 (br.s, br, s, 2H, 2×OH)

4-[2-Cyano-3-(4-hydroxy-phenyl)-acryloyl]-1-[5-(2,5-dioxo-pyrrolidine-1-yloxycarbonyl)-pentyl]-piperazine-1-ium hydrochloride (8)

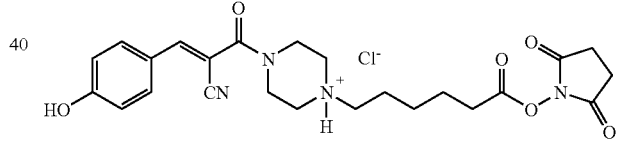

1.86 g (5 in Mol) 4-[2-Cyano-3-(4-hydroxy-phenyl)-acryloyl]-1-(5-hydroxycarbonyl-pentyl)-piperazine-1-ium hydrochloride 7 and 0.64 g (5.5 in Mol) N-Hydroxy-succinimide were dissolved in 25 ml DMF. 2.06 g (10 mMol) Dicyclohexyl-carbodiimide was added to the solution and the reaction mixture was stirred for 20 h at RT. The precipitate was filtered off and the filtrate was mixed to 200 ml Diisopropylether. At this point, an oil formed. After having cooled down the mixture to −20° C., the residue got very viscous and a clear liquid could be removed. After having washed the residue twice with Diisopropylether, the oil was dissolved in Acetonitrile. The solution was filtered and the filtrate was then evaporated. The remaining solid foam was treated with EtOAc and filtered off.

Yield: 2.03 g (81%) HPLC 97% [Lichrosorb RP 18 (5 μm) Merck# 50333; Acetonitrile/(H$_2$O+0.01M TBAS)=15:85; flow 1 ml/Min.; 6.4 Min.]$^1$H-NMR (d$_6$DMSO) δ 1.35-1.47, 1.62-1.72, 1.72-1.85 (m, m, m, 6H, N—C—(CH$_2$)$_3$—C—CO); 2.67-2.75 (m, 2H, CH$_2$—CO); 2.83 (s, 4H, O-Su); 3.07 (m, 4H, 2×CO—N—CH$_2$); 3.45-3.6 (m, 4H, 2×N$^+$—CH$_2$—C—N); 4.27 (m, 2H, N$^+$—CH$_2$); 6.97 and 7.87 (m, m, 4H, Ph); 7.72 (s, 1H, CH=C—CN); 10.69 u. 11.52 (s, s, 2H, $^+$NH, OH)

The invention claimed is:

1. A method for characterising a polypeptide, which method comprises the steps of:
   (a) cleaving the polypeptide with a sequence specific cleavage reagent to form peptide fragments;
   (b) capping one or more ε-amino groups that are present with a lysine reactive agent;
   (c) analyzing the peptide fragments by
      (a) labelling the analyte with a light-absorbing label that absorbs light at a predetermined frequency, to form a labelled analyte;
      (b) embedding the labelled analyte in a matrix wherein the matrix comprises at least one light-absorbing compound, to form an embedded labelled analyte;
      (c) desorbing the embedded labelled analyte by exposing it to light having the predetermined frequency, to form a desorbed analyte; and
      (d) detecting the desorbed analyte by mass spectrometry, to characterise the analyte to form a mass fingerprint for the polypeptide; and
   (d) determining the identity of the polypeptide from the mass fingerprint.

2. A method for characterising a population of polypeptides, which method comprises the steps of:
   (a) separating one or more polypeptides from the population;
   (b) cleaving one or more polypeptides with a sequence specific cleavage reagent to form peptide fragments;
   (c) capping one or more ε-amino groups that are present with a lysine reactive agent;

(d) analysing the peptide fragments by
  (a) labelling the analyte with a light-absorbing label that absorbs light at a predetermined frequency, to form a labelled analyte;
  (b) embedding the labelled analyte in a matrix wherein the matrix comprises at least one light-absorbing compound, to form an embedded labelled analyte;
  (c) desorbing the embedded labelled analyte by exposing it to light having the predetermined frequency, to form a desorbed analyte; and
  (d) detecting the desorbed analyte by mass spectrometry, to characterise the analyte to form a mass fingerprint for one or more polypeptides; and
(e) determining the identity of one or more polypeptides from the mass fingerprint.

3. A method for comparing a plurality of samples, each sample comprising one or more polypeptides, which method comprises the steps of:
  (a) separating one or more polypeptides from each of the samples;
  (b) cleaving the polypeptides with a sequence specific cleavage reagent to form peptide fragments;
  (c) capping one or more ε-amino groups that are present with a lysine reactive agent;
  (d) analysing peptide fragments by
    (a) labelling the analyte with a light-absorbing label that absorbs light at a predetermined frequency, to form a labelled analyte;
    (b) embedding the labelled analyte in a matrix wherein the matrix comprises at least one light-absorbing compound, to form an embedded labelled analyte;
    (c) desorbing the embedded labelled analyte by exposing it to light having the predetermined frequency, to form a desorbed analyte; and
    (d) detecting the desorbed analyte by mass spectrometry, to characterise the analyte to form a mass fingerprint for one or more polypeptides from the samples; and
  (e) determining the identity of one or more polypeptides in the samples from one or more mass fingerprints.

4. The method according to claim 1, wherein the lysine-reactive agent is a labelled lysine-reactive agent.

5. A method for comparing a plurality of samples, each sample comprising one or more polypeptides, which method comprises:
  (a) capping one or more ε-amino groups that are present in each sample with a labelled lysine reactive agent;
  (b) pooling the samples;
  (c) separating one or more polypeptides from the pooled samples;
  (d) cleaving the polypeptides with a sequence specific cleavage reagent to form peptide fragments;
  (e) analyzing peptide fragments by
    (a) labelling the analyte with a light-absorbing label that absorbs light at a predetermined frequency, to form a labelled analyte;
    (b) embedding the labelled analyte in a matrix wherein the matrix comprises at least one light-absorbing compound, to form an embedded labelled analyte;
    (c) desorbing the embedded labelled analyte by exposing it to light having the predetermined frequency, to form a desorbed analyte; and
    (d) detecting the desorbed analyte by mass spectrometry, to characterise the analyte to form a mass fingerprint for one or more polypeptides from the samples; and
  (f) determining the identity of one or more polypeptides in the samples from one or more mass fingerprints;

wherein the same label is employed for polypeptides or peptides from the same sample, and different labels are employed for polypeptides or peptides from different samples, such that the sample from which a polypeptide or peptide originates can be determined from its label.

6. The method according to claim 5, wherein the sequence specific cleavage agent cleaves the one or more polypeptides on the C-terminal side of a lysine residue.

7. The method according to claim 5, wherein the specific cleavage agent comprises Lys-C or Trypsin.

8. The method according to claim 5, wherein the peptide fragments having capped ε-amino groups are removed by affinity capture, and wherein the lysine reactive agent comprises biotin.

9. The method according to claim 5, wherein the lysine reactive agent comprises a hindered Michael reagent.

10. The method according to claim 9, wherein the hindered Michael agent comprises a compound having the following structure:

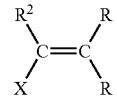

wherein X is an electron withdrawing group that is capable of stabilizing a negative charge; the R groups independently comprise a hydrogen, a halogen, an alkyl, an aryl, or an aromatic group with the proviso that at least one of the R groups comprises a sterically hindering group; and the group $R^2$ comprises a hydrogen, a halogen, a hydrocarbon group, an electron withdrawing group, or a linker capable of attachment to an affinity capture functionality or a solid phase support.

11. The method according to claim 1, further comprising reducing cysteine disuiphide bridges in the polypeptide to form free thiols and capping the free thiols, prior to cleaving the polypeptide.

12. The method according to claim 1, further comprising deactivating the cleavage agent after cleaving the polypeptide.

13. The method according to claim 1, wherein the sequence specific cleavage agent cleaves each isolated polypeptide on the C-terminal side of a lysine residue.

14. The method according to claim 1, wherein the sequence specific cleavage agent comprises Lys-C or Trypsin.

15. The method according to claim 1, wherein the peptide fragments having capped ε-amino groups are removed by affinity capture, and wherein the lysine reactive agent comprises biotin.

16. The method according to claim 1, wherein the lysine reactive agent comprises a hindered Michael reagent.

17. The method according to claim 16, wherein the hindered Michael agent comprises a compound having the following structure:

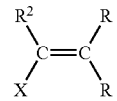

wherein X is an electron withdrawing group that is capable of stabilizing a negative charge; the r groups independently comprise a hydrogen, a halogen, an alkyl, an aryl, or an aromatic group with the proviso that at least one of the R groups comprises a sterically hindering group; and the group $R^2$ comprises a hydrogen, a halogen, a hydrocarbon group, an electron withdrawing group, or a linker capable of attachment to an affinity capture functionality or a solid phase support.

18. The method according to claim 2, further comprising reducing cysteine disulphide bridges in the polypeptide to form free thiols and capping the free thiols, prior to cleaving the polypeptide.

19. The method according to claim 2, further comprising deactivating the cleavage agent after cleaving the polypeptide.

20. The method according to claim 3, further comprising reducing cysteine disulphide bridges in the polypeptide to form free thiols and capping the free thiols, prior to cleaving the polypeptide.

21. The method according to claim 3, further comprising deactivating the cleavage agent after cleaving the polypeptide.

22. The method according to claim 5, further comprising reducing cysteine disulphide bridges in the polypeptide to form free thiols and capping the free thiols, prior to capping one or more $\epsilon$-amino groups.

23. The method according to claim 5, further comprising deactivating the cleavage agent after cleaving the polypeptides.

* * * * *